US010736962B2

(12) United States Patent
Deng et al.

(10) Patent No.: US 10,736,962 B2
(45) Date of Patent: Aug. 11, 2020

(54) RECOMBINANT MVA OR MVADELE3L EXPRESSING HUMAN FLT3L AND USE THEREOF AS IMMUNO-THERAPEUTIC AGENTS AGAINST SOLID TUMORS

(71) Applicant: Memorial Sloan Kettering Cancer Center, New York, NY (US)

(72) Inventors: Liang Deng, New York, NY (US); Stewart Shuman, New York, NY (US); Jedd Wolchok, New York, NY (US); Taha Merghoub, New York, NY (US); Weiyi Wang, New York, NY (US); Peihong Dai, New York, NY (US); Ning Yang, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/079,222

(22) PCT Filed: Feb. 25, 2017

(86) PCT No.: PCT/US2017/019549
§ 371 (c)(1),
(2) Date: Aug. 23, 2018

(87) PCT Pub. No.: WO2017/147554
PCT Pub. Date: Aug. 31, 2017

(65) Prior Publication Data
US 2019/0046640 A1 Feb. 14, 2019

Related U.S. Application Data

(60) Provisional application No. 62/300,066, filed on Feb. 25, 2016, provisional application No. 62/418,786, filed on Nov. 7, 2016, provisional application No. 62/418,788, filed on Nov. 8, 2016.

(51) Int. Cl.
*C12N 15/86* (2006.01)
*A61K 39/395* (2006.01)
*A61K 39/00* (2006.01)
*C07K 16/28* (2006.01)
*C07K 14/52* (2006.01)
*A61K 35/768* (2015.01)
*A61P 35/00* (2006.01)
*A61K 9/00* (2006.01)

(52) U.S. Cl.
CPC ........ *A61K 39/3955* (2013.01); *A61K 9/0019* (2013.01); *A61K 35/768* (2013.01); *A61K 39/0011* (2013.01); *A61P 35/00* (2018.01); *C07K 14/521* (2013.01); *C07K 16/2818* (2013.01); *C07K 16/2827* (2013.01); *C12N 15/86* (2013.01); *A61K 2039/505* (2013.01); *A61K 2039/55522* (2013.01); *C07K 2317/76* (2013.01); *C12N 2710/24032* (2013.01); *C12N* *2710/24121* (2013.01); *C12N 2710/24132* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 5,494,807 A | 2/1996 | Paoletti et al. | |
| 5,762,938 A | 6/1998 | Paoletti et al. | |
| 5,766,882 A | 6/1998 | Falkner et al. | |
| 6,004,777 A | 12/1999 | Tartaglia et al. | |
| 6,265,189 B1 | 7/2001 | Paoletti et al. | |
| 6,372,455 B1 | 4/2002 | Jacobs et al. | |
| 6,475,999 B1 | 11/2002 | Mastrangelo et al. | |
| 6,548,068 B1 | 4/2003 | Schlom et al. | |
| 6,750,043 B2 | 6/2004 | Jacobs et al. | |
| 6,761,893 B2 | 7/2004 | Chaplin et al. | |
| 6,846,652 B2 | 1/2005 | Jacobs et al. | |
| 6,942,855 B2 | 9/2005 | Jacobs et al. | |
| 7,001,718 B2 | 2/2006 | Jacobs et al. | |
| 7,049,145 B2 | 5/2006 | Erfle et al. | |

(Continued)

FOREIGN PATENT DOCUMENTS

| | | |
|---|---|---|
| CA | 2435967 A1 | 1/2005 |
| CA | 2436196 A1 | 1/2005 |

(Continued)

OTHER PUBLICATIONS

Chavan et al. Expression of CCL20 and Granulocyte-Macrophage Colony-Stimulating Factor, but Not Flt3-L, from Modified Vaccinia Virus Ankara Enhances Antiviral Cellular and Humoral Immune Responses. Journal of Virology, Aug. 2006, p. 7676-7687, vol. 80, No. 15.*
Zurkova et al. The expression of the soluble isoform of hFlt3 ligand by recombinant vaccinia virus enhances immunogenicity of the vector. Oncology Reports 21: 1335-1343, 2009.*
Brandt et al., "The N-terminal domain of the vaccinia virus E3L-protein is required for neurovirulence" Virology, vol. 333, No. 2, pp. 263-270 (2005) DOI: 10.1128/JVI.75.2.850-856.2001.
International Search Report and Written Opinion, PCT/US2017/019548, Memorial Sloan Kettering Cancer Center, 17 pages (dated Aug. 8, 2017).

(Continued)

*Primary Examiner* — Nianxiang Zou
(74) *Attorney, Agent, or Firm* — Foley & Lardner LLP

(57) ABSTRACT

The present disclosure relates generally to the fields of oncology, virology and immunotherapy. It concerns poxviruses, specifically the highly attenuated modified vaccinia virus Ankara (MVA), and a recombinant modified vaccinia Ankara virus with deletion of vaccinia virulence factor E3 (MVAΔE3L), each further modified to express human Fms-like tyrosine kinase 3 ligand (Flt3L) or GM-CSF. The disclosure relates to use of the foregoing recombinant viruses as cancer immunotherapeutic agents. The foregoing recombinant poxviruses can also be used in combination with immune checkpoint blockade therapy.

22 Claims, 38 Drawing Sheets

Specification includes a Sequence Listing.

(56) References Cited

U.S. PATENT DOCUMENTS

| | | |
|---|---|---|
| 7,208,313 B2 | 4/2007 | McCart et al. |
| 7,252,817 B2 | 8/2007 | Coffey et al. |
| 7,256,037 B2 | 8/2007 | Ellenhorn et al. |
| 7,306,902 B2 | 12/2007 | Thompson et al. |
| 7,431,929 B2 | 10/2008 | Jacobs et al. |
| 7,550,147 B2 | 6/2009 | Howley et al. |
| 7,588,767 B2 | 9/2009 | Szalay et al. |
| 7,807,146 B2 | 10/2010 | Delcayre et al. |
| 8,052,968 B2 | 11/2011 | Chen et al. |
| 8,105,578 B2 | 1/2012 | Roberts et al. |
| 8,377,688 B2 | 2/2013 | Delcayre et al. |
| 8,506,947 B2 | 8/2013 | McCart et al. |
| 8,679,509 B2 | 3/2014 | Evans et al. |
| 8,747,837 B2 | 6/2014 | Kirn et al. |
| 8,778,328 B2 | 7/2014 | Erbs et al. |
| 8,852,927 B2 | 10/2014 | Szalay et al. |
| 8,859,256 B2 | 10/2014 | Szalay et al. |
| 8,865,153 B2 | 10/2014 | Szalay et al. |
| 8,871,219 B2 | 10/2014 | Heeney et al. |
| 9,101,658 B2 | 8/2015 | Contag et al. |
| 9,175,057 B2 | 11/2015 | Schlom et al. |
| 9,180,150 B2 | 11/2015 | Erbs et al. |
| 9,234,197 B2 | 1/2016 | Chaput et al. |
| 9,273,327 B2 | 3/2016 | Cottingham |
| 9,670,506 B2 | 6/2017 | Pantaleo et al. |
| 9,879,281 B2 | 1/2018 | Son et al. |
| 9,919,062 B2 | 3/2018 | Kirn |
| 2002/0061298 A1 | 5/2002 | Coffey et al. |
| 2002/0155529 A1 | 10/2002 | Jacobs et al. |
| 2003/0113919 A1 | 6/2003 | Emtage et al. |
| 2004/0091995 A1 | 5/2004 | Schlom et al. |
| 2004/0208850 A1 | 10/2004 | Ellenhorn et al. |
| 2005/0287162 A1 | 12/2005 | Baier et al. |
| 2006/0088909 A1 | 4/2006 | Compans et al. |
| 2006/0099181 A1 | 5/2006 | Jacobs et al. |
| 2006/0216312 A1 | 9/2006 | Jacobs |
| 2007/0036758 A1 | 2/2007 | Jacobs et al. |
| 2007/0178065 A1 | 8/2007 | Lattime et al. |
| 2007/0275010 A1 | 11/2007 | Feinberg et al. |
| 2008/0075694 A1 | 3/2008 | Drexler et al. |
| 2008/0181870 A1 | 7/2008 | Lowenstein et al. |
| 2009/0162288 A1 | 6/2009 | Chen et al. |
| 2010/0247622 A1 | 9/2010 | Coffey et al. |
| 2010/0316609 A1 | 12/2010 | Dewhurst et al. |
| 2011/0064650 A1 | 3/2011 | Szalay |
| 2011/0142874 A1 | 6/2011 | Jacobs et al. |
| 2011/0206640 A1 | 8/2011 | Bell et al. |
| 2012/0308484 A1 | 12/2012 | Szalay et al. |
| 2012/0328649 A1 | 12/2012 | Falkner et al. |
| 2013/0195912 A1 | 8/2013 | Cottingham |
| 2013/0243813 A1 | 9/2013 | Howley et al. |
| 2013/0295675 A1 | 11/2013 | Jacobs et al. |
| 2014/0086976 A1 | 3/2014 | Szalay et al. |
| 2014/0087362 A1 | 3/2014 | Szalay et al. |
| 2014/0193859 A1 | 7/2014 | Jacobs et al. |
| 2014/0271549 A1 | 9/2014 | Szalay |
| 2014/0377870 A1 | 12/2014 | Jacobs et al. |
| 2015/0037355 A1 | 2/2015 | Kirn et al. |
| 2015/0202272 A1 | 7/2015 | Lauterbach et al. |
| 2015/0240246 A1 | 8/2015 | Jacobs et al. |
| 2015/0250837 A1 | 9/2015 | Nolin et al. |
| 2015/0250869 A1 | 9/2015 | Sene et al. |
| 2015/0283220 A1 | 10/2015 | Mandl et al. |
| 2016/0130564 A1 | 5/2016 | Marais et al. |
| 2016/0185875 A1 | 6/2016 | Cheng et al. |
| 2016/0235793 A1 | 8/2016 | Thorne |
| 2016/0271239 A1 | 9/2016 | Foy et al. |
| 2016/0339090 A1 | 11/2016 | Hacohen et al. |
| 2017/0020938 A1 | 1/2017 | Wang et al. |
| 2017/0021009 A1 | 1/2017 | Jacobs et al. |
| 2017/0106065 A1 | 4/2017 | Foy et al. |
| 2017/0143780 A1 | 5/2017 | Zitvogel et al. |
| 2017/0157188 A1 | 6/2017 | Silvestre et al. |
| 2017/0246280 A1 | 8/2017 | Pantaleo et al. |
| 2017/0266270 A1 | 9/2017 | Foy et al. |
| 2017/0340687 A1 | 11/2017 | Nakao et al. |

FOREIGN PATENT DOCUMENTS

| | | |
|---|---|---|
| CN | 105039269 A | 11/2015 |
| EP | 2 771 465 A1 | 9/2014 |
| EP | 2 136 633 B1 | 10/2015 |
| EP | 3 142 690 A2 | 4/2017 |
| WO | WO-03/023040 A2 | 3/2003 |
| WO | WO-2004/003987 A1 | 1/2004 |
| WO | WO-2004/024756 A2 | 3/2004 |
| WO | WO-2006/120474 A2 | 11/2006 |
| WO | WO-2007/119895 A1 | 10/2007 |
| WO | WO-2008/045346 A2 | 4/2008 |
| WO | WO-2008/113078 A1 | 9/2008 |
| WO | WO-2009/152179 A1 | 12/2009 |
| WO | WO-2011/156470 A1 | 12/2011 |
| WO | WO-2012/009644 | 1/2012 |
| WO | WO-2013/038066 A1 | 3/2013 |
| WO | WO-2014/081976 A1 | 5/2014 |
| WO | WO-2014/036412 A2 | 6/2014 |
| WO | WO-2015/066715 A1 | 5/2015 |
| WO | WO-2015/069571 A1 | 5/2015 |
| WO | WO-2015/084897 A2 | 6/2015 |
| WO | WO-2015/138741 A1 | 9/2015 |
| WO | WO-2016/046357 A1 | 3/2016 |
| WO | WO-2016/128542 A1 | 8/2016 |
| WO | WO-2016/144564 A1 | 9/2016 |
| WO | WO-2016/144564 A1 | 9/2016 |
| WO | WO-2016/168862 A1 | 10/2016 |
| WO | WO-2016/205429 A1 | 12/2016 |
| WO | WO-2017/024000 A1 | 2/2017 |
| WO | WO-2017/037523 A1 | 3/2017 |
| WO | WO-2017/043815 A1 | 3/2017 |
| WO | WO-2017/044780 A1 | 3/2017 |
| WO | WO-2017/075570 A1 | 5/2017 |
| WO | WO-2017/103291 A1 | 6/2017 |
| WO | WO-2017/129765 A1 | 8/2017 |
| WO | WO-2017/147554 | 8/2017 |
| WO | WO-2017/156349 A1 | 9/2017 |
| WO | WO-2017/205674 A1 | 11/2017 |
| WO | WO-2018/016917 A1 | 1/2018 |
| WO | WO-2018/017747 | 1/2018 |
| WO | WO-2018/031694 A1 | 2/2018 |
| WO | WO-2018/049248 A1 | 3/2018 |
| WO | WO-2018/057755 A1 | 3/2018 |
| WO | WO-2018/058258 A1 | 4/2018 |

OTHER PUBLICATIONS

International Search Report and Written Opinion, PCT/US2017/019549, Memorial Sloan Kettering Cancer Center, 17 pages (dated Aug. 14, 2017).

Arsenio et al., "Antagonizing activity of vaccinia virus E3L against human interferons in Huh7 cells," Journal of Virology, vol. 377, No. 1, p. 124-132 (Jul. 20, 2008).

Backes et al., "Viral host-range factor C7 or K1 is essential for modified vaccinia virus Ankara late gene expression in human and murine cells, irrespective of their capacity to inhibit protein kinase R-mediated phosphorylation of eukaryotic translation initiation factor 2a," J. of General Virology, vol. 91, pp. 470-482 (Feb. 1, 2010).

Bommareddy et al., "MEK inhibition enhances oncolytic virus immunotherapy through increased tumor cell killing and T cell activation," Science Translational Medicine, vol. 10, Issue 471 (Dec. 12, 2018).

Brinkman et al., "Fingolimod (FTY720): discovery and development of an oral drug to treat multiple sclerosis," Nature Reviews | Drug Discovery, vol. 9, pp. 883-897 (Nov. 2010).

Dai et al., "Abstract B031: Heat-inactivated modified vaccinia virus Ankara induces type I IFN and antitumor immunity via the cytosolic DNA-sensing pathway," retrieved from: http://www.cancerimmunolrres.aacrjournals.org/content/4/1_Supplement/B031 (Jun. 15, 2018).

Dai et al., "Intratumoral delivery of inactivated modified vaccinia virus Ankara (iMVA) induces systemic antitumor immunity via

(56) References Cited

OTHER PUBLICATIONS

STING and Batf3-dependent dendritic cells" Science Immunology, vol. 2, No. 11, pp. 1-34 (May 19, 2017).

Dai et al., "intratumoral delivery of inactivated modified vaccinia virus Ankara (iMVA) induces systemic antitumor immunity via STING and Batf3-dependent dendritic cells," Sci Immunol., vol. 2, No. 11 (May 19, 2017).

Dai, P et al, Modified Vaccinia Virus Ankara Triggers Type 1 IFN Production in Murine Conventional Dendritic Cells Via A cGAS/STING-Mediated Cytosolic DNA-Sensing Pathway, PLOS Pathogens, Apr. 2014, vol. 10, pp. 1-13.

Dai, P et al, Myxoma Virus Induces Type 1 Interferon Production in Murine Plasmacytoid Dendritic Cells Via A TLR9/MyD88-, IRF5/IRF7-, and IFNAR-Dependent Pathway. Journal of Virology, Oct. 2011, pp. 10814-10825.

Drexler et al., "Modified Vaccinia Virus Ankara for Delivery of Human Tyrosinase as Melanomaassociated Antigen: Induction of Tyrosinase- and Melanoma-specific Human Leukocyte Antigen A*0201-restricted Cytotoxic T Cells in Vitro and in Vivo1," Cancer Research, vol. 59, p. 4955-4963 (Oct. 1, 1999).

Drillien et al, Modified vaccination virus Ankara induces moderate activation of human dendritic cells, Journal of General Virology, Society for General Microbiology, vol. 85, No. Pt 8, Aug. 1, 2004, pp. 2167-2175.

Gomez et al., "MVA and NYVAC as vaccines against emergent infectious diseases and cancer," Current Gene Therapy, vol. 11, No. 3, p. 189-217 (Jun. 2011).

Greiner et al. "The highly attenuated vaccinia virus strain modified virus Ankara induces apoptosis in melanoma cells and allows bystander dendritic cells to generate a potent anti tumoral immunity" Clinical and Experimental Immunology vol. 146. No. 2, Nov. 1, 2006 pp. 344-353.

Guerra et al., "Distinct gene expression profiling after infection of immature human monocyte-derived dendritic cells by the attenuated poxvirus vectors MVA and NYVAC," J. of Virology, vol. 61, No. 16, pp. 8701-8721 (May 30, 2007).

Guerra et al., "Host-Range Restriction in Vaccinia Virus E3L Deletion Mutant Can Be Overcome In Vitro, but Not In Vivo, by Expression of the Influenza Virus NS1 Protein," PLoS ONE. vol. 6 No. 12, p. e28677 (2011).

Harrop et al., "Vaccination of Colorectal Cancer Patients with Modified Vaccinia Ankara Delivering the Tumor Antigen 5T4 (TroVax) Induces Immune Responses which Correlate with Disease Control: A Phase I/II Trial," Clinical Cancer Research, vol. 12, No. 11 Pt. 1, p. 3416-6424 (Jun. 1, 2006).

Hodge et al., "Modified Vaccinia Virus Ankara Recombinants Are as Potent as Vaccinia Recombinants in Diversified Prime and Boost Vaccine Regimens to Elicit Therapeutic Antitumor Responses," American Association for Cancer Research, vol. 63, No. 22, p. 7942-7949 (Nov. 15, 2003).

Hornemann et al., "Replication of Modified Vaccinia Virus Ankara in Primary Chicken Embryo Fibroblasts Requires Expression of the Interferon Resistance Gene E3L," Journal of Virology, vol. 77, No. 15, p. 8394-8407 (Aug. 2003).

Inman, "Immunotherapy/Targeted Therapy Combinations Show Promise in BRAF-Mutated Melanoma," Targeted Oncology, retrieved from: https://www.targetedonc.com/conference/smr-esmo-melanoma/immunotherapytargeted-therapy-combinations-show-promise-in-brafmutated-melanoma (Oct. 20, 2017).

International Search Report and Written Opinion on PCT/US2016/028184, dated Sep. 9, 2016, 17 pages.

International Search Report and Written Opinion on PCT/US2018/032451, dated Aug. 23, 2018, 16 pages.

International Search Report and Written Opinion on PCT/US2018/059476, dated Feb. 14, 2019, 9 pages.

Langland et al., "Inhibition of PKR by vaccinia virus: role of the N- and C-terminal domains of E3L," Journal of Virology, vol. 324, No. 2, p. 419-429 (Jul. 1, 2004).

Lee et al., "The interferon-induced double-stranded RNA-activated protein kinase induces apoptosis," Journal of Virology, vol. 199, No. 2, p. 491-496 (Mar. 1994).

Liu et al., "Deletion of C7L and K1L genes leads to significantly decreased virulence of recombinant vaccinia cirus TianTian," PLoS One, vol. 8, No. 7:e68115, pp. 1-13 (Jul. 1, 2013).

Liu, "Cancer-killing virus plus PD-1 and MEK inhibitors make for a 3-pronged attack on melanoma," retrieved from: https://www.fiercebiotech.com/research/pd-1-mek-inhibitor-and-anti-cancer-virus-a-3-pronged-attack-melanoma, 2 pages (Dec. 12, 2018).

Ludwig et al., "Role of Viral Factor E3L in Modified Vaccinia Virus Ankara Infection of Human HeLa Cells: Regulation of the Virus Life Cycle and Identification of Differentially Expressed Host Genes," Journal of Virology, vol. 79, No. 4, p. 2584-2596 (Feb. 2005).

Mandl, SJ et al, Immunotherapy With MVA-BN-HER2 Induces HER-2-specific Th1 Immunity and Alters the Intratumoral Balance of Effector and Regulatory T cells. Cancer Immunol Immunother, 2012, vol. 61, pp. 19-29.

McIntyre et al., "Mouse models of colorectal cancer as preclinical models," Bioessays, 37(8), pp. 909-920 (Aug. 2015).

Meng et al., "Vaccinia Virus K1L and C7L Inhibit Antiviral Activities Induced by Type I Interferons," Journal of Virology, vol. 83, No. 20, p. 10627-10636 (Oct. 2009).

Nagaria et al., "Combined targeting of RAF and MEK synergistically inhibits tumorigenesis in triple negative breast cancer model systems," Oncotarget, vol. 8, No. 46, pp. 80804-80819 (Aug. 24, 2017).

Nakayama et al., "In vitro comparison between mouse B16 and human melanoma cell lines of the expression of ICAM-1 induced by cytokines and/or hyperthermia," J. Dermatol., 24(6), pp. 351-360 (Jun. 1997).

Pardoll, "The blockade of immune checkpoints in cancer immunotherapy," Nat. Rev. Cancer, 12(4), pp. 252-264 (Mar. 22, 2012).

Peihong et al., "Modified Vaccinia Virus Ankara Triggers Type I IFN Production in Murine Conventional Dendritic Cells via a cGAS/STING-Mediated Cytosolic DNA-Sensing Pathway," PLOS Pathogens, vol. 10, No. 4, p. e1003989 (Apr. 17, 2014).

Peihong, "P339 Intratumoral delivery of modified vaccinia virus Ankara expressing human Flt3L as cancer immunotherapy," 31st Annual Meeting and Associated Programs of the Society for Immunotherapy of Cancer, Pt. 2, p. 1-241 (2016).

Reddy et al., "Influences of BRAF Inhibitors on the Immune Microenvironment and the Rationale for Combined Molecular and Immune Targeted Therapy," Curr. Oncol. Rep., 18(7)15 pages (Jul. 2016).

Sabbatino et al., "Antitumor activity of BRAF inhibitor and IFN combination in BRAF-mutant melanoma," J. Natl. Cancer Inst., 108(7), 11 pages (Feb. 5, 2016).

Schaedler et al., "Sequential administration of a MVA-based MUC1 cancer vaccine and the TLR9 ligand Litenimod (Li28) improves local immune defense against tumors," Vaccine, vol. 35, No. 4, p. 577-585 (Jan. 23, 2017).

Vijaysri et al., "Vaccinia Viruses with Mutations in the E3L Gene as Potential Replication-Competent, Attenuated Vaccines: Intra-Nasal Vaccination," Vaccine, vol. 26, No. 5, p. 664-676 (Jan. 30, 2008).

Waibler et al. "Modified Vaccinia Virus Ankara Induces Tool Line Receptor Independent Type I Interferon Responses" Journal of Virology, vol. 181 No. 22, Nov. 15, 2007 pp. 12102-12110.

Waibler et al., "Modified Vaccinia Virus Ankara Induces Toll-Like Receptor-Independent Type I Interferon Responses," Journal of Virology, vol. 81, No. 22, p. 12101-12110 (Nov. 2007).

Zurkova et al., "The expression of the soluble isoform of hFlt3 ligand by recombinant vaccinia virus enhances immunogenicity of the vector," vol. 21, No. 5, p. 1335-1343 (May 2009).

Caisova et al., "Innate immunity based cancer immunotherapy: B16-F10 murine melanoma model," BMC Cancer, 16:940, 11 pages (2016).

Cao et al., "Innate immune response of human plasmacytoid dendritic cells to poxvirus infection is subverted by vaccinia E3 via its Z-DNA/RNA binding domain," PLOS ONE, vol. 7, No. 5, p. e36823 (May 14, 2012).

(56) References Cited

OTHER PUBLICATIONS

International Search Report and Written Opinion, PCT/US2019/021853, Memorial Sloan Kettering Cancer Center (Jul. 16, 2019).
Kuzu et al., "Current State of Animal (Mouse) Modeling in Melanoma Research," Cancer Growth and Metastasis, 8(S1):81-94 (2015).
Lee et al., "Effect of resveratrol on the metastasis of 4T1 mouse breast cancer cells in vitro and in vivo," Nutrition Res. and Practice, vol. 6, No. 4, pp. 294-300 (2012).
Wang et al., "034 recombinant replication competent attenuated vaccinia virus expressing human Flt3L for cancer immunotherapy," J. Invest. Derm., vol. 136, No. 5, p. S6 (May 2016).
Morales et al, Genome comparison of a nonpathogenic myoxma virus field strain with its ancestor, the virulent Lausanne strain, J. Virol, vol. 83, No. 5, pp. 2397-2403 Mar. 2009.
Curran et al, Tumor Vaccines Expressing Flt2 Ligand Synergize with CTLA-4 Blockade to Reject Preimplanted Tumors, Cancer Research vol. 69 No. 19, Sep. 8, 2009, pp. 7747-7755.
Extended European Search Report, App. No. 17757398.7 (Aug. 19, 2019).
Hammerich et al In situ vaccination for the treatment of cancer, Immunotherapy vol. 8, No. 3, Mar. 1, 2016, pp. 315-330.
Jacobs et al, Vaccinia virus vaccines: Past, present and future, Antiviral Research, Elsevier BV, NL vol. 84, No. 1, Oct. 1, 2009 pp. 1-13.
Alharbi, et al., "ChAdOx1 and MVA based vaccine candidates against MERS-CoV elicit neutralising antibodies and cellular immune responses in mice," Vaccine, vol. 35, pp. 3780-3788 (Jun. 27, 2017).
Angell et al., "From the immune contexture to the Immunoscore: the role of prognostic and predictive immune markers in cancer," Curr. Opin. Immunol., 25, pp. 261-267 (2013).
Antoine et al., "The complete genomic sequence of the modified vaccinia Ankara strain: comparison with other orthopoxviruses", Virology, 244, pp. 365-396 (1998).
Barber, "Innate immune DNA sensing pathways: STING, AIMII and the regulation of interferon production and inflammatory responses", Curr. Opin. Immunol., 23, pp. 10-20 (2011).
Bisht et al., "Severe acute respiratory syndrome coronavirus spike protein expressed by attenuated vaccinia virus protectively immunizes mice," PNAS, vol. 101, pp. 6641-6646 (Apr. 27, 2004).
Brandler et al., "Preclinical studies of a modified vaccinia virus Ankara-based HIV candidate vaccine: antigen presentation and antiviral effect", J. Virol., vol. 84, No. 10, pp. 5314-5328 (2010).
Breitbach et al., "Targeted and armed oncolytic poxviruses for cancer: the lead example of JX-594," Current Pharmaceutical Biotechnology, 13, pp. 1768-1772 (2012).
Castle et al., "Exploiting the mutanome for tumor vaccination", Cancer Res., 72, pp. 1081-1091 (2012).
Chafekar, et al., "MERS-CoV: Understanding the Latest Human Coronavirus Threat," Viruses, 10, 93, 22 pages (Feb. 24, 2018).
Chi et al., "DNA vaccine encoding Middle East respiratory syndrome coronavirus S1 protein induces protective immune responses in mice," Vaccine, vol. 35, pp. 2069-2075 (Apr. 11, 2017).
Coffey et al., "Reovirus therapy of tumors with activated Ras pathway," Science, 282, pp. 1332-1334 (1998).
Deng et al., "STING-Dependent Cytosolic DNA Sensing Promotes Radiation-Induced Type I Interferon-Dependent Antitumor Immunity in Immunogenic Tumors", Immunity, vol. 41, No. 5, pp. 843-852 (2014).
Deng et al., "Vaccinia virus infection attenuates innate immune responses and antigen presentation by epidermal dendritic cells", J Virol., 80, pp. 9977-9987 (2006).
Diamond et al., "Type I interferon is selectively required by dendritic cells for immune rejection of tumors", J Exp Med., vol. 208, No. 10, pp. 1989-2003 (2011).
Du et al., "The spike protein of SARS-CoV—a target for vaccine and therapeutic development," Microbiology, vol. 7, pp. 226-236 (Mar. 2009).
Engelmayer et al., "Vaccinia virus inhibits the maturation of human dendritic cells: a novel mechanism of immune evasion", J Immunol., 163, pp. 6762-6768 (1999).

Fishcer et al., "Modified vaccinia virus Ankara protein F1L is a novel BH3-domain-binding protein and acts together with the early viral protein E3L to block virus-associated apoptosis" Cell Death Differ., 13, pp. 109-118 (2006).
Fuertes et al., "Host type I IFN signals are required for antitumor CD8 T-cell responses through CD8{alpha} dendritic cells", J. Exp. Med., vol. 208, No. 10, 2005-2016 (2011).
Fuertes et al., "Type I interferon response and innate immune sensing of cancer," Trends Immunol., vol. 34, No. 2, pp. 67-73 (Feb. 2013).
Fung et al., "Human Coronavirus: Host-Pathogen Interaction," Annual Review of Microbiology, 73, pp. 529-557 (Jun. 21, 2019).
Gao et al., "Structure-function analysis of STING activation by c[G(2',5')pA(3',5')p] and targeting by antiviral DMXAA", Cell, 154, pp. 748-762 (2013).
Garcia et al., "Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02)", Vaccine, 29, pp. 8309-8316 (2011).
Garrido et al., "The escape of cancer from T lymphocytes: immunoselection of MHC class I loss variants harboring structural-irreversible "hard" lesions," Cancer Immunol. Immunother., 59, pp. 1601-1606 (2010).
GenBank: U94848.1 "Vaccinia virus strain Ankara, complete genomic sequence" p. 1-3 (Apr. 13, 2003).
Gerlini et al., "Metastatic melanoma secreted IL-10 down-regulates CD1 molecules on dendritic cells in metastatic tumor lesions", Am J Pathol., 165, pp. 1853-1863 (2004).
Gitlin et al., "Essential role of mda-5 in type I IFN responses to polyriboinosinic:polyribocytidylic acid and encephalomyocarditis picornavirus", Proc. Natl. Acad. Sci. U S A., vol. 103, No. 22, pp. 8459-8464 (May 30, 2006).
Goepfert et al., "Phase 1 safety and immunogenicity testing of DNA and recombinant modified vaccinia Ankara vaccines expressing HIV-1 virus-like particles", J Infect Dis., 203, pp. 610-619 (2011).
Gomez et al., "The poxvirus vectors MVA and NYVAC as gene delivery systems for vaccination against infectious diseases and cancer", Curr Gene Ther., 8, pp. 97-120 (2008).
Haagmans, et al., "An orthopoxvirus-based vaccine reduces virus excretion after MERS-CoV infection in dromedary camels," Science, vol. 351, pp. 77-81 (Jan. 1, 2016).
Hamid et al., "Safety and Tumor Responses with Lambrolizumab (Anti-PD-1) in Melanoma", The New England journal of medicine, vol. 369, No. 2, pp. 134-144 (2013).
Hodi et al., "Improved survival with ipilimumab in patients with metastatic melanoma", The New England journal of medicine, 363, pp. 711-723 (2010).
Holshue et al., "First Case of 2019 Novel Coronavirus in the United States," New England Journal of Medicine, 9 pages (Jan. 31, 2020).
Huber et al., "Regulation of effector and memory T-cell functions by type I interferon", Immunology, 132, pp. 466-474 (2011).
International Search Report ana Written Opinion, PCT/US2019/051343 (Feb. 7, 2020).
Ishikawa et al., "STING is an endoplasmic reticulum adaptor that facilitates innate immune signaling", Nature, 455, pp. 674-678 (2008).
Jenne et al., "Poxvirus as a vector to transduce human dendritic cells for immunotherapy: abortive infection but reduced APC function", Gene therapy, 7, pp. 1575-1583 (2000).
Jochems et al., "Tumor-infiltrating immune cells and prognosis: the potential link between conventional cancer therapy and immunity", Exp Biol Med.(Maywood), 236, pp. 567-579 (2011).
Kibler et al., "Double-stranded RNA is a trigger for apoptosis in vaccinia virus-infected cells", J. Virol., vol. 71, No. 3, pp. 1992-2003 (1997).
Kirn et al., "Replication-selective virotherapy for cancer: Biological principles, risk management and future directions," Nat. Med., 7, pp. 781-787 (2001).
Kirn et al., "Targeted and armed oncolytic poxviruses: a novel multi-mechanistic therapeutic class for cancer," Nature Reviews—Cancer, 9, pp. 64-71 (2009).

(56) References Cited

OTHER PUBLICATIONS

Kirn et al., "Targeting of interferon-beta to produce a specific, multi-mechanistic oncolytic vaccinia virus", PLoS Med., vol. 4, No. 12, pp. 2001-2012 (2007).
Lacy et al., "Immunotherapy for Melanoma," Expert Rev. Dermatol., 7, pp. 51-68 (2012).
Leach et al., "Enhancement of antitumor immunity by CTLA-4 blockade," Science, 271, pp. 1734-1736 (1996).
Li et al., "Angiotensin-converting enzyme 2 is a functional receptor for the SARS coronavirus," Nature, vol. 426, pp. 450-454 (Nov. 27, 2003).
Li et al., "Disruption of MHC class II-restricted antigen presentation by vaccinia virus," J. Immunol., 175, pp. 6481-6488 (2005).
Li et al., "Early Transmission Dynamics in Wuhan, China, of Novel Coronavirus—Infected Pneumonia," New England Journal of Medicine, 9 pages (Jan. 29, 2020).
Li et al., "Pivotal roles of cGAS-cGAMP signaling in antiviral defense and immune adjuvant effects", Science, 341, pp. 1390-1394 (2013).
Li et al., "Structure of SARS Coronavirus Spike Receptor-Binding Domain Complexed with Receptor," Science, vol. 309, pp. 1864-1868 (Sep. 16, 2005).
Mayr et al., English-language translation of Abstract of: "[The smallpox vaccination strain MVA: marker, genetic structure, experience gained with the parenteral vaccination and behavior in organisms with a debilitated defence mechanism (author's transl)]," Zentralbl Bakteriol, Orig. B, 167, pp. 375-390 (1978).
Mayr et al., English-language translation of Abstract of: "Passage history, properties, and applicability of the attenuated vaccinia virus strain MVA," Infection, 3, pp. 6-14 (1975).
Mellman et al., "Cancer immunotherapy comes of age", Nature, 480, pp. 480-489 (2011).
Meng et al., "C7L Family of Poxvirus Host Range Genes Inhibits Antiviral Activities Induced by Type I Interferons and Interferon Regulatory Factor 1", J. Virol., vol. 86, No. 8, pp. 538-4547 (2012).
Meyer et al., "Mapping of deletions in the genome of the highly attenuated vaccinia virus MVA and their influence on virulence", J. Gen. Virol., 72 ( Pt 5), pp. 1031-1038 (1991).
Mlecnik et al., "Tumor immunosurveillance in human cancers", Cancer Metastasis Rev, 30, pp. 5-12 (2011).
Moss, "Poxviridae: The viruses and their replication," In Fields Virology (Lippincott Williams & Wilkins), pp. 2905-2946 (2007).
Nagorsen et al., "Transcriptional analysis of tumor-specific T-cell responses in cancer patients," Crit. Rev. Immunol., 22, pp. 449-462 (2002).
Nemunaitis, J., "Oncolytic viruses,". Invest. New Drugs, 17, pp. 375-386 (1999).
Oble et al., "Focus on TILs: prognostic significance of tumor infiltrating lymphocytes in human melanoma", Cancer immunity, 9, pp. 1-20 (2009).
Park et al., "Use of a targeted oncolytic poxvirus, JX-594, in patients with refractory primary or metastatic liver cancer: a phase I trial," Lancet Oncol., 9, pp. 533-542 (May 19, 2008).
Peggs et al., "Blockade of CTLA-4 on both effector and regulatory T-cell compartments contributes to the antitumor activity of anti-CTLA-4 antibodies", J Exp Med., 206, pp. 1717-1725 (2009).
Peiris, et al., "The Severe Acute Respiratory Syndrome," New England Journal of Medicine, vol. 349, pp. 2431-2441 (Dec. 18, 2003).
Perkus et al., "Vaccinia virus host genes," Virology, 179(1), pp. 276-286 (1990).
Pramanick et al., "Excipient selection in parenteral formulation development", Pharma Times, vol. 45, No. 3, pp. 65-77 (2013).
Raj et al., "Dipeptidyl peptidase 4 is a functional receptor for the emerging human coronavirus—EMC," Nature, vol. 495, 6 pages (Mar. 13, 2013).
Robert et al., "Ipilimumab plus dacarbazine for previously untreated metastatic melanoma", The New England journal of medicine, 364, pp. 2517-2526 (2011).
Sato et al., "Distinct and essential roles of transcription factors IRF-3 and IRF-7 in response to viruses for IFN-alpha/beta gene induction", Immunity, 13, pp. 539-548 (2000).
Sauer et al., "The N-ethyl-N-nitrosourea-induced Goldenticket mouse mutant reveals an essential function of Sting in the in vivo interferon response to Listeria monocytogenes and cyclic dinucleotides", Infection and immunity, vol. 79, No. 2, pp. 688-694 (2011).
Schumacher et al., "Neoantigens in cancer immunotherapy", Science, 348, pp. 69-74 (2015).
Sharma et al., "The future of immune checkpoint therapy", Science, 348, pp. 56-61 (2015).
Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBio, vol. 6, No. 4, pp. 1-9 (2015).
Song, et al., "Middle East Respiratory Syndrome Coronavirus Spike Protein Delivered by Modified Vaccinia Virus Ankara Efficiently Induces Virus-Neutralizing Antibodies," Journal of Virology, vol. 87, pp. 11950-11954 (Nov. 2013).
Sun et al., "Cyclic GMP-AMP synthase is a cytosolic DNA sensor that activates the type I interferon pathway", Science, 339, pp. 786-791 (2013).
Sutter et al., "Vaccinia vectors as candidate vaccines: the development of modified vaccinia virus Ankara for antigen delivery," Current Drug Targets—Infectious Disorders 3, pp. 263-271 (2003).
Tagliamonte et al., "Antigen-specific vaccines for cancer treatment", Human vaccines & immunotherapeutics, 10, pp. 3332-3346 (2014).
Takaoka et al., "New aspects of IFN-alpha/beta signalling in immunity, oncogenesis and bone metabolism", Cancer Sci., vol. 94, No. 5, pp. 405-411 (2003).
Thorne et al., "Rational strain selection and engineering creates a broad-spectrum, systemically effective oncolytic poxvirus, JX-963", J Clin Invest., vol. 117, No. 11, pp. 3350-3358 (2007).
Topalian et al., "Immune checkpoint blockade: a common denominator approach to cancer therapy", Cancer Cell, vol. 27, No. 4, pp. 450-461 (2015).
Topalian et al., "Targeting the PD-1/B7-H1(PD-L1) pathway to activate anti-tumor immunity", Curr Opin Immunol., 24, pp. 207-212 (2012).
Tormo et al., "Targeted activation of innate immunity for therapeutic induction of autophagy and apoptosis in melanoma cells", Cancer Cell, vol. 16, No. 2, pp. 103-114 (2009).
Tumeh et al., "PD-1 blockade induces responses by inhibiting adaptive immune resistance", Nature, vol. 515, No. 7258, pp. 568-571 (2014).
Verardi et al., "A vaccinia virus renaissance: new vaccine and immunotherapeutic uses after smallpox eradication", Human vaccines & immunotherapeutics, 8, pp. 961-970 (2012).
Verheust et al., "Biosafety aspects of modified vaccinia virus Ankara (MVA)-based vectors used for gene therapy or vaccination," Vaccine, 30, pp. 2623-2632 (2012).
Volz, et al., "Protective Efficacy of Recombinant Modified Vaccinia Virus Ankara Delivering Middle East Respiratory Syndrome Coronavirus Spike Glycoprotein," Journal of Virology, vol. 89, pp. 8651-8656 (Aug. 2015).
Weaver et al., "The identification and characterization of a monoclonal antibody to the vaccinia virus E3 protein", Virus Res., 130, pp. 269-274 (2007).
Wing et al., "CTLA-4 control over Foxp3 regulatory T-cell function", Science, 322, pp. 271-275 (2008).
Wolchok et al., "Ipilimumab monotherapy in patients with pretreated advanced melanoma: a randomised, double-blind, multicentre, phase 2, dose-ranging study," Lancet Oncol., 11, pp. 155-164 (2010).
Wolchok et al., "Nivolumab plus ipilimumab in advanced melanoma", The New England journal of medicine, 369, pp. 122-133 (2013).
Woo et al., "STING-dependent cytosolic DNA sensing mediates innate immune recognition of immunogenic tumors", Immunity, vol. 41, No. 5, pp. 830-842 (2014).

(56) References Cited

OTHER PUBLICATIONS

Wu et al., "Cyclic GMP-AMP is an endogenous second messenger in innate immune signaling by cytosolic DNA", Science, 339, pp. 826-830 (2013).
Wyatt et al., "Enhanced cell surface expression, immunogenicity and genetic stability resulting from a spontaneous truncation of HIV Env expressed by a recombinant MVA", Virology, 372, pp. 260-272 (2008).
Yong, et al., "Recent Advances in the Vaccine Development Against Middle East Respiratory Syndrome-Coronavirus," Frontiers in Microbiology, vol. 10, 18 pages (Aug. 2, 2019).
Zaki, et al., "Isolation of a Novel Coronavirus from a Man with Pneumonia in Saudi Arabia," The New England Journal of Medicine, vol. 367, pp. 1814-1820 (Nov. 8, 2012).
Zamarin et al., "Localized oncolytic virotherapy overcomes systemic tumor resistance to immune checkpoint blockade immunotherapy", Science translational medicine, vol. 6, No. 226, pp. 1-12 (2014).
Zhang, et al., "A DNA vaccine induces SARS coronavirus neutralization and protective immunity in mice," Nature, vol. 428, pp. 561-564 (Apr. 2004).
Zhou, et al., "A pneumonia outbreak associated with a new coronavirus of probable bat origin," Nature, 23 pages (Feb. 3, 2020).

\* cited by examiner

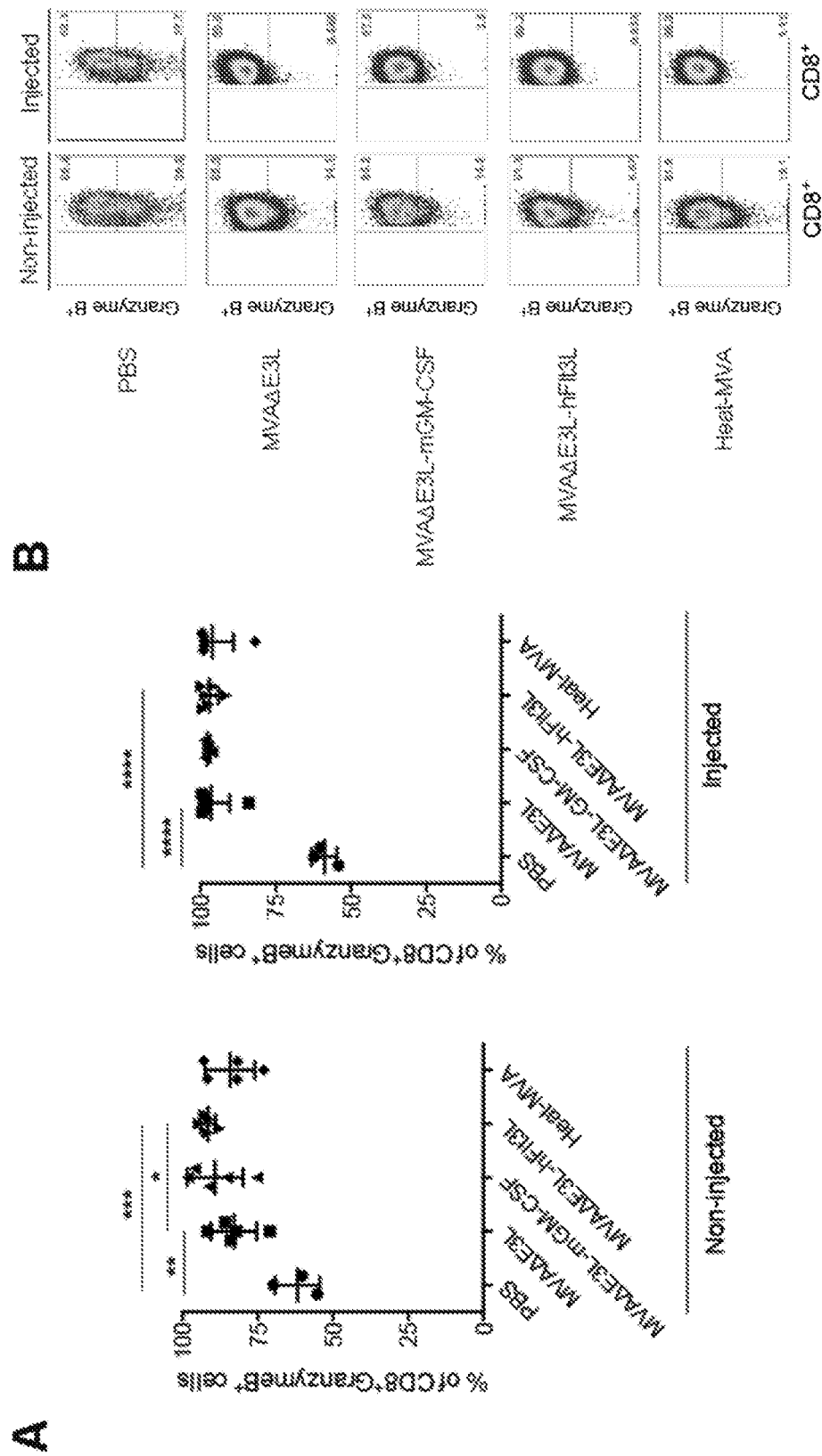
Figure 4A, B

Figure 4C, D
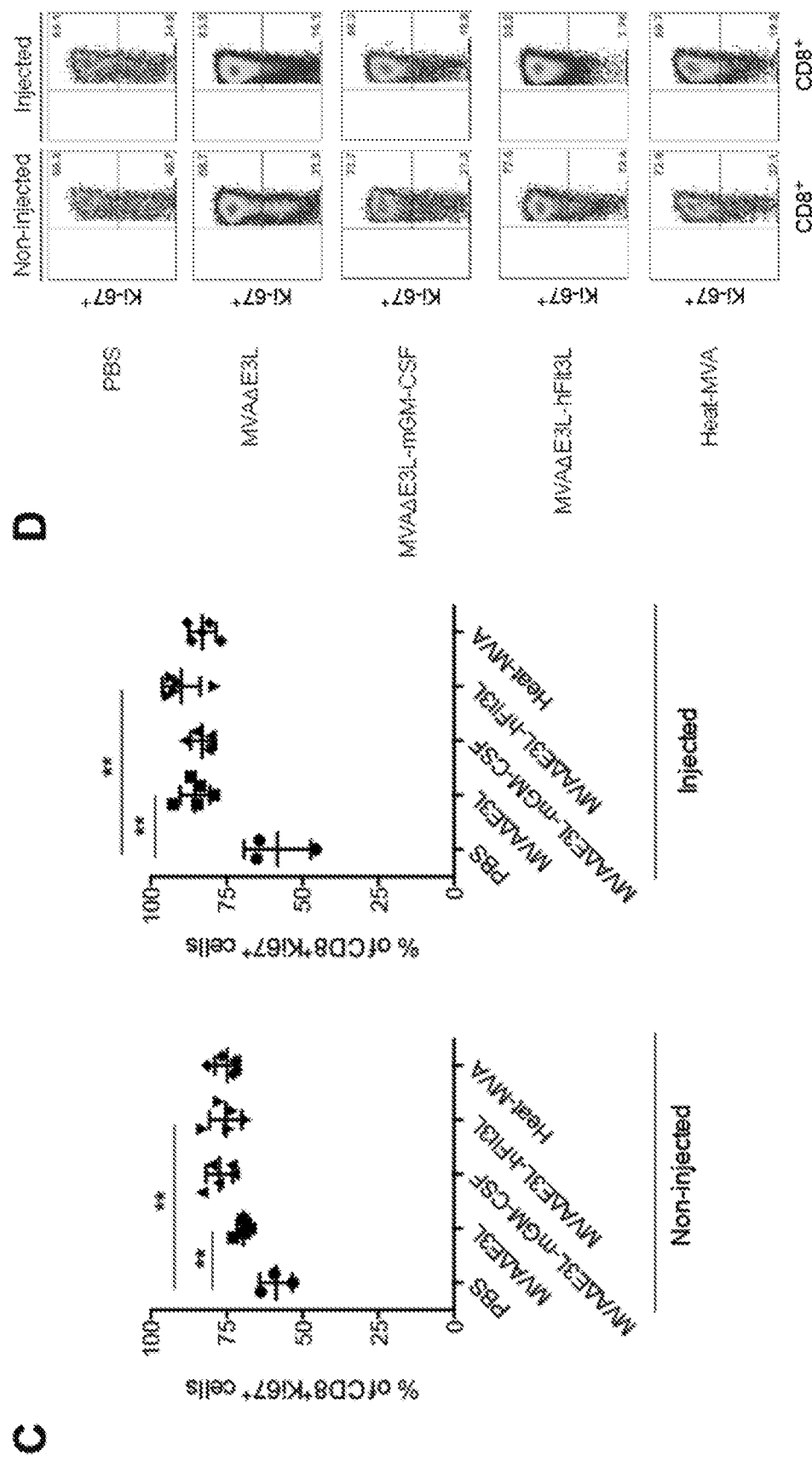

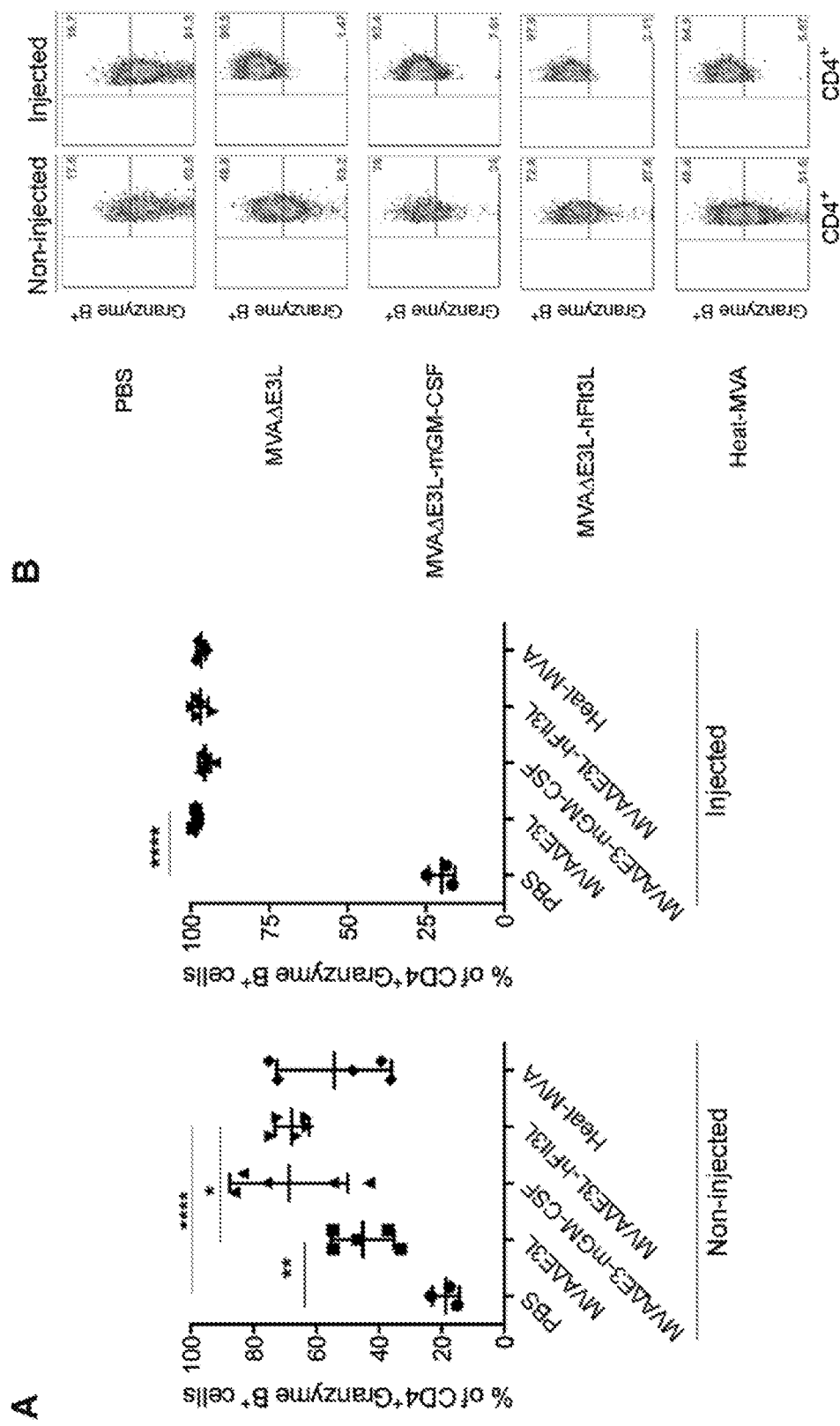
Figure 5A, B

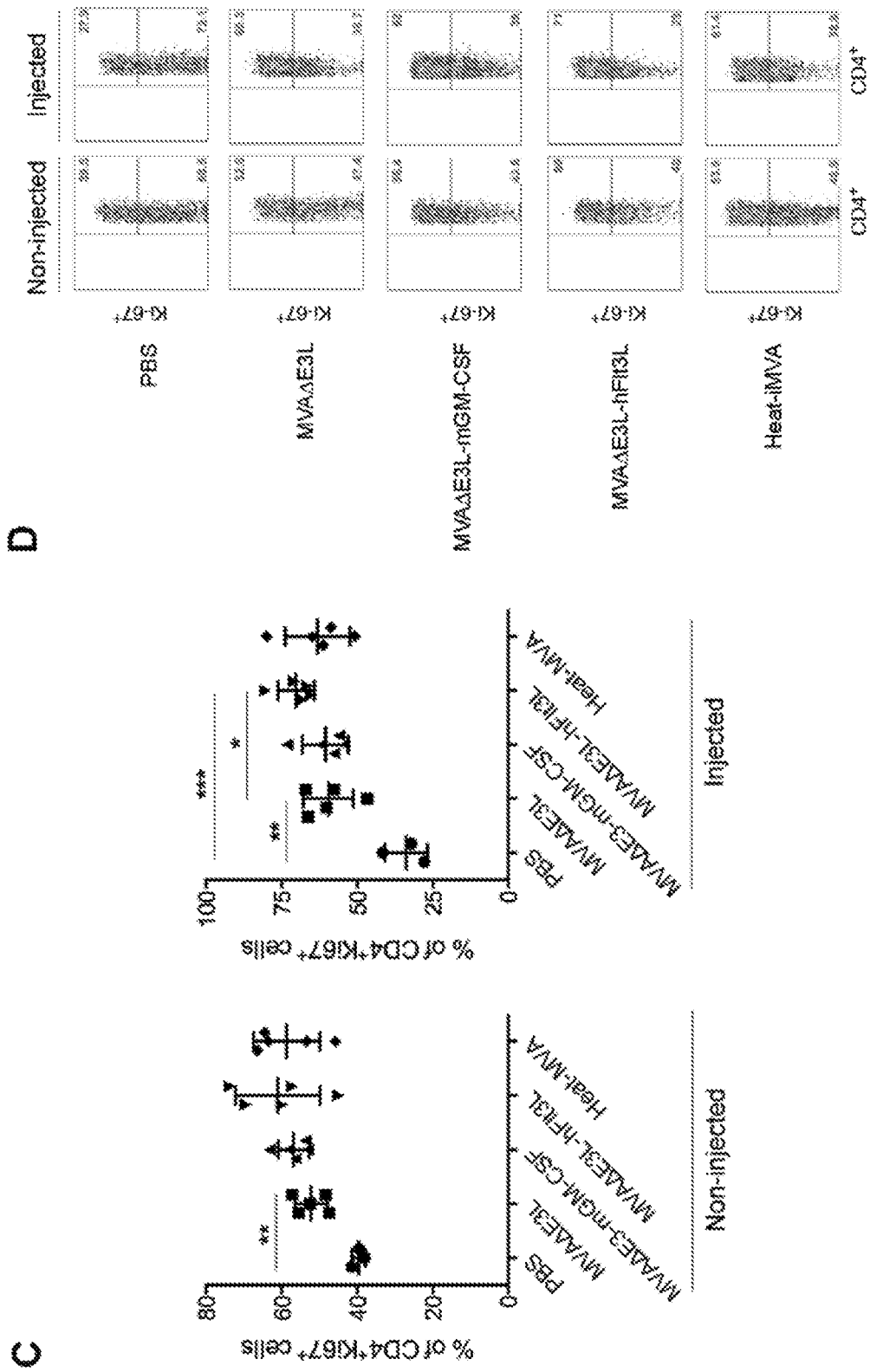
Figure 5C, D

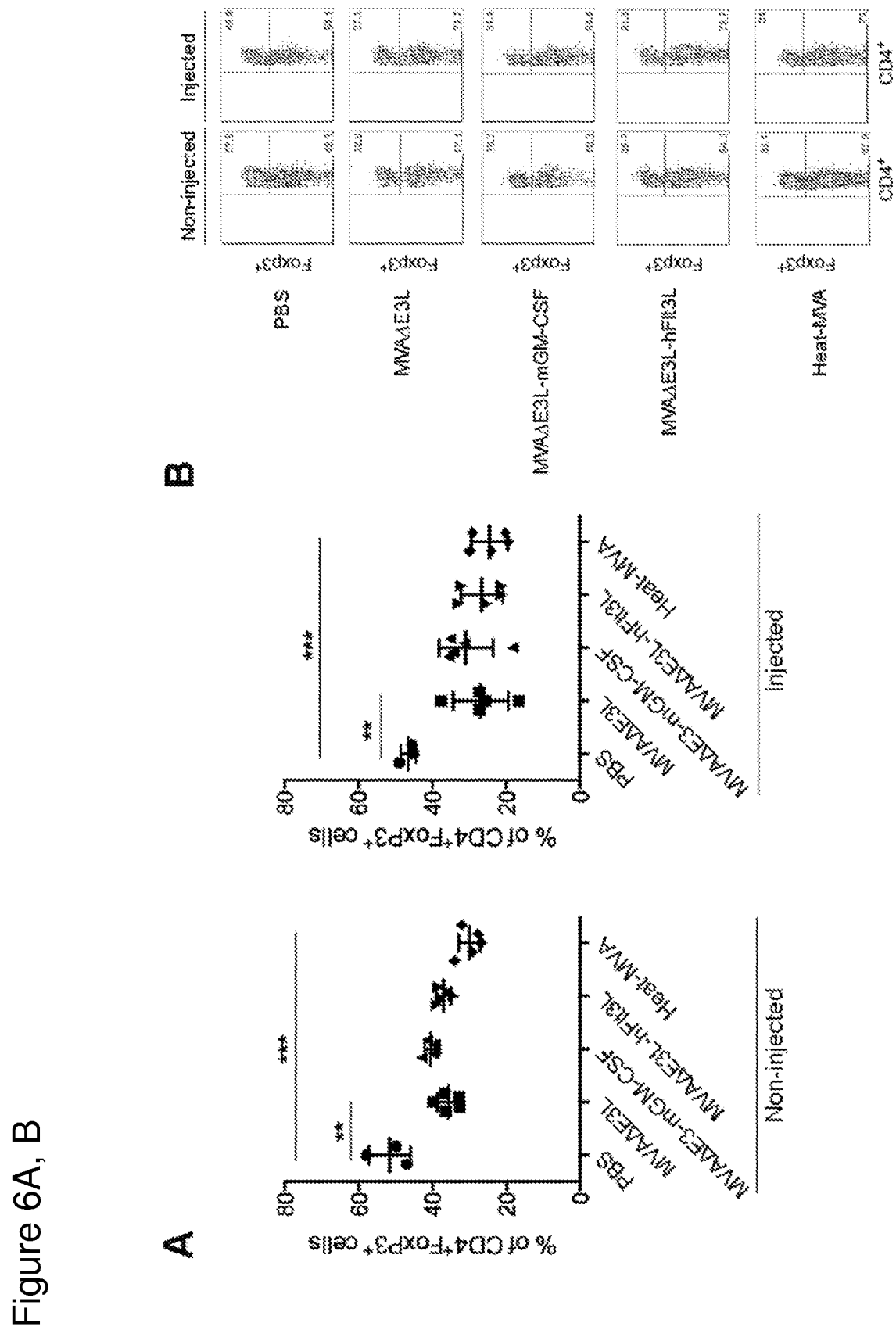
Figure 6A, B

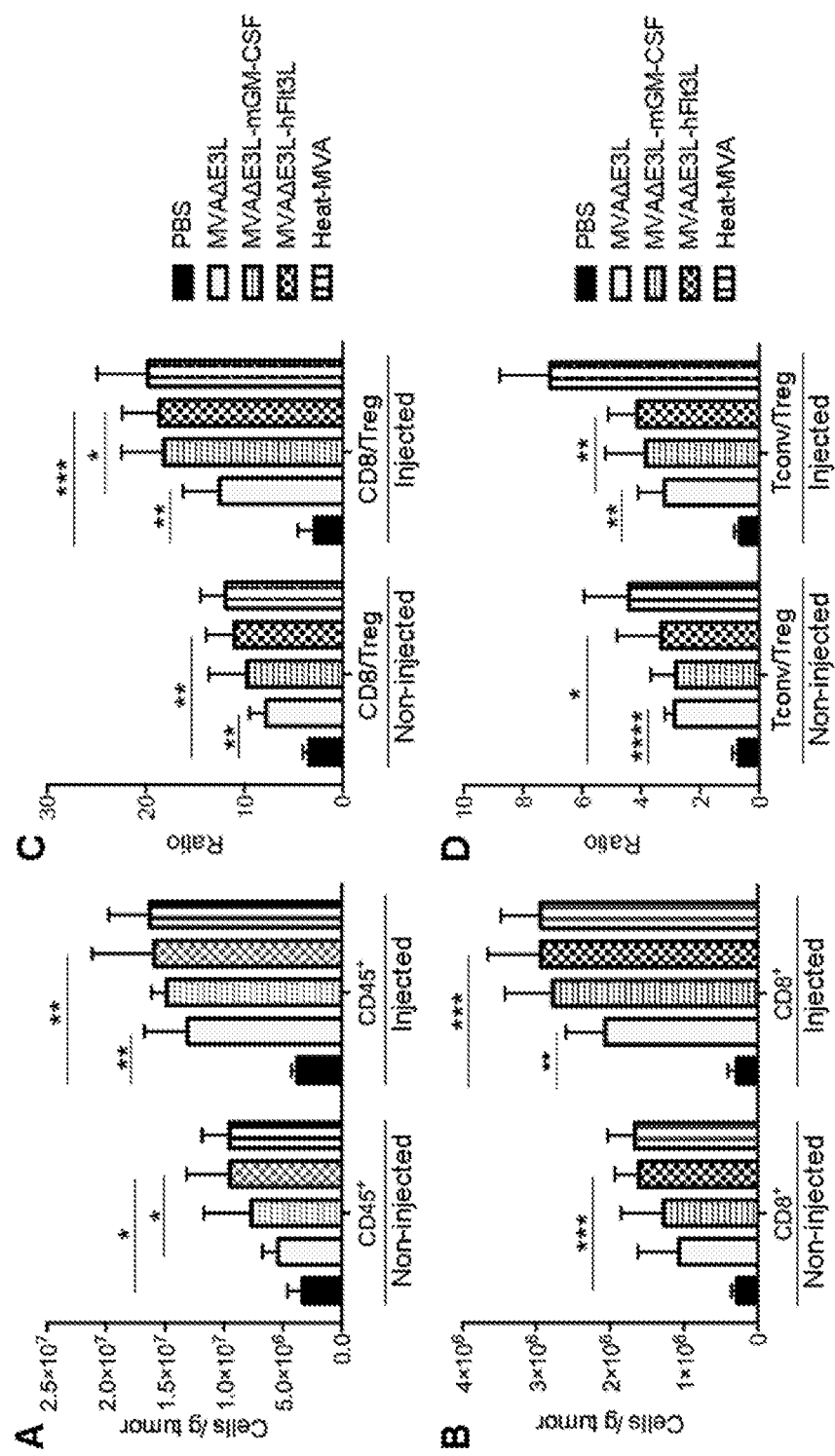
Figure 7A, B, C, D

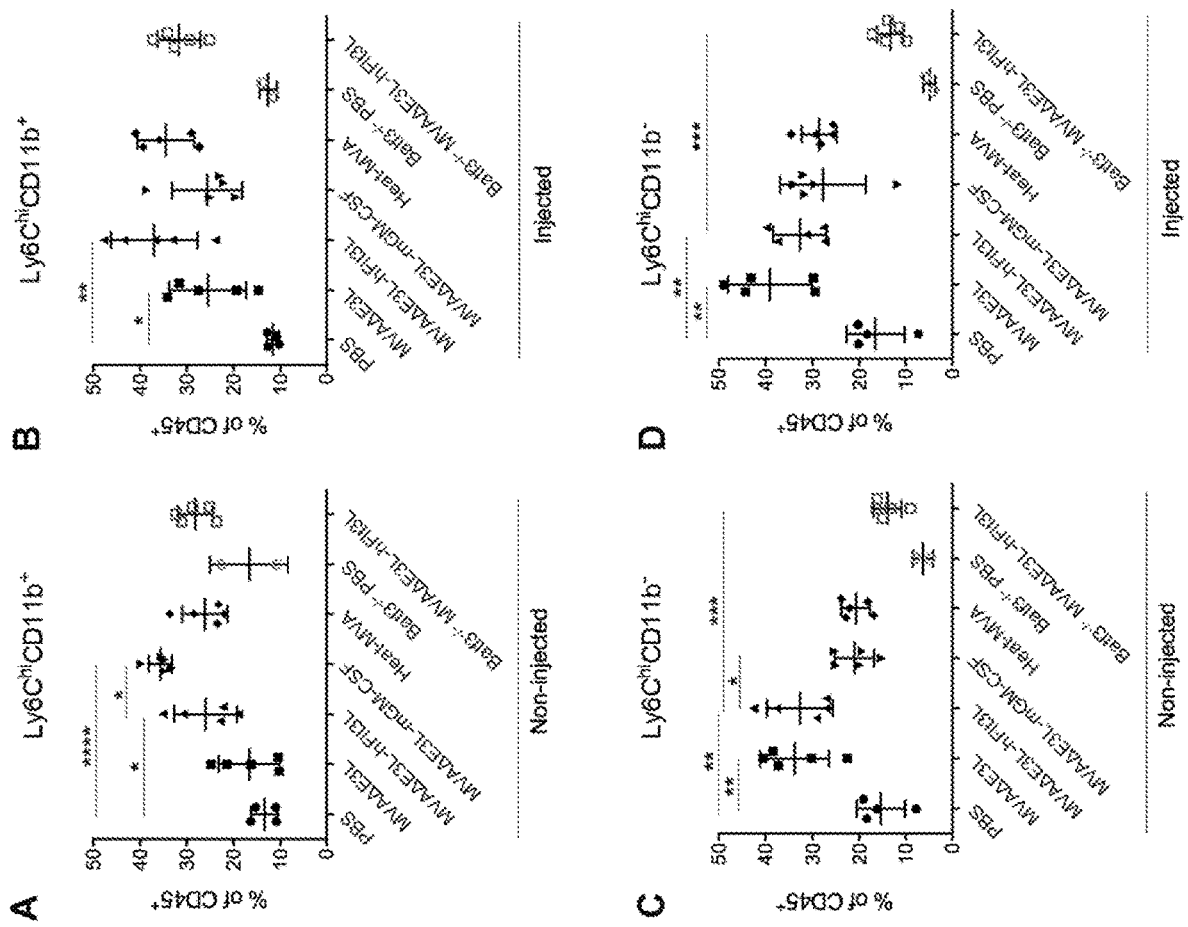
Figure 13A, B, C, D

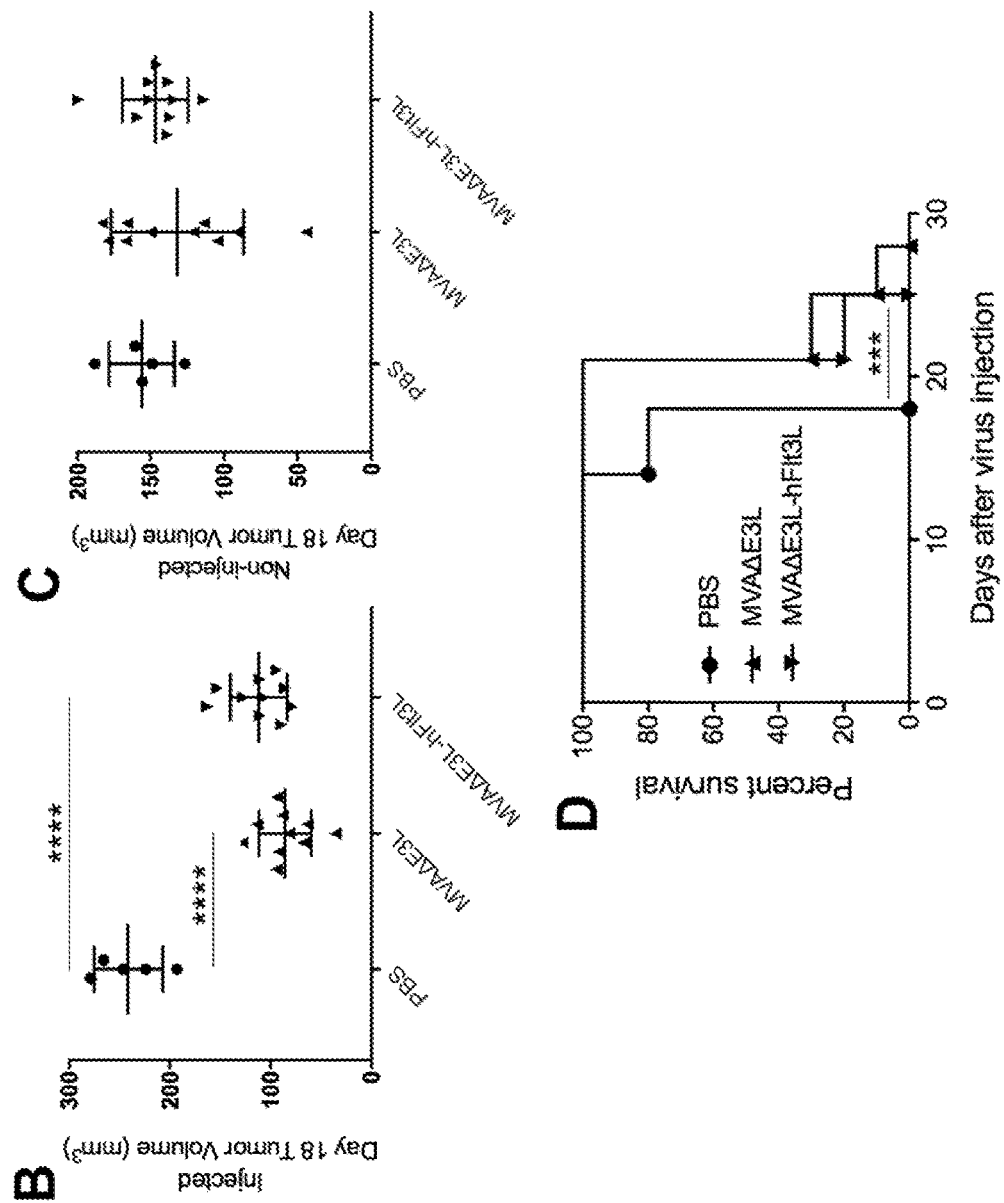
Figure 15 (B, C, and D)

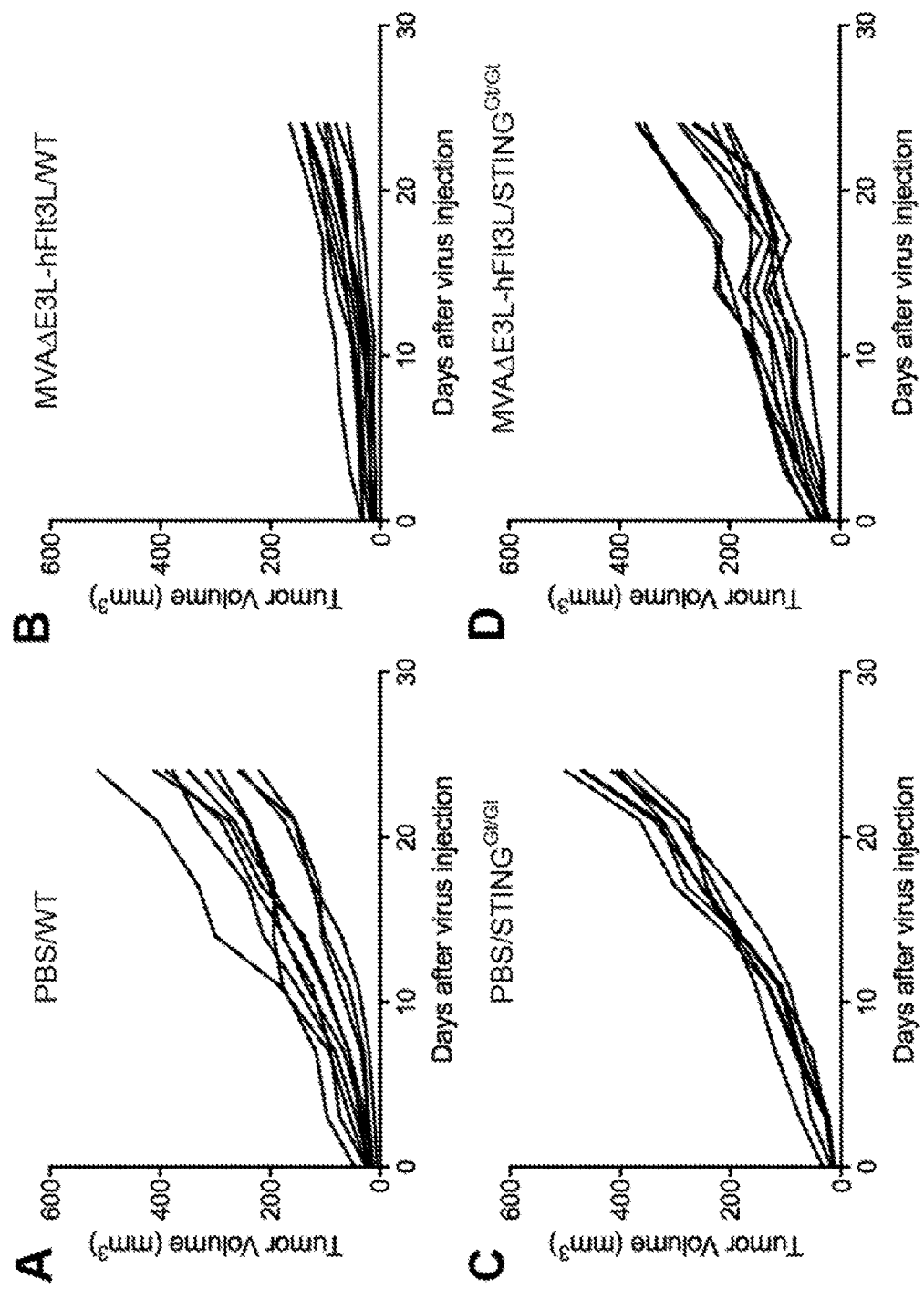
Figure 16 (A, B, C, and D)

Figure 16 (E, F)
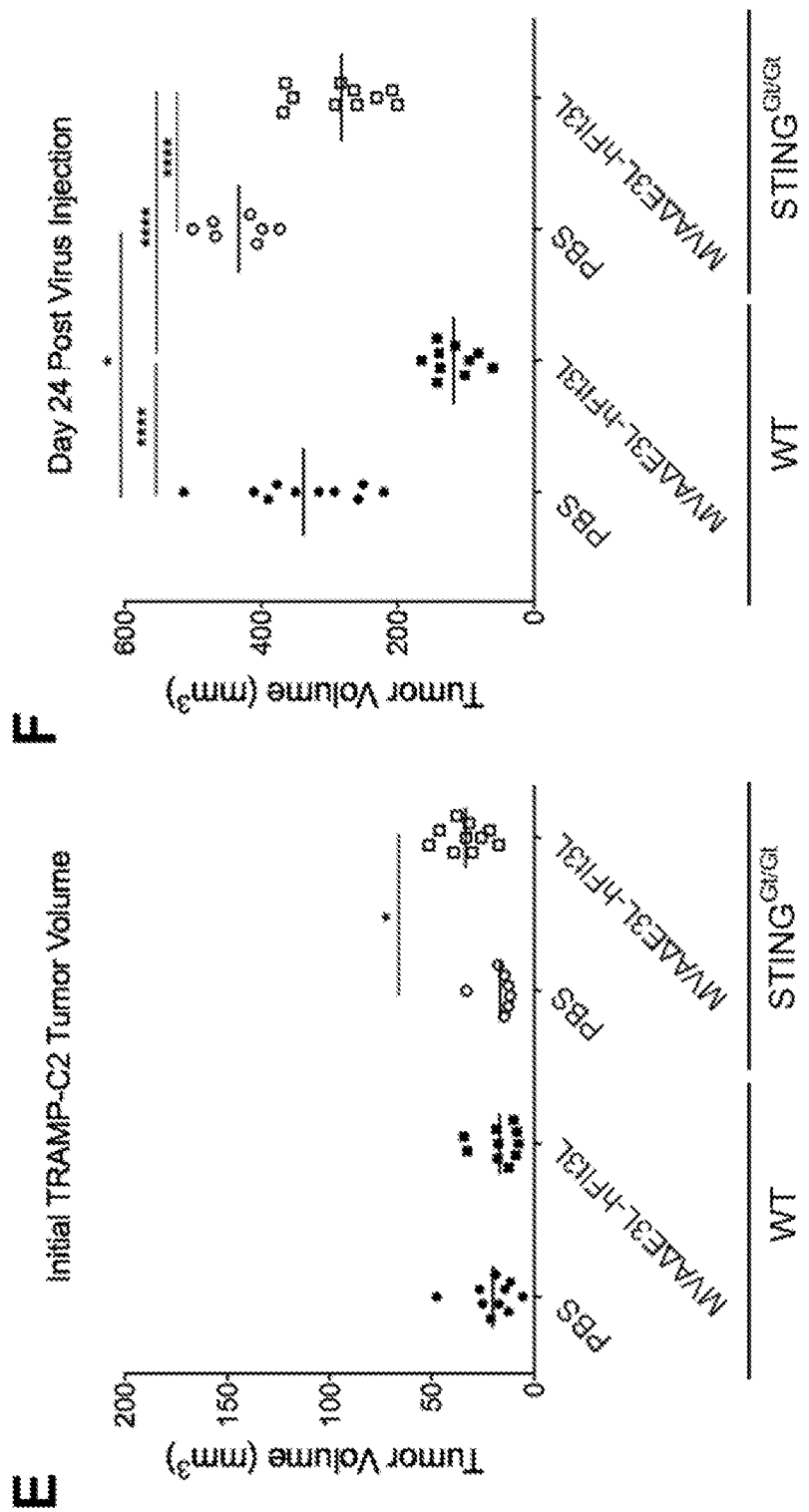

Figure 18 A, B
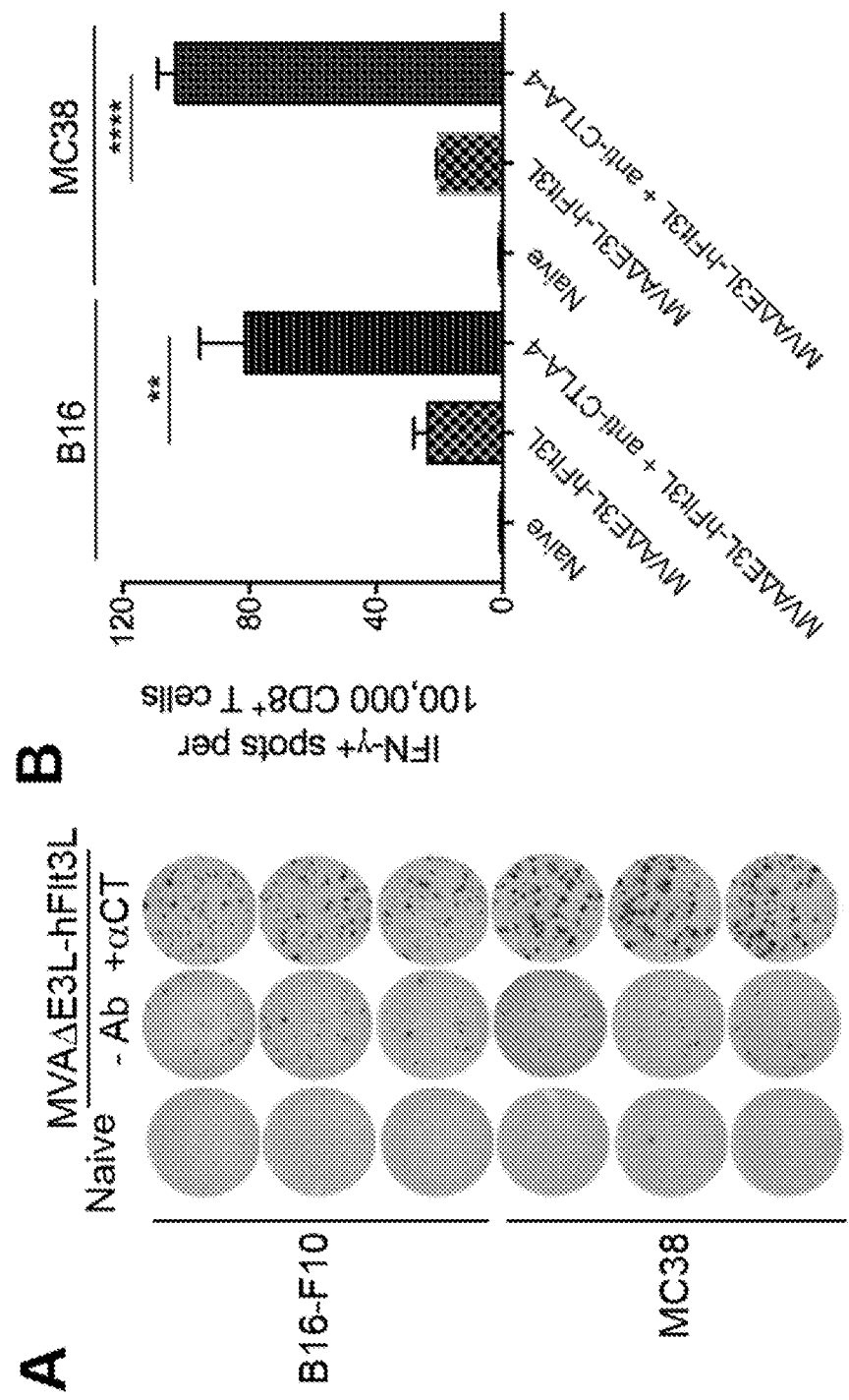

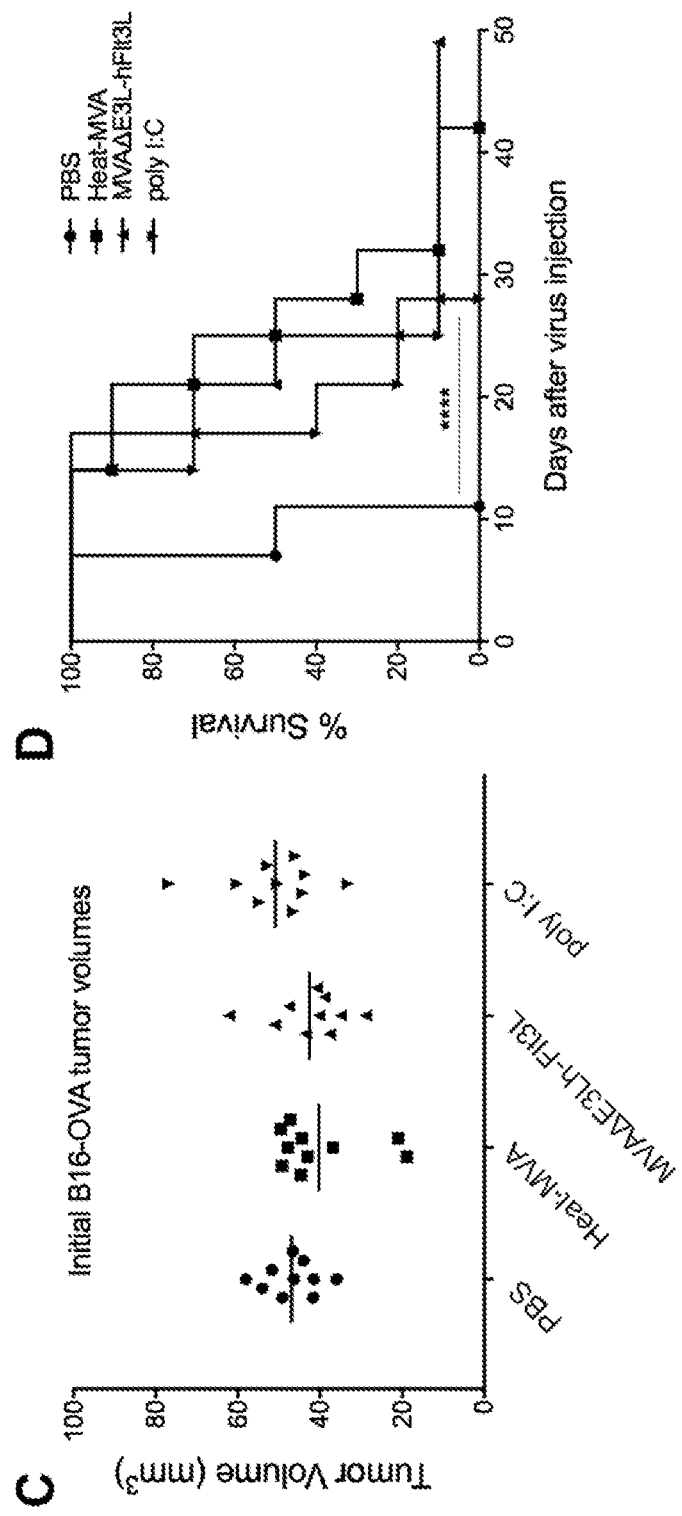
Figure 21 C, D

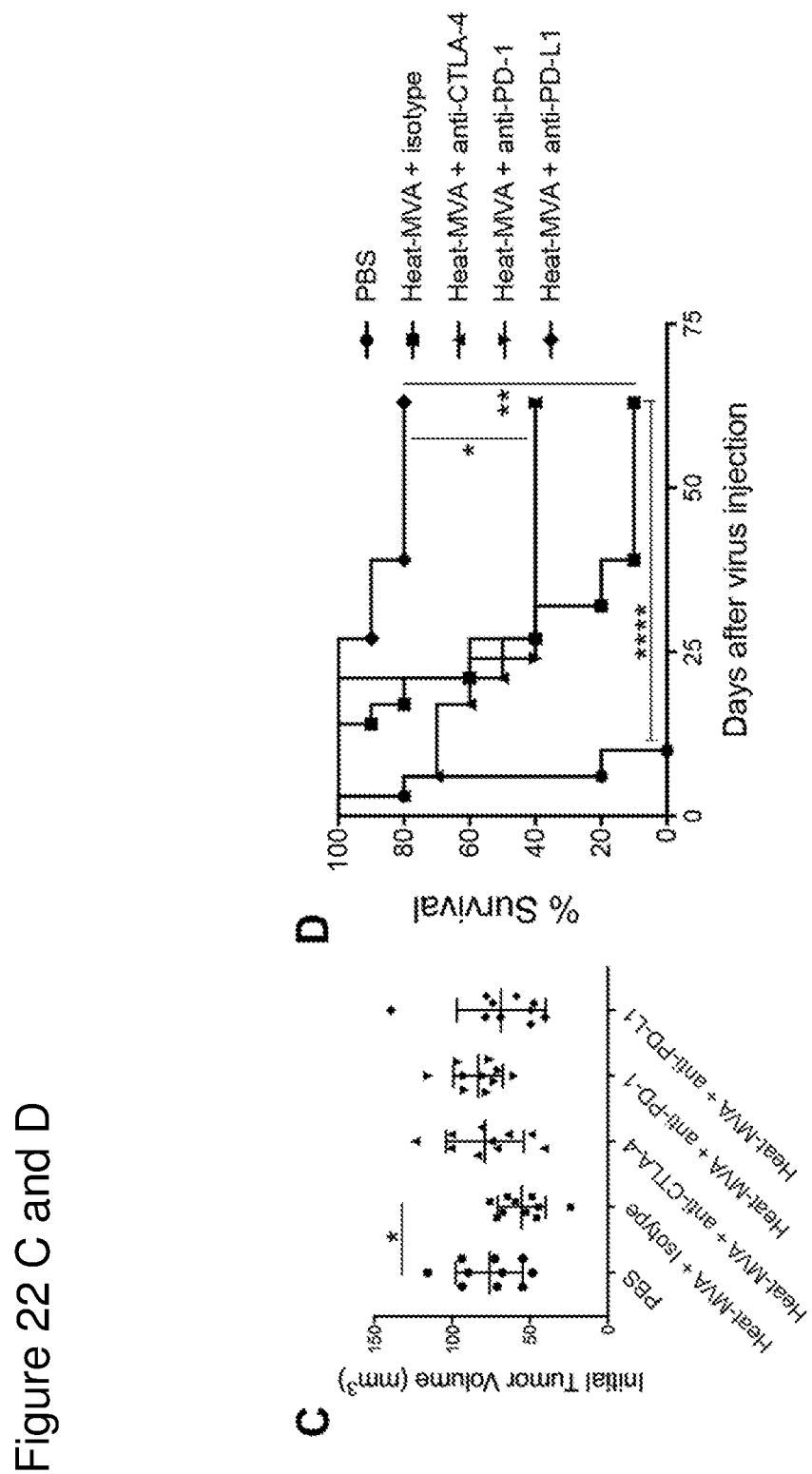
Figure 22 C and D

RECOMBINANT MVA OR MVADELE3L EXPRESSING HUMAN FLT3L AND USE THEREOF AS IMMUNO-THERAPEUTIC AGENTS AGAINST SOLID TUMORS

RELATED APPLICATIONS

This application is a U.S. National Stage Application of International Application No. PCT/US2017/019549, filed Feb. 25, 2017, which claims the benefit of and priority to U.S. Provisional Application No. 62/300,066 filed Feb. 25, 2016; U.S. Provisional Application No. 62/418,786, filed Nov. 7, 2016; and U.S. Provisional Application No. 62/418,788, filed Nov. 8, 2016, the entire disclosures of each of which are incorporated herein by reference.

GOVERNMENT SUPPORT

This invention was made with government support under grants AI073736, AI095692, CA008748 and CA56821 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 23, 2017, is named 11000_005154-WO2_SL.txt and is 2,683 bytes in size.

FIELD OF THE INVENTION

The present disclosure relates generally to the fields of oncology, virology and immunotherapy. It concerns poxviruses, specifically the highly attenuated modified vaccinia virus Ankara (MVA), and a recombinant modified vaccinia Ankara virus with deletion of vaccinia virulence factor E3 (MVAΔE3L), each further modified to express human Fms-like tyrosine kinase 3 ligand (Flt3L) or GM-CSF. The disclosure relates to use of the foregoing recombinant viruses as cancer immunotherapeutic agents. The foregoing recombinant poxviruses can also be used in combination with immune checkpoint blockade therapy.

BACKGROUND

Immune System and Cancer

Malignant tumors are inherently resistant to conventional therapies and present significant therapeutic challenges. Immunotherapy has become an evolving area of research and an additional option for the treatment of certain types of cancers. The immunotherapy approach rests on the rationale that the immune system may be stimulated to identify tumor cells, and target them for destruction.

Numerous studies support the importance of the differential presence of immune system components in cancer progression (1) (Jochems et al., *Exp Biol Med*, 236(5): 567-579 (2011)). Clinical data suggest that high densities of tumor-infiltrating lymphocytes are linked to improved clinical outcome (2) (Mlecnik et al., *Cancer Metastasis Rev.;* 30: 5-12, (2010). The correlation between a robust lymphocyte infiltration and patient survival has been reported in various types of cancer, including melanoma, ovarian, head and neck, breast, urothelial, colorectal, lung, hepatocellular, gallbladder, and esophageal cancer (3) (Angell et al., *Current Opinion in Immunology,* 25:1-7, (2013)). Tumor immune infiltrates include macrophages, dendritic cells (DC), monocytes, neutrophils, natural killer (NK) cells, nave and memory lymphocytes, B cells and effector T cells (T lymphocytes), primarily responsible for the recognition of antigens expressed by tumor cells and subsequent destruction of the tumor cells by cytotoxic T cells.

Despite presentation of antigens by cancer cells and the presence of immune cells that could potentially react against tumor cells, in many cases the immune system does not get activated or is affirmatively suppressed. Key to this phenomenon is the ability of tumors to protect themselves from immune response by coercing cells of the immune system to inhibit other cells of the immune system. Tumors develop a number of immunomodulatory mechanisms to evade anti-tumor immune responses. For example, tumor cells secrete immune inhibitory cytokines (such as TGF-β) or induce immune cells, such as CD4$^+$ T regulatory cells and macrophages, in tumor lesions to secrete these cytokines. Tumors have also the ability to bias CD4$^+$ T cells to express the regulatory phenotype. The overall result is impaired T-cell responses and impaired induction of apoptosis or reduced anti-tumor immune capacity of CD8$^+$ cytotoxic T cells. Additionally, tumor-associated altered expression of MHC class I on the surface of tumor cells makes them 'invisible' to the immune response (4) (Garrido et al. *Cancer Immunol. Immunother.* 59(10), 1601-1606 (2010)). Inhibition of antigen-presenting functions and dendritic cell (DC) additionally contributes to the evasion of anti-tumor immunity (5) (Gerlini et al. *Am. J. Pathol.* 165(6), 1853-1863 (2004)).

Moreover, the local immunosuppressive nature of the tumor microenvironment, along with immune editing, can lead to the escape of cancer cell subpopulations that do not express the target antigens. Thus, finding an approach that would promote the preservation and/or restoration of anti-tumor activities of the immune system would be of considerable therapeutic benefit.

Immune checkpoints have been implicated in the tumor-mediated downregulation of anti-tumor immunity and used as therapeutic targets. It has been demonstrated that T cell dysfunction occurs concurrently with an induced expression of the inhibitory receptors, CTLA-4 and programmed death 1 polypeptide (PD-1), members of the CD28 family of receptors. PD-1 is an inhibitory member of the CD28 family of receptors that in addition to PD-1 includes CD28, CTLA-4, ICOS and BTLA. However, while promise regarding the use of immunotherapy in the treatment of melanoma has been underscored by the clinical use and even regulatory approval of anti-CTLA-4 (ipilimumab) and anti-PD-1 drugs (for example pembrolizumab and nivolumab) the response of patients to these immunotherapies has been limited. Recent clinical trials, focused on blocking these inhibitory signals in T cells (e.g., CTLA-4, PD-1, and the ligand of PD-1 PD-L1), have shown that reversing T cell suppression is critical for successful immunotherapy (6, 7) (Sharma et al., *Science* 348(6230), 56-61 (2015); Topalian et al., *Curr Opin Immunol.* 24(2), 202-217 (2012)). These observations highlight the need for development of novel therapeutic approaches for harnessing the immune system against cancer.

Poxviruses

Poxviruses, such as engineered vaccinia viruses, are in the forefront as oncolytic therapy for metastatic cancers (8) (Kirn et al., *Nature Review Cancer* 9, 64-71 (2009)). Vaccinia viruses are large DNA viruses, which have a rapid life cycle and efficient hematogenous spread to distant tissues (9) (Moss, In Fields Virology (Lippincott Williams & Wilkins, 2007), pp. 2905-2946). Poxviruses are well-suited as vectors to express multiple transgenes in cancer cells and thus to enhance therapeutic efficacy (10) (Breitbach et al., *Current pharmaceutical biotechnology* 13, 1768-1772 (2012)). Preclinical studies and clinical trials have demonstrated efficacy of using oncolytic vaccinia viruses and other poxviruses for treatment of advanced cancers refractory to conventional therapy (11-13) (Park et al., *Lacent Oncol* 9, 533-542 (2008); Kim et al., *PLoS Med* 4, e353 (2007); Thorne et al., *J Clin Invest* 117, 3350-3358 (2007)). Poxvirus-based oncolytic therapy has the advantage of killing cancer cells through a combination of cell lysis, apoptosis, and necrosis. It also triggers innate immune sensing pathway that facilitates the recruitment of immune cells to the tumors and the development of anti-tumor adaptive immune responses. The current oncolytic vaccinia strains in clinical trials (JX-594, for example) are replicative strains. They use wild-type vaccinia with deletion of thymidine kinase to enhance tumor selectivity, and with expression of transgenes such as granulocyte macrophage colony stimulating factor (GM-CSF) to stimulate immune responses (10) (Breitbach et al., *Curr Pharm Biotechnol* 13, 1768-1772 (2012)). Many studies have shown however that wild-type vaccinia has immune suppressive effects on antigen presenting cells (APCs) (14-17) (Engelmayer et al., *J Immunol* 163, 6762-6768 (1999); Jenne et al., *Gene therapy* 7, 1575-1583 (2000); P. Li et al., *J Immunol* 175, 6481-6488 (2005); Deng et al., *J Virol* 80, 9977-9987 (2006)), and thus adds to the immunosuppressive and immunoevasive effects of tumors themselves. By contrast, modified vaccinia virus Ankara (MVA), a highly attenuated vaccinia stain has moderate immune activating effects (18, 19) (Drillien et al., *J Gen Virol* 85, 2167-75 (2004); Dai et al., *PLoS Pathog* 10(4), e1003989 (2014) but proliferates poorly in mammalian cells and would be considered unsuitable for expression of tumor antigens or for oncolytic use. However, the present inventors found that if recombinant MVA with a transgene is provided in sufficient amounts, most of the infected cells will express the transgene.

Modified vaccinia virus Ankara (MVA) is a highly attenuated vaccinia strain that is an important vaccine vector for infectious diseases and cancers. MVA was derived from vaccinia strain through more than 570 passages in chicken embryonic fibroblasts. MVA has a 31-kb deletion of the parental vaccinia genome and is non-replicative in most mammalian cells. MVA was used in more than 120,000 people during WHO-sponsored smallpox vaccination, and was shown to be very safe for human use. Because of its safety and its ability to express foreign antigens, MVA has been investigated as a vaccine vector against HIV, tuberculosis, malaria, influenza, coronavirus and CMV, as well as cancers (20-25) (Sutter et al., *Current drug targets. Infectious disorders* 3, 263-271 (2003); Gomez et al., *Curr Gene Ther* 8, 97-120 (2008); Gomez et al., *Curr Gene Ther* 11, 189-217 (2011); Goepfert et al., *J Infect Dis* 203, 610-619 (2011); Wyatt et al., *Virology* 372, 260-272 (2008); Garcia et al., *Vaccine* 29, 8309-8316 (2011)).

The investigation of MVA as a cancer therapeutic has so far been limited to its use as a vaccine vector to express tumor antigens (26, 27) (Tagliamonte et al. *Hum Vaccin Immunother* 10, 3332-3346 (2014); Verardi et al., *Hum Vaccin Immunother* 8, 961-970 (2012)). Various tumor antigens have been expressed by MVA-based vectors, and some recombinant viruses are in various stages of clinical trials. For example, MVA-PSA-PAP expresses both prostate specific antigen (PSA) and prostate acid phosphatase (PAP) is in clinical trials for patients with metastatic prostate cancer. The recombinant virus MVA-brachyury-TRICOM expressing tumor antigen brachyury and T cell co-stimulatory molecules is also in clinical trials for patients with metastatic cancers. The recombinant virus MVA-p53 expressing p53 tumor suppressor, also in clinical trials, has been shown to be safe. Other tumor antigens that have been targeted include Her2, hMUC-1, TWIST, etc.

Although MVA is highly attenuated and moderately immunostimulatory, it retains multiple immune suppressive viral genes, including a key virulence factor, E3. MVAΔE3L, a recombinant MVA virus further attenuated by deletion of the vaccinia virulent factor E3, is unable to replicate in primary chicken embryo fibroblasts (CEFs), but retains its replication capacity in baby hamster kidney BHK-21 cells (28) (Hornemann et al., *J Virol* 77(15), 8394-07 (2003). MVAΔE3L is capable of replicating viral DNA genomes in CEFs and is deficient in viral late protein synthesis (28) (Hornemann et al., *J Virol* 77(15), 8394-07 (2003). It also induces apoptosis in CEF (28) (Hornemann et al., *J Viral* 77(15), 8394-07 (2003)). MVAΔE3L infection of HeLa cells had similar effects, with impaired viral replication, viral late gene transcription and translation (29) (Ludwig et al., *J Virol* 79(4), 2584-2596 (2005)). MVAΔE3L also induces apoptosis in HeLa cells, possibly through activating the mitochondrial pathway (29) (Ludwig et al., *J Virol* 79(4), 2584-2596 (2005)). dsRNA are produced during intermediate gene transcription, which can lead to the activation of 2'-5'-oligoadenylate synthase/RNase L and Protein Kinase R (PKR). In PKR-deficient MEFs, MVAΔE3L gains the ability to express intermediate and late proteins ((29) (Ludwig et al., *J Virol* 79(4), 2584-2596 (2005)).

One study suggests that pro-apoptotic protein Noxa plays a role in MVAΔE3L apoptosis induction (30) (Fischer et al., *Cell Death Differ* 13, 109-118 (2006)). Although an early study showed that MVAΔE3L induces higher levels of type I IFN in CEFs than MVA, the exact mechanism was not fully elucidated (28) (Hornemann et al., *J Virol* 77(15), 8394-07 (2003).

One MVAΔE3L has been described in U.S. Pat. No. 7,049,145 incorporated by reference. It is infection competent but nonreplicative in most mammalian cells including mouse and human.

This disclosure focuses on the intratumoral delivery of recombinant MVA or MVAΔE3L expressing hFlt3L as anticancer immunotherapeutic agents. Intratumoral delivery of unmodified MVA or of the deletion mutant MVAΔE3L, with neither one expressing tumor antigens, as well as intratumoral delivery of inactivated MVA elicited innate immune responses from tumor infiltrating immune cells (e.g. leukocytes), tumor cells, and tumor associated stromal cells, and lead to induction of type I IFN and proinflammatory cytokines and chemokines, which result in the alteration of the tumor immune suppressive microenvironment. See WO 2016/144564 and WO 2016/168862. Human Flt3L (Fms-like tyrosine kinase 3 ligand), a type I transmembrane protein that stimulates the proliferation of bone marrow cells, was cloned in 1994 (Lyman et al., 1994). The use of hFlt3L has been explored in various preclinical and clinical settings including stem cell mobilization in preparation for bone marrow transplantation, cancer immunotherapy such as expansion of dendritic cells, as well as a vaccine adjuvant. Recombinant human Flt3L (rhuFlt3L) has been tested in more than 500 human subjects and is bioactive, safe, and well tolerated (Fong et al., 1998; Maraskovsky et al., 2000; Shackleton et al., 2004; He et al., 2014; Anandasabapathy et al., 2015). Much progress has been recently made in the understanding of the critical role of the growth factor Flt3L in the development of DC subsets, including $CD8\alpha^+$/

CD103+ DCs and pDCs (McKenna et al., 2000; Waskow et al., 2008; Liu et al., 2007; 2009; Naik et al., 2006; Ginhoux et al., 2009).

CD103+/CD8α+ DCs have been shown to be required for spontaneous cross-priming of tumor antigen-specific CD8+ T cells (Hildner et al., 2008; Ginhoux et al., 2009, Zhang et al., 2015; Spranger et al., 2015), Broz et al. reported that CD103+ DCs are sparsely present within the tumors and they compete for tumor antigens with abundant tumor-associated macrophages. CD103+ DCs are uniquely capable in stimulating nave as well as activated CD8+ T cells and are critical for the success of adoptive T cell therapy (Broz, et al. *Cancer Cell,* 26(5):638-52, 2014). Spranger et al. reported that the activation of oncogenic signaling pathway WNT/β-catenin leads to reduction of CD103+ DCs and anti-tumor T cells within the tumors (Spranger et al., 2015). Intratumoral delivery of Flt3L-cultured BMDCs leads to responsiveness to the combination of anti-CTLA-4 and anti-PD-L1 immunotherapy (Spranger et al., 2015). Systemic administration of Flt3L, a growth factor for CD103+ DCs, and intratumor injection of poly I:C (TLR3 agonist) expanded and activated the CD103+ DC populations within the tumors and overcame resistance or enhanced responsiveness to immunotherapy in a murine melanoma and MC38 colon cancer models (Salmon et al., 2016, Sanchez-Paulete et al., 2016).

The recent discovery of tumor neoantigens in various solid tumors indicates that solid tumors harbor unique neoantigens that usually differ from person to person (31, 32) (Castle et al., *Cancer Res* 72, 1081-1091 (2012); Schumacher et al., *Science* 348, 69-74 (2015)). The recombinant viruses disclosed herein do not exert their activity by expressing tumor antigens. Intratumoral delivery of the present recombinant MVA viruses allows efficient cross-presentation of tumor neoantigens and generation of anti-tumor adaptive immunity within the tumors (and also extending systemically), and therefore leads to "in situ cancer vaccination" utilizing tumor differentiation antigens and neoantigens expressed by the tumor cells in mounting an immune response against the tumor.

Despite the presence of neoantigens generated by somatic mutations within tumors, the functions of tumor antigen-specific T cells are often held in check by multiple inhibitory mechanisms (33) (Mellman et al., *Nature* 480, 480-489 (2011)). For example, the up-regulation of cytotoxic T lymphocyte antigen 4 (CTLA-4) on activated T cells can compete with T cell co-stimulator CD28 to interact with CD80 (B71)/CD86 (B7.2) on dendritic cells (DCs), and thereby inhibit T cell activation and proliferation. CTLA-4 is also expressed on regulatory T (Treg) cells and plays an important role in mediating the inhibitory function of Tregs (34, 35) (Wing et al., *Science* 322, 271-275 (2008); Peggs, et al., *J Exp Med* 206, 1717-1725 (2009)). In addition, the expression of PD-L/PD-L2 on tumor cells can lead to the activation of the inhibitory receptor of the CD28 family, PD-1, leading to T cell exhaustion. Immunotherapy utilizing antibodies against inhibitory receptors, such as CTLA-4 and programmed death 1 polypeptide (PD-1), have shown remarkable preclinical activities in animal studies and clinical responses in patients with metastatic cancers, and have been approved by the FDA for the treatment of metastatic melanoma, non-small cell lung cancer, as well as renal cell carcinoma (6, 36-39) (Leach et al., *Science* 271, 1734-1746 (1996); Hodi et al., *NEJM* 363, 711-723 (2010); Robert et al., *NEJM* 364, 2517-2526 (2011); Topalian et al., *Cancer Cell* 27, 450-461 (2012); Sharma et al., *Science* 348(6230), 56-61 (2015)).

Melanoma

Melanoma, one of the deadliest cancers, is the fastest growing cancer in the US and worldwide. Its incidence has increased by 50% among young Caucasian women since 1980, primarily due to excess sun exposure and the use of tanning beds. According to the American Cancer Society, approximately 78,000 people in the US will be diagnosed with melanoma in 2015 and almost 10,000 people (or one person per hour) will die from melanoma. In most cases, advanced melanoma is resistant to conventional therapies, including chemotherapy and radiation. As a result, people with metastatic melanoma have a very poor prognosis, with a life expectancy of only 6 to 10 months. The discovery that about 50% of melanomas have mutations in BRAF (a key tumor-promoting gene) opened the door for targeted therapy in this disease. Early clinical trials with BRAF inhibitors showed remarkable, but unfortunately not sustainable, responses in patients with melanomas with BRAF mutations. Therefore, alternative treatment strategies for these patients, as well as others with melanoma without BRAF mutations, are urgently needed.

Human pathological data indicate that the presence of T-cell infiltrates within melanoma lesions correlates positively with longer patient survival (40) (Oble et al. *Cancer Immun.* 9, 3 (2009)). The importance of the immune system in protection against melanoma is further supported by partial success of immunotherapies, such as the immune activators IFN-α2b and IL-2 (41) (Lacy et al. *Expert Rev Dermatol* 7(1):51-68 (2012)) as well as the unprecedented clinical responses of patients with metastatic melanoma to immune checkpoint therapy, including anti-CTLA-4 and anti-PD-1/PD-L1 either agent alone or in combination therapy (6, 7, 37, 42-45) (Sharma and Allison, Science 348(6230), 56-61 (2015); Hodi et al., NEJM 363(8), 711-723 (2010); Wolchok et al., Lancet Oncol. 11(6), 155-164 (2010); Topalian et al., NEJM 366(26), 2443-2454 (2012); Wolchok et al., NEJM 369(2), 122-133 (2013); Hamid et al., NEJM 369(2), 134-144 (2013); Tumeh et al., Nature 515 (7528), 568-571 (2014). However, many patients fail to respond to immune checkpoint blockade therapy alone. The addition of virotherapy might overcome resistance to immune checkpoint blockade, which is supported by animal tumor models (46) (Zamarin et al., Sci Transl Med 6(226), 2014). However, the mechanism of overcoming this resistance is far from being well understood.

Type I IFN and the Cytosolic DNA-Sensing Pathway in Tumor Immunity.

Type I IFN plays important roles in host antitumor immunity (47) (Fuertes et al., *Trends Immunol* 34, 67-73 (2013)). IFNAR1-deficient mice are more susceptible to develop tumors after implantation of tumor cells; Spontaneous tumor-specific T cell priming is also defective in IFNAR1-deficient mice (48, 49) (Diamond et al., *J Exp Med* 208, 1989-2003 (2011); Fuertes et al., *J Exp Med* 208, 2005-2016 (2011)). More recent studies have shown that the cytosolic DNA-sensing pathway is important in the innate immune sensing of tumor-derived DNA, which leads to the development of antitumor CD8+ T cell immunity (50) (Woo et al., *Immunity* 41, 830-842 (2014)). This pathway also plays a role in radiation-induced antitumor immunity (51) (Deng et al., *Immunity* 41, 843-852 (2014)). Although spontaneous anti-tumor T cell responses can be detected in patients with cancers, cancers eventually overcome host antitumor immunity in most patients. Novel strategics to alter the tumor immune suppressive microenvironment would be beneficial for cancer therapy.

Certain steps in the direction of improving the host's immune responses to tumors have already been taken by the present inventors and their co-workers. It has been shown that intratumoral (or systemic) delivery of inactivated MVA induces antitumor immunity attributable to activation of cellular immune responses, innate and adaptive, and involving induction of Type I IFN and that this activation overcomes tumor immunity and leads to reduction even eradication of solid tumors. See International (PCT) Patent Application filed on Feb. 25, 2016 and published on Sep. 15, 2016 as WO 2016/144564, incorporated by reference in its entirety. Additionally, the same group of investigators have shown that intratumoral or systemic delivery of MVA and/or MVAΔE3L, expressing no transgene, also induces antitumor immunity attributable to similar activation of cellular responses and involving induction of Type I IFN and leading to reduction even eradication of solid tumors such as melanoma. See International (PCT) Patent Application filed on Apr. 18, 2016 and published on Oct. 20, 2016 as WO 2016/168862, incorporated by reference in its entirety. Nevertheless, the effort to improve the ability of the immune system of subjects afflicted with malignant tumors is ongoing.

SUMMARY

In one aspect, the present disclosure is directed to a composition comprising a recombinant modified vaccinia Ankara (MVA) virus selected from the group consisting of (i) MVA harboring a human Fms-like tyrosine kinase 3 ligand (hFlt3L) (MVA-hFtl3L); and (ii) MVAΔE3L harboring hFlt3L (MVAΔE3L-hFtl3L) in an amount effective, upon delivery to tumor cells of a subject afflicted with a malignant solid tumor, to treat the tumor. In a related aspect, the present disclosure is directed to recombinant modified vaccinia Ankara virus with deletion of vaccinia virulence factor E3 (MVAΔE3L) modified to express human Fms-like tyrosine kinase 3 ligand (hFlt3L) isolated, suitable for use as an immunotherapeutic agent against a malignant solid tumor.

In some embodiments, the treatment of the tumor is manifest by one or more of the following: induction, in the subject of an immune response against the tumor or enhancement or promotion in the subject of an ongoing immune response against the tumor, reduction of the size of the tumor, eradication of the tumor, inhibition of growth of the tumor, inhibition of metastasis of the tumor, and reduction or eradication of metastatic tumor.

In more specific embodiments, the induction, enhancement or promotion of the immune response comprises one or more of the following:
proliferation and activation of CD8$^+$ cytotoxic T cells;
proliferation and activation of CD4$^+$ effector T cells;
increase of the ratio of CD8$^+$/Treg and of Tconv/Treg;
recruitment of CD45$^+$ cells and CD8$^+$ T cells in the injected and distant tumors;
reduction of tumor-associated macrophages (TAM) in the injected and distant tumors;
influx of Ly6C$^{hi}$CD11b$^+$ inflammatory monocytes and Ly6C$^{hi}$CD11b$^-$ myeloid cells into the injected and distant tumors; and
activation and mobilization of cross-presenting CD103$^+$ dendritic cells in the injected and distant tumors via the production of type IFN and proinflammatory cytokines.
generation of anti-tumor CD8$^+$ T cells and cross-protection against heterologous tumor(s)

In some embodiments, the recombinant MVA is not harboring nucleic acid encoding or expressing a tumor antigen. In further embodiments, the composition further comprises one or more pharmaceutically acceptable excipients.

In some embodiments, one or more excipients is selected from the group consisting of solvents, dispersion media, coatings, antibacterial and antifungal agents, isotonic agents, absorption delaying agents and combinations of two or more of the foregoing.

In further embodiments, the recombinant MVA comprises MVAΔE3L-hFlt3L.

In one aspect, the composition further comprises a second amount of a replication competent recombinant attenuated vaccinia virus with deletion of thymidine kinase encoding and expressing human Flt3L, wherein the second amount contributes to augmenting the induced or enhanced or promoted immune response. In another aspect, the composition further comprises a third amount of inactivated MVA wherein the third amount contributes to augmenting the induced or enhanced or promoted immune response.

In some embodiments, the present disclosure relates to a method for treating a subject afflicted with a malignant solid tumor, the method comprising delivering to the cells of the tumor a recombinant MVA virus selected from the group of MVA-hFlt3L and MVAΔE3L-hFlt3L and combinations thereof and thereby treating the tumor. In one embodiment, the amount of said virus is effective to bring about one or more of the following: induce the immune system of the subject to mount an immune response against the tumor or enhance or promote an ongoing immune response by the immune system against the tumor; reduce the size of the tumor; eradicate the tumor; inhibit growth of the tumor; inhibit metastasis of the tumor; and reduce or eradicate metastatic tumor. In some embodiments, the immune response against the tumor accomplishes one or more of the following:
proliferation and activation of CD8$^+$ cytotoxic T cells;
proliferation and activation of CD4$^+$ effector T cells;
increase of the ratio of CD8$^+$/Treg and of Tconv/Treg;
recruitment of CD45$^+$ cells and CD8$^+$ T cells in the injected and distant tumors;
reduction of tumor-associated macrophages (TAM) in the injected and distant tumors;
influx of Ly6C$^{hi}$CD11b$^-$ inflammatory monocytes and Ly6C$^{hi}$CD11b$^-$ myeloid cells into the injected and distant tumors; and
activation and mobilization of cross-presenting CD103$^+$ dendritic cells in the injected and distant tumors via the production of type IFN and proinflammatory cytokines.
generation of anti-tumor CD8$^+$ T cells and cross-protection against heterologous tumor(s)

In further embodiments, said MVA or MVAΔE3L is not harboring nucleic acid encoding or expressing a tumor antigen.

In some embodiments, the recombinant MVA is delivered by intratumoral or intravenous injection or a simultaneous or sequential combination of intratumoral and intravenous injection.

In some embodiments, the tumor is melanoma or colon carcinoma or breast carcinoma or prostate carcinoma.

In some embodiments, treatment with MVAΔE3L-hFlt3L of a subject afflicted with one type of solid tumor demonstrates protection against an unrelated type of tumor, demonstrating that the immunotherapeutic agent of the present disclosure elicits antitumor activity targeting tumors from different origins.

In yet further embodiments, delivery of the recombinant MVA is continued for several weeks, months or years or indefinitely, as long as benefits persist or a maximum tolerated dose is reached. In some embodiments, delivery of the recombinant MVA is by intratumoral injection.

In some embodiments, the subject is a human.

In other embodiments, the recombinant MVA is delivered at a dosage per administration within the range of about $10^6$-$10^{10}$ plaque-forming units (pfu), preferably within the range of about $10^7$ to about $10^9$ plaque-forming units (pfu). In some embodiments, the amount delivered is sufficient to infect all tumor cells. In some embodiments, the delivery is repeated with a frequency within the range from once per month to two times per week. In further embodiments, the delivery is repeated once weekly.

In some embodiments, the melanoma is metastatic melanoma.

In some embodiments, the recombinant MVA is MVAΔE3L-hFlt3L.

In another aspect, the present disclosure relates to a method for treating a solid malignant tumor in a subject comprising delivering to a tumor of the subject an amount of recombinant modified vaccinia virus Ankara (MVA) selected from the group consisting of MVA-hFlt3L, MVAΔE3L-hFlt3L or a combination of both, effective to bring about at least one of the following immunologic effects: proliferation and activation of $CD8^+$ cytotoxic T cells;
  proliferation and activation of $CD8^+$ cytotoxic T cells;
  proliferation and activation of $CD4^+$ effector T cells;
  increase of the ratio of $CD8^+$/Treg and of Tconv/Treg;
  recruitment of $CD45^+$ cells and $CD8^+$ T cells in the injected and distant tumors;
  reduction of tumor-associated macrophages (TAM) in the injected and distant tumors;
  influx of $Ly6C^{hi}CD11b^+$ inflammatory monocytes and $Ly6C^{hi}CD11b^-$ myeloid cells into the injected and distant tumors; and
  activation and mobilization of cross-presenting $CD103^+$ dendritic cells in the injected and distant tumors via the production of type IFN and proinflammatory cytokines.
  generation of anti-tumor $CD8^+$ T cells and cross-protection against heterologous tumor(s)

In another aspect, the present disclosure relates to a method for treating a solid malignant tumor in a subject comprising delivering to tumor cells of the subject MVA-hFlt3L or MVAΔE3L-hFlt3L or a combination thereof in an amount effective to induce the immune system of the subject to mount an immune response against the tumor or to enhance or promote an ongoing immune response of said subject against the tumor, so as to accomplish one or more of the following: reduce the size of the tumor, eradicate the tumor, inhibit growth of the tumor, inhibit metastatic growth of the tumor, induce apoptosis of tumor cells or prolong survival of the subject.

In yet another aspect, the present disclosure relates to a method for treating a malignant tumor in a subject, the method comprising delivering to tumor cells of the subject a virus selected from the group consisting of MVA-hFlt3L, MVAΔE3L-hFlt3L and a combination thereof in an amount effective to induce the immune system of the subject to mount an immune response against the tumor or to enhance or promote an ongoing immune response of said subject against the tumor and conjointly administering to the subject a second amount of an immune checkpoint blocking agent or an immune checkpoint agonist effective to block immune suppressive mechanisms within the tumor.

In one embodiment, the administration of the checkpoint inhibitor or checkpoint agonist is by parenteral route. In one embodiment, the delivery is by intratumoral injection and the administration is by intravenous route. In another embodiment, both the delivery and the administration are by intravenous route. In some embodiments, both the delivery and the administration are by intratumoral injection.

In some embodiments the conjoint administration enhances effector T-cell responses; in some embodiments, the conjoint administration enhances memory T cell responses. In some embodiments, the conjoint administration significantly increases survival, achieves at least, inhibition of growth of the tumor including metastatic tumor compared to either monotherapy, In some embodiments, the immune checkpoint blocking agent is selected from the group consisting of PD-1 inhibitors, PD-L1 inhibitors, CTLA4 inhibitors, inhibitory antibodies against LAG-3 (lymphocyte activation gene 3), TIM3 (T cell Immunoglobulin and Mucin-3), B7-H3, and TIGIT (T-cell immunoreceptor with Ig and ITIM domains); and the immune checkpoint agonist is selected from the group consisting of anti-ICOS antibody anti-OX40 antibody agonist antibody against 4-IBB (CD 137) and against GITR.

In one embodiment, the tumor is primary or metastatic melanoma or primary or metastatic colon carcinoma. In another embodiment, the virus is delivered and the immune checkpoint blocking agent is administered each according to its own administration schedule of spaced apart intervals.

In one embodiment, a first dose of the virus is delivered first and after a lapse of time a first dose of the immune checkpoint blocking agent is administered.

In a further embodiment, the delivery and administration occur in parallel during the same overall period of time. In some embodiments, one or both of the virus and the immune checkpoint blocking agent are respectively delivered and administered during a period of time of several weeks, months or years, or indefinitely as long as benefits persist and a maximum tolerated dose is not reached.

In some embodiments, the virus and the immune checkpoint blocking agent are administered simultaneously. In further embodiments, the virus and the immune checkpoint blocking agent are administered in the same composition.

In some embodiments, the recombinant MVA and the immune checkpoint blocking agent are delivered intratumorally. In further embodiments, the recombinant MVA and the immune checkpoint blocking agent are administered sequentially.

In more specific embodiments, the method further comprises administering to the subject a replication competent recombinant attenuated vaccinia virus with deletion of thymidine kinase encoding and expressing human Flt3L, or inactivated MVA, or both, respectively in a second and third amount, said second amount or third amount or both contributing to augmenting the induced or enhanced or promoted immune response.

In one aspect, the present disclosure relates to a kit comprising: 1) A first component comprising a composition according the present disclosure;
2) a second component comprising one or both of a replication competent recombinant attenuated vaccinia virus with deletion of thymidine kinase encoding and expressing human Flt3L, and inactivated MVA, respectively in a second and third amount, said second amount or third amount or both second and third amount contributing to augmenting the induced or enhanced or promoted immune response in said subject.

An interesting result of the present method is that the intratumoral injection of virus results in anti-tumor immunity against a different solid tumor.

In the present disclosure, the inventors explored whether MVA-hFlt3L or MVAΔE3L-hFlt3L strain can be used as cancer immunotherapeutic agent. In fact, they observed that intratumoral delivery of MVAΔE3L-hFlt3L is more efficacious in eradiating tumors and generating antitumoral immunity than MVAΔE3L. Similarly, intratumoral delivery of MVA-hFlt3L is more efficacious in eradiating tumors and generating antitumoral immunity than MVA. Thus, as a treatment option, patients can be treated with MVA-hFlt3L or MVAΔVE3L-hFlt3L or both in order to achieve improved treatment results.

In view of similarities shown here between MVA-hFlt3L and MVAΔE3L-hFlt3L, it is anticipated that properties and advantages observed for MVAΔE3L-hFlt3L compared to MVAΔE3L that lacks hFlt3L are also exhibited by MVA-hFlt3L compared to MVA alone.

BRIEF DESCRIPTION OF THE DRAWINGS

FIG. 4 is a series of graphical representations of data collected after intratumoral injection of MVAΔE3L-hFlt3L demonstrating that it is effective in inducing proliferation and activation of $CD8^+$ T cells in both injected and non-injected tumors in a bilateral melanoma model. (A) consists of two plots of the percentage of $CD8^+$ Granzyme $B^+$ cells in injected (right plot) and non-injected (left plot) tumors of mice treated variously with PBS, MVAΔE3L, MVAΔE3L-mGM-CSF, MVAΔE3L-hFlt3L, or, as a positive control, heat-inactivated MVA (Heat-MVA) (*, $p<0.05$, , $p<0.01$, *, $p<0.001$). Data are means±SEM (n=3 for PBS group and n=5 for each virus group). (B) is a series of representative flow cytometry plots of $CD8^+$ cells expressing Granzyme B in injected and non-injected tumors. (C) consists of two plots of the percentage of $CD8^+$ Ki-$67^+$ cells in injected (right) and non-injected (left) tumors of mice treated variously with PBS, MVAΔE3L, MVAΔE3L-mGM-CSF, MVAΔE3L-hFlt3L or Heat-MVA (, $p<0.01$, *, $p<0.001$). Data are means±SEM (n=3 for PBS group and n=5 for each virus group). (D) is a series of representative flow cytometry plots of $CD8^+$ cells expressing Ki-67 in injected and non-injected tumors.

FIG. 5 is a series of graphical representations of data collected after intratumoral injection of MVAΔE3L-hFlt3L demonstrating that it is effective in inducing proliferation and activation of $CD4^+$ T cells in both injected and non-injected tumors. (A) consists of two plots of the percentage of $CD4^+$ Granzyme $B^+$ cells in injected and non-injected tumors of mice treated with PBS, MVAΔE3L, MVAΔE3L-mGM-CSF, MVAΔE3L-hFlt3L, or Heat-MVA (*, $p<0.05$, , $p<0.01$, , $p<0.0001$). Data are means±SEM (n=3 for PBS group and n=5 for each virus group). (B) is a series of representative flow cytometry plots of $CD4^+$ cells expressing Granzyme B in injected and non-injected tumors. (C) consists of two plots of percentage of $CD4^+$ Ki-$67^+$ cells in injected (right plot) and non-injected (left plot) tumors (, $p<0.01$, ***, $p<0.001$). Data are means±SEM (n=3 for PBS group and n=5 for each virus group). (D) is a series of representative flow cytometry plots of $CD4^+$ cells expressing Ki-67 in injected and non-injected tumors.

FIG. 6 is a series of graphical representations of data collected after intratumoral injection of MVAΔE3L-hFlt3L showing that it is effective in inducing reduction of $CD4^+$ $FoxP3^+$ regulatory T cells in both injected and non-injected tumors. (A) consists of two plots of the percentage of $CD4^+$ $FoxP3^+$ cells in injected and non-injected tumors of a bilateral mouse model treated with PBS, MVAΔE3L, MVAΔE3L-mGM-CSF, MVAΔE3L-hFlt3L, or Heat-MVA (, $p<0.01$, **, $p<0.0001$). Data are means±SEM (n=3 for PBS group and n=5 for each virus group). (B) is a series of representative flow cytometry plots of $CD4^+$ cells expressing FoxP3 in injected and non-injected tumors.

FIG. 7 is a series of bar graphs showing that intratumoral injection of MVAΔE3L-hFlt3L is effective in the recruitment of CD45+ cells and CD8+ cells, and increases the ratio of CD8+/Treg as well as of conventional CD4+/Treg in both injected and non-injected tumors. (A, B) two plots of absolute numbers of tumor-infiltrating CD45+ and CD8+ cells respectively per gram of injected and non-injected tumors of mice treated with PBS, MVAΔE3L, MVAΔE3L-mGM-CSF, MVAΔE3L-hFlt3L, or Heat-MVA (*, p<0.05, **, p<0.01, ns: non-significant). (C) Ratios of CD8+/Treg in injected and non-injected tumors (*, p<0.05, **, p<0.01, ns: non-significant). (D) Ratios of conventional CD4+/Treg in injected and non-injected tumors (*, p<0.05, ns: non-significant). Data are means±SEM (n=3 for PBS group and n=5 for each virus group).

FIG. 13 is a series of graphic representations of data showing that intratumoral injection of MVAΔE3L-hFlt3L leads to the influx of Ly6C+ CD11b$^-$ and Ly6C+ CD11b+ cells in both injected and non-injected tumors. (A, B) Percentages of Ly6C$^{hi}$CD11b+ cells out of CD45+ cells in both injected (B) and non-injected (A) tumors of WT mice treated with PBS, MVAΔE3L, MVAΔE3L-mGM-CSF, MVAΔE3L-hFlt3L, or Heat-MVA as well as Batf3$^{-/-}$ mice treated with PBS or MVAΔE3L-Flt3L (*, p<0.05, , p<0.01, **, p<0.0001). (C, D) Percentages Ly6C$^{hi}$CD11b$^-$ cells of out of CD45+ cells in both injected (B) and non-injected (A) tumors (*, p<0.05, , p<0.01, *, p<0.001). Data are means±SEM (n=4 for PBS group and n=5 for each virus group in WT mice; n=2 for PBS group and n=5 for each virus group in Batf3$^{-/-}$ mice).

FIG. 16 shows a series of graphical representations of intratumoral injection of MVAΔE3L-hFlt3L in a prostate carcinoma TRAMP-C2 unilateral implantation model in WT C57B/6 and STING$^{Gt/Gt}$ mice. (A-D) are a series of graphs of respective tumor volumes over days after injection with PBS, or MVAΔE3L-hFlt3L in WT or STING$^{Gt/Gt}$ mice. (E) is a graph of the respective initial tumor volumes on the day of first injection with viruses (n=10 for PBS and n=10 for MVAΔE3L-hFlt3L in WT mice; n=7 for PBS and n=10 for MVAΔE3L-hFlt3L in STING$^{Gt/Gt}$ mice *, P<0.05).

(F) is a graph of respective tumor volumes at day 24 post the first injections. (n=10 for PBS and n=10 for MVAΔE3L-hFlt3L in WT mice; n=7 for PBS and n=10 for MVAΔE3L-hFlt3L in STING$^{Gt/Gt}$ mice; *, P<0.05; ****, P<0.0001).

FIG. 17 is a series of graphical representations of data showing the combination of intratumoral injection of MVA-hFlt3L is effective for delaying the growth or eradicating tumors in a bilateral B16-F10 murine melanoma implantation model. (A) Volumes of injected and contralateral non-injected tumors over days after injections with PBS, or MVA-hFlt3L, or MVAΔE3L-hFlt3L in a bilateral B16-F10 murine melanoma implantation model. (C) Kaplan-Meier survival curve of B16-F10 tumor-bearing mice treated with PBS (n=5), or MVA-hFlt3L (n=9; *, p<0.001). Furthermore, FIG. 17 (A-C) shows that the combination of intratumoral injection of MVAΔE3L-hFlt3L with systemic delivery of anti-CTLA-4, anti-PD-1, or anti-PD-L1 antibodies increases the overall response and cure rates in a B16-F10 bilateral implantation model. (B) Volumes of injected and contralateral non-injected tumors over days after intratumoral injections with MVAΔE3L-hFlt3L in the presence of intraperitoneal delivery of anti-CTLA-4, anti-PD-1, or anti-PD-L1 antibodies in a bilateral B16-F10 murine melanoma implantation model. (C) Kaplan-Meier survival curve of tumor-bearing mice treated with PBS (n=5), MVA-hFlt3L (n=8), MVAΔE3L-hFlt3L+isotype control (n=9), MVAΔE3L-hFlt3L+anti-CTLA4 antibody (n=9), MVAΔE3L-hFlt3L+anti-PD1 antibody (n=9), or MVAΔE3L-hFlt3L+anti-PD-L1 antibody (n=8; *, p<0.001). (D) Kaplan-Meier survival curve of naïve mice (n=5) and surviving mice treated with MVAΔE3L-hFlt3L+ anti-CTLA4 antibody (n=2), MVAΔE3L-hFlt3L+anti-PD1 antibody (n=3), or MVAΔE3L-hFlt3L+anti-PD-L1 antibody (n=4) re-challenged intradermally with a lethal dose of MC38 colon adenocarcinoma cells ($1 \times 10^5$).

FIG. 18 is a series of graphical representations of data showing that Intratumoral injection with MVAΔE3L-hFlt3L leads to the generation of antitumor $CD8^+$ T cell immunity against autologous and heterologous tumors, which is enhanced in the presence of anti-CTLA-4 antibody. (A) is a scanned image of ELISPOT in triplicates. Pooled $CD8^+$ T cells isolated from 3 spleens of naïve mice were used as a negative control (Naïve). Pooled $CD8^+$ T cells isolated from 3 spleens of MVAΔE3L-hFlt3L-treated mice without anti-CTLA-4 (-Ab) showed reactivity against both irradiated B16-F10 and MC38. Pooled $CD8^+$ T cells isolated from 3 spleens of MVAΔE3L-hFlt3L-treated mice with anti-CTLA-4 (+αCT) showed stronger reactivity against both irradiated B16-F10 and MC38 than those from virus-treated mice. (B) is a graph of positive spots against irradiated B16-F10 or MC38 under the conditions described in (A). (, p<0.01; **, p<0.0001).

Figure 19:
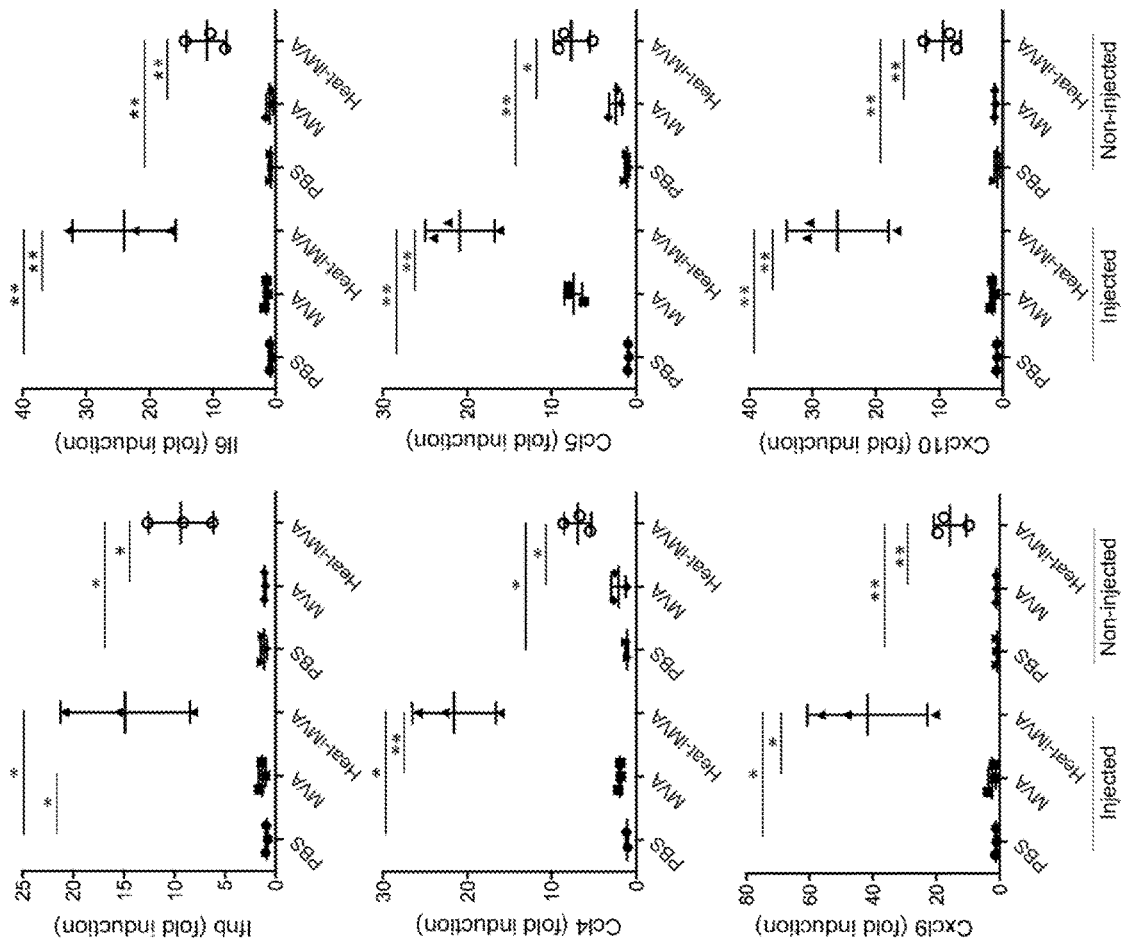

FIG. 19 is a series of graphical representations of data showing that intratumoral injection with Heat-inactivated MVA induces higher levels of type I IFN and inflammatory cytokines and chemokines gene expression in both injected and non-injected tumors than MVA in a bilateral B16-F10 tumor implantation model. Shown here are graphs of quantitative real-time PCR analyses of Ifnb, Il6, Ccl4, Ccl5, Cxcl9, and Cxcl10 gene expression in both injected and non-injected B16-F10 tumors treated with either PBS, MVA or Heat-MVA.

Figure 20A:
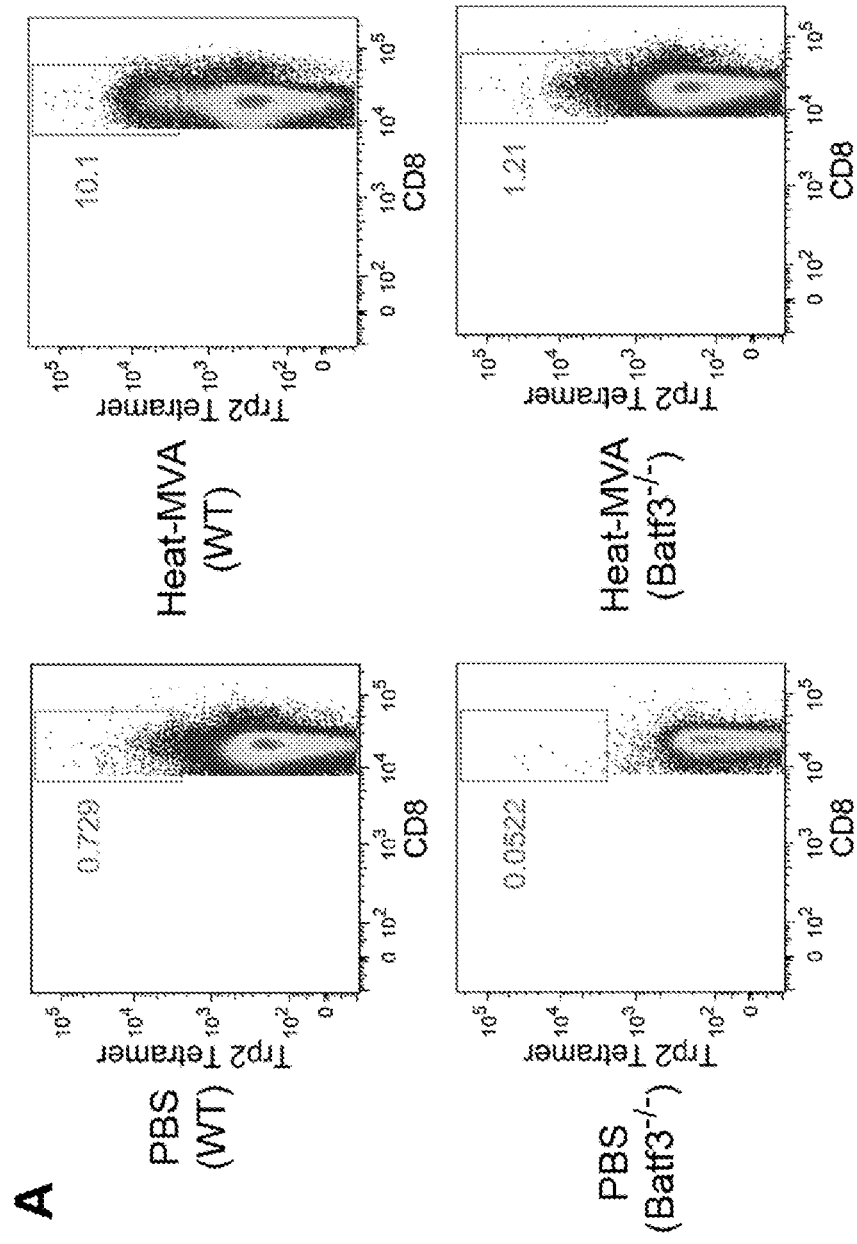
Figure 20B:
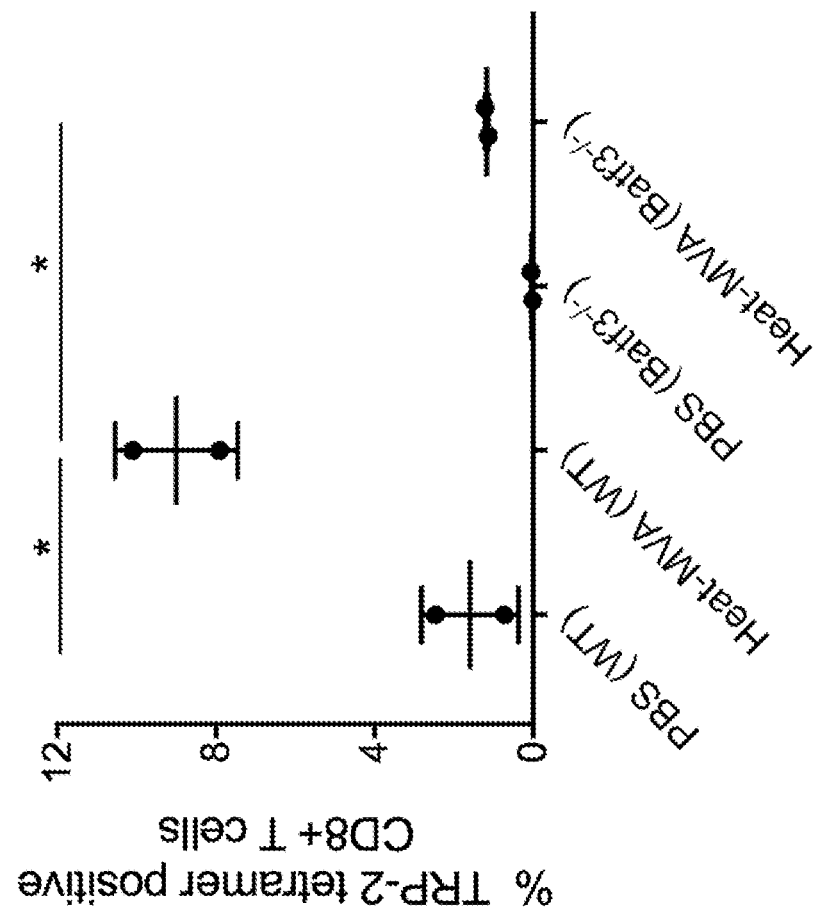

FIG. 20 is a series of graphic representations showing that intratumoral injection with Heat-inactivated MVA induces anti-melanoma $CD8^+$ T cell responses in the tumor draining lymph nodes (TDLNs). (A) are a series of representative flow cytometry plots of TRP-2 tetramer positive $CD8^+$ T cells in tumor draining lymph nodes in a B16-F10 melanoma model treated with either PBS or Heat-inactivated MVA. (B) is a graph of the percentages of TRP-2 tetramer positive $CD8^+$ T cells in WT and $Batf3^{-/-}$ mice with B16-F10 melanomas treated with either PBS or Heat-MVA. Each sample were from lymph nodes pooled from 2-3 mice treated with the same condition. (*, p<0.05).

FIG. 21 is a series of graphic representations showing that intratumoral injection with MVAΔE3L-hFlt3L is effective in the treatment of large established B16-OVA melanoma in a unilateral tumor implantation model. (A) is a schematic diagram of a unilateral tumor implantation model with large established B16-OVA model. B16-OVA melanoma cells ($5 \times 10^5$ cells) were implanted intradermally to the right flanks of C57B/6 mice. 8-9 days after tumor implantation, mice were intratumorally injected with $2 \times 10^7$ pfu of MVAΔE3L-hFlt3L, Heat-MVA, poly (I:C), or PBS mock control twice weekly. Tumor sizes were measured and the survival of mice was monitored. (B) Volumes of injected tumors over days after injections with PBS, MVAΔE3L-hFlt3L, Heat-MVA, or poly (I:C). (C) is a graph of the respective initial tumor volumes on the day of first injection with viruses or poly (I:C) (n=10). (D) is a Kaplan-Meier survival curve of tumor-bearing mice treated with PBS, MVAΔE3L-hFlt3L, Heat-MVA, or poly (I:C) intratumorally (n=10; ****, p<0.0001).

Figure 22A:
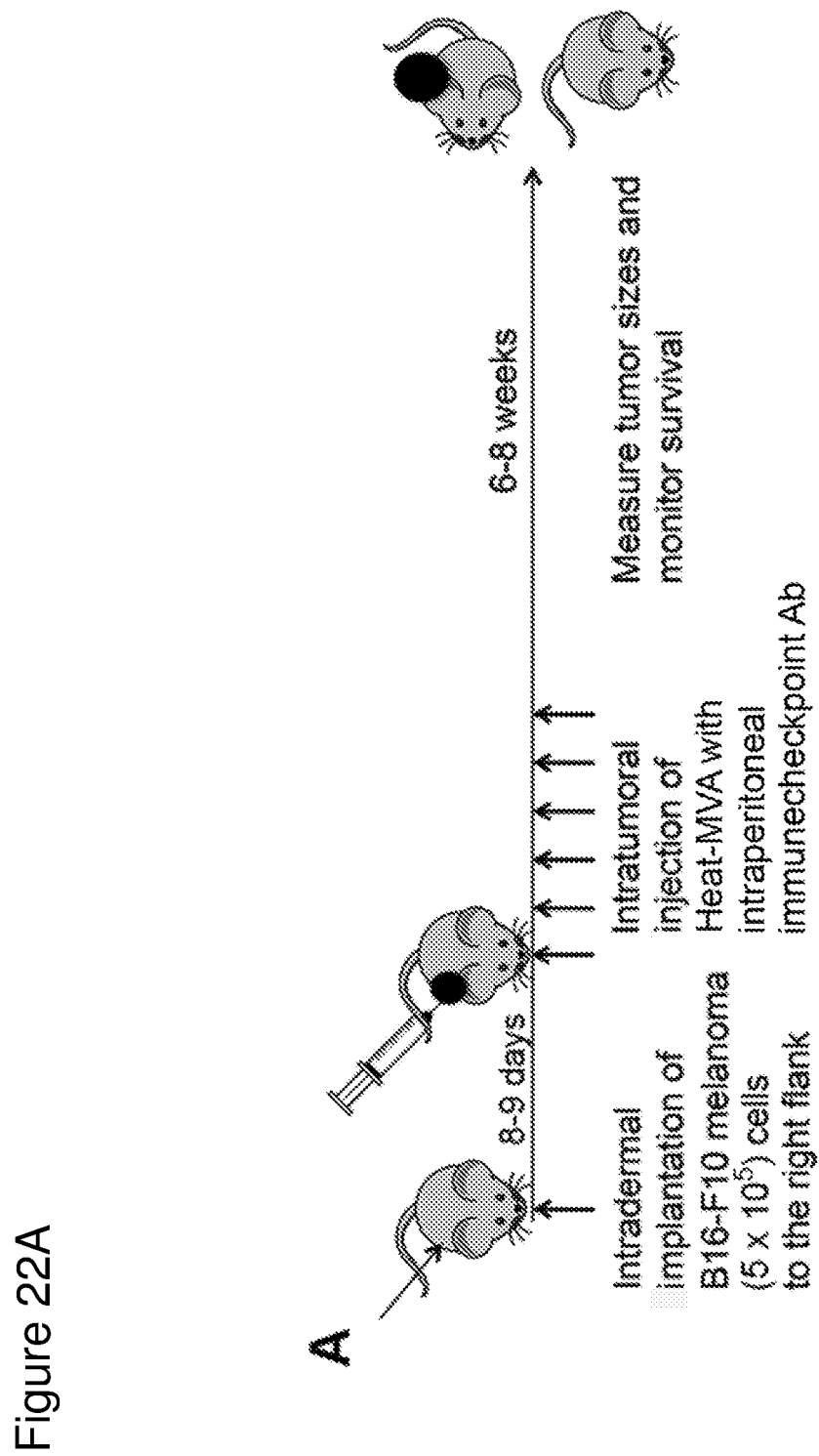
Figure 22B:
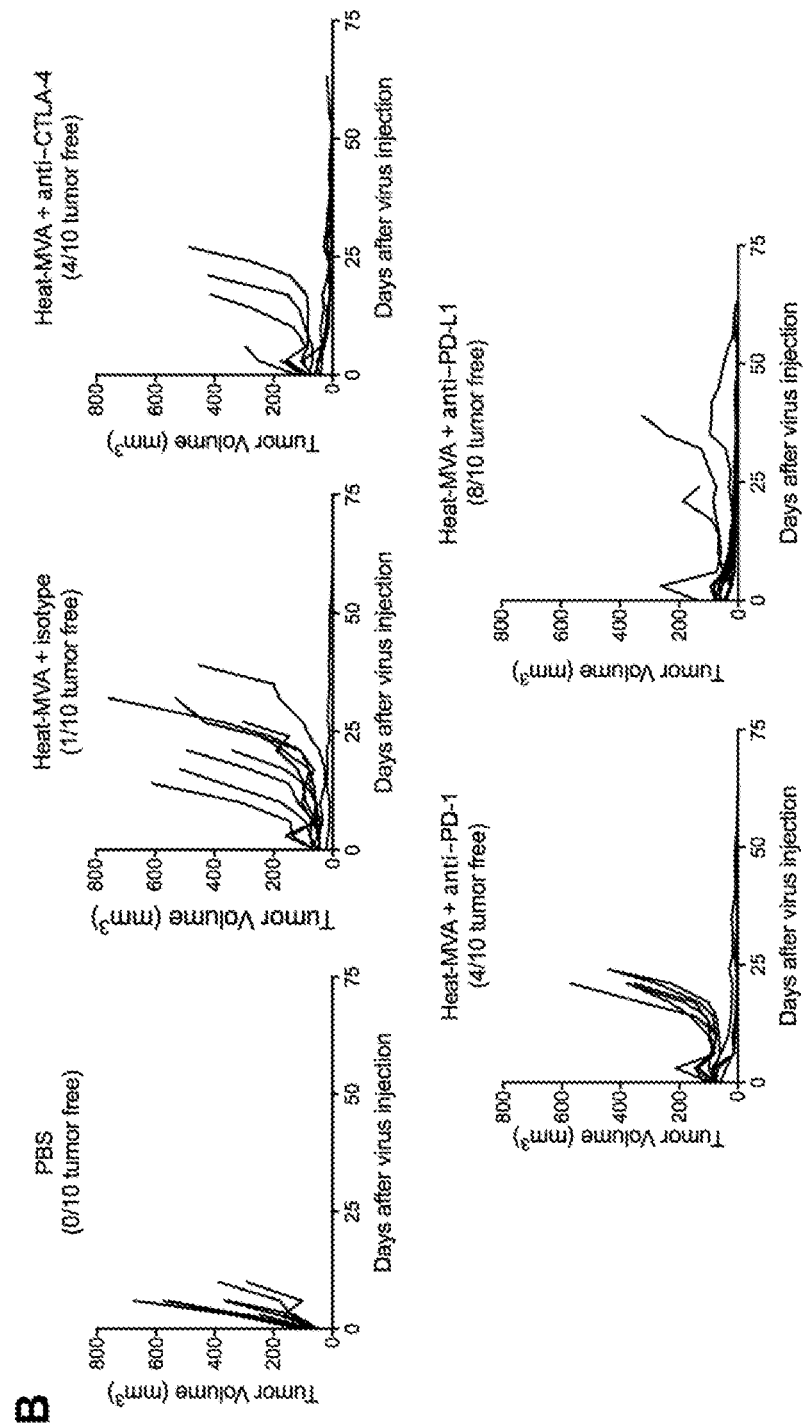

FIG. 22 is a series of graphic representations showing that the combination of intratumoral injection with Heat-inactivated MVA and systemic delivery of immune checkpoint antibodies improves antitumor efficacy in a large established melanoma unilateral implantation model. (A) is a schematic diagram of a unilateral tumor implantation model with large established B16-F10 model. B16-F10 melanoma cells ($5 \times 10^5$ cells) were implanted intradermally to the right flanks of C57B/6 mice. 8-9 days after tumor implantation, mice were intratumorally injected with $2 \times 10^7$ pfu of Heat-MVA twice weekly in the presence or absence of intraperitoneal delivery of anti-CTLA-4, anti-PD-1, or anti-PD-L1 antibodies. Tumor sizes were measured and the survival of mice was monitored. (B) Volumes of injected tumors over days after injections with PBS, or with Heat-MVA in the presence of isotype control, or anti-CTLA-4, or anti-PD-1, or Anti-PD-L1. (C) is a graph of the respective initial tumor volumes prior to first treatment. (n=10). (D) is a Kaplan-Meier survival curve of tumor-bearing mice treated with PBS, or Heat-MVA in the presence of isotype control, or anti-CTLA-4, or anti-PD-1, or Anti-PD-L1 (n=10; *, p<0.05, , p<0.01, **, p<0.0001).

DETAILED DESCRIPTION

Definitions

As used herein the following terms shall have the meanings ascribed to them below unless the context clearly indicates otherwise:

"Cancer" refers to a class of diseases of humans and animals characterized by uncontrolled cellular growth. Unless otherwise explicitly indicated, the term "cancer" may be used herein interchangeably with the terms "tumor," "malignancy," "hyperproliferation" and "neoplasm(s);" the term "cancer cell(s)" is interchangeable with the terms "tumor cell(s)," "malignant cell(s)," "hyperproliferative cell (s)," and "neoplastic cell(s)".

"Melanoma" refers to a malignant neoplasm originating from cells that are capable of producing melanin. The term melanoma is synonymous with "malignant melanoma". Melanoma metastasizes widely, involving a patient's lymph nodes, skin, liver, lungs and brain tissues.

"Solid tumor" refers to all neoplastic cell growth and proliferation, and all pre-cancerous and cancerous cells and tissues, except for hematologic cancers such as lymphomas, leukemias and multiple myeloma. Examples of solid tumors include, but are not limited to: soft tissue sarcoma, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor and other bone tumors (e.g., osteosarcoma, malignant fibrous histiocytoma), leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, brain/CNS tumors (e.g., astrocytoma, glioma, glioblastoma, childhood tumors, such as atypical teratoid/rhabdoid tumor, germ cell tumor, embryonal tumor, ependymoma) medulloblastoma, craniopharyngioma, ependymoma, pinealoma, hemangioblastoma, acoustic neuroma, oligodendroglioma, meningioma, melanoma, neuroblastoma, and retinoblastoma. Some of the most common solid tumors for which the compositions and methods of the present disclosure would be useful include: head-and-neck cancer, rectal adenocarcinoma, glioma, medulloblastoma, urothelial carcinoma, pancreatic adenocarcinoma, uterine (e.g., endometrial cancer, fallopian tube cancer) ovarian cancer, cervical cancer prostate adenocarcinoma, non-small cell lung cancer (squamous and adenocarcinoma), small cell lung cancer, melanoma, breast carcinoma, ductal carcinoma in situ, renal cell carcinoma, and hepatocellular carcinoma, adrenal tumors (e.g., adrenocortical carcinoma), esophageal, eye (e.g., melanoma, retinoblastoma), gallbladder, gastrointestinal, Wilms' tumor, heart, head and neck, laryngeal and hypopharyngeal, oral (e.g., lip, mouth, salivary gland), nasopharyngeal, neuroblastoma, peritoneal, pituitary, Kaposi's sarcoma, small intestine, stomach, testicular, thymus, thyroid, parathyroid, vaginal tumor and the metastases of any of the foregoing.

"Metastasis" refers to the spread of cancer from its primary site to neighboring tissues or distal locations in the body. Cancer cells (including cancer stem cells) can break away from a primary tumor, penetrate lymphatic and blood vessels, circulate through the bloodstream, and grow in in normal tissues elsewhere in the body. Metastasis is a sequential process, contingent on tumor cells (or cancer stem cells) breaking off from the primary tumor, traveling through the bloodstream or lymphatics, and stopping at a distant site. Once at another site, cancer cells re-penetrate through the blood vessels or lymphatic walls, continue to multiply, and eventually form a new tumor (metastatic tumor). In some embodiments, this new tumor is referred to as a metastatic (or secondary) tumor.

"Immune response" refers to the action of one or more of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, etc. An immune response may include a cellular response, such as a T cell response that is an alteration (modulation, e.g., significant enhancement, stimulation, activation, impairment, or inhibition) of cellular, i.e., T cell function. A T cell response may include generation, proliferation or expansion, or stimulation of a particular type of T cell, or subset of T cells, for example, effector $CD4^+$, $CD4^+$ helper, effector $CD8^+$, $CD8^+$ cytotoxic, or natural killer (NK) cells. Such T cell subsets may be identified by detecting one or more cell receptors or cell surface molecules (e.g., CD or cluster of differentiation molecules). A T cell response may also include altered expression (statistically significant increase or decrease) of a cellular factor, such as a soluble mediator (e.g., a cytokine, lymphokine, cytokine binding protein, or interleukin) that influences the differentiation or proliferation of other cells. For example, Type I interferon (IFN-$\alpha/\beta$) is a critical regulator of the innate immunity (52) (Huber et al. *Immunology* 132(4):466-474 (2011)). Animal and human studies have shown a role for IFN-$\alpha/\beta$ in directly influencing the fate of both $CD4^+$ and $CD8^+$ T cells during the initial phases of antigen recognition and anti-tumor immune response. IFN Type 1 is induced in response to activation of dendritic cells, in turn a sentinel of the innate immune system. An immune response may also include humoral (antibody) response.

"Tumor immunity" refers to one or more processes by which tumors evade recognition and clearance by the immune system. Thus, as a therapeutic concept, tumor immunity is "treated" when such evasion is attenuated or eliminated, and the tumors are recognized and attacked by the immune system (the latter being termed herein "anti-tumor immunity"). An example of tumor recognition is tumor binding, and examples of tumor attack are tumor reduction (in number, size or both) and tumor clearance.

"T cell" refers to a thymus derived lymphocyte that participates in a variety of cell-mediated adaptive immune reactions.

"Helper T cell" refers to a $CD4^+$ T cell; helper T cells recognize antigen bound to MHC Class II molecules. There are at least two types of helper T cells, Th1 and Th2, which produce different cytokines.

"Cytotoxic T cell" refers to a T cell that usually bears CD8 molecular markers on its surface ($CD8^+$) and that functions in cell-mediated immunity by destroying a target cell having a specific antigenic molecule on its surface. Cytotoxic T cells also release Granzyme, a serine protease that can enter target cells via the perforin-formed pore and induce apoptosis (cell death). Granzyme serves as a marker of cytotoxic phenotype. Other names for cytotoxic T cell include CTL, cytolytic T cell, cytolytic T lymphocyte, killer T cell, or killer T lymphocyte. Targets of cytotoxic T cells may include virus-infected cells, cells infected with bacterial or protozoal parasites, or cancer cells. Most cytotoxic T cells have the protein CD8 present on their cell surfaces. CD8 is attracted to portions of the Class I MHC molecule. Typically, a cytotoxic T cell is a $CD8^+$ cell.

"Tumor-infiltrating leukocytes" refers to white blood cells of a subject afflicted with a cancer (such as melanoma), that are resident in or otherwise have left the circulation (blood or lymphatic fluid) and have migrated into a tumor.

"Immune checkpoint inhibitor" or "immune checkpoint blocking agent" or "immune checkpoint blockade inhibitor" refers to molecules that completely or partially reduce, inhibit, interfere with or modulate the activity of one or more checkpoint proteins. Checkpoint proteins regulate T-cell activation or function. Checkpoint proteins include, but are not limited to, CD28 receptor family members, CTLA-4 and its ligands CD80 and CD86; PD-1 and its ligands PDL1 and PDL2; LAG3, B7-H3, B7-H4, TIM3, ICOS, II DLBCL, BTLA or any combination of two or more of the foregoing (53). Nonlimiting examples contemplated for use herein include ipilimumab, nivolumab, pembrolizumab, pidilizumab, AMP-224, MPDL3280A, BMS-936559, MEDI4736, MSB 00107180, or any combination thereof.

"Parenteral" when used in the context of administration of a therapeutic substance or composition includes any route of administration other than administration through the alimentary tract. Particularly relevant for the methods disclosed herein are intravenous (including for example through the hepatic portal vein for hepatic delivery), intratumoral or intrathecal administration.

"Antibody" refers to an immunoglobulin molecule which specifically binds to an antigen or to an antigen-binding fragment of such a molecule. Thus, antibodies can be intact immunoglobulins derived from natural sources or from recombinant sources and can be immunoreactive (antigen-binding) fragments or portions of intact immunoglobulins. The antibodies may exist in a variety of forms including, for example, polyclonal antibodies, monoclonal antibodies, Fv, Fab and F(ab)2, as well as single chain antibodies (scFv) humanized antibodies, chimeric antibodies, human recombinant antibodies and bi- and tri-specific antibodies.

"Oncolytic virus" refers to a virus that preferentially infects cancer cells, replicates in such cells, and induces lysis of the cancer cells through its replication process. Nonlimiting examples of naturally occurring oncolytic viruses include vesicular stomatitis virus, reovirus, as well as viruses engineered to be oncoselective such as adenovirus, Newcastle disease virus and herpes simplex virus (See, e.g., Nemunaitis, J. *Invest New Drugs.* 17(4):375-86 (1999); Kirn, D H et al. *Nat Rev Cancer.* 9(1):64-71(2009); Kim et al. *Nat. Med.* 7:781 (2001); Coffey et al. *Science* 282:1332 (1998)) (8, 54-56). Vaccinia virus infects many types of cells but replicates preferentially in tumor cells due to the fact that tumor cells have a metabolism that favors replication, exhibit activation of certain pathways that also favor replication and create an environment that evades the innate immune system, which also favors viral replication. In the context of the present disclosure, MVA and MVAΔE3L do not fit the definition of oncolytic viruses as they do not produce an antitumor effect primarily by replicating inside tumor cells and causing apoptosis. (Nor do they fit the classic definition of vaccines as these viruses do not express tumor antigens. It can be said however, that they act as immunostimulatory molecules, akin to adjuvants, as they serve to promote and enhance the host's immune response against the tumor.)

"MVA" means "modified vaccinia Ankara" and refers to a highly attenuated strain of vaccinia derived from the Ankara strain and developed for use as a vaccine and vaccine adjuvant. The original MVA was isolated from the wild-type Ankara strain by successive passage through chicken embryonic cells, Treated thus, it lost about 15% of the genome of wild-type vaccinia including its ability to replicate efficiently in primate (including human) cells. (57) (Mayr et al., *Zentralbl Bakteriol B* 167, 375-390 (1978)). The smallpox vaccination strain MVA: marker, genetic structure, experience gained with the parenteral vaccination and behavior in organisms with a debilitated defense mechanism. MVA is considered an appropriate candidate for development as a recombinant vector for gene or vaccination delivery against infectious diseases or tumors. (58) (Verheust et al., *Vaccine* 30(16), 2623-2632 (2012)). MVA has a genome of 178 kb in length and a sequence first disclosed in (59) (Antoine et al., *Virol.* 244(2): 365-396 (1998)). Sequences are also disclosed in Genbank U94848.1. Clinical grade MVA is commercially and publicly available from Bavarian Nordic A/S Kvistgaard, Denmark. Additionally, MVA is available from ATCC, Rockville, Md. and from CMCN (Institut Pasteur Collection Nationale des Microorganismes) Paris, France.

"MVAΔE3L" means a deletion mutant of MVA which lacks a functional E3L gene and is infective but non replicative and it is further impaired in its ability to evade the host's immune system. It has been used as a vaccine vector (by others) to transfer tumor or viral antigens. This mutant MVA E3L knockout and its preparation have been described for example in U.S. Pat. No. 7,049,145.

"Subject" means any animal (mammalian, human or other) patient that can be afflicted with cancer and when thus afflicted is in need of treatment.

"Pharmaceutically acceptable excipient" as used herein refers to substances and compositions that do not produce an adverse, allergic or other untoward reaction when administered to an animal or a human. As used herein, the term includes all inert, non-toxic, liquid or solid fillers or diluents, as long as they do not react with the therapeutic substance of the invention in an inappropriate negative manner, solvents, dispersion media, coatings, antibacterial and antifungal agents, isotonic and absorption delaying agents, preservatives and the like, for example liquid pharmaceutical carriers e.g., sterile water, saline, sugar solutions, Tris buffer, ethanol and/or certain oils.

"Therapeutically effective amount" or "effective amount" refers to a sufficient amount of an agent when administered at one or more dosages and for a period of time sufficient to provide a desired biological result in alleviating, curing or palliating a disease. In the present disclosure, an effective amount respectively of the MVA or MVAΔE3L is an amount that (administered for a suitable period of time and at a suitable frequency) reduces the number of cancer cells; or reduces the tumor size or eradicates the tumor; or inhibits (i.e., slows down or stops) cancer cell infiltration into peripheral organs; inhibits (i.e., slows down or stops) metastatic growth; inhibits (stabilizes or arrests) tumor growth; allows for treatment of the tumor, and/or induces and promotes an immune response against the tumor. An appropriate therapeutic amount in any individual case may be determined by one of ordinary skill in the art using routine experimentation in light of the present disclosure. Such determination will begin with amounts found effective in vitro and amounts found effective in animals. The therapeutically effective amount will be initially determined based on the concentration or concentrations found to confer a benefit to cells in culture. Effective amounts can be extrapolated from data within the cell culture and can be adjusted up or down based on factors such as detailed herein. Effective amounts of the viral constructs are generally within the range of about $10^5$ to about $10^{10}$ plaque forming units (pfu), although a lower or higher dose may be administered. In a preferred embodiment, the dosage is about $10^6$-$10^9$ pfu. Typically, a unit dosage is administered in a volume within the range from 1 to 10 ml. The equivalence of pfu to virus particles can differ according to the specific pfu titration method used. Generally, pfu is equal to about 5 to 100 virus particles. A therapeutically effective amount the hFlt3L transgene bearing viruses can be administered in one or more divided doses for a prescribed period of time and at a prescribed frequency of administration. For example, therapeutically effective amount of hFlt3L bearing viruses in accordance with the present disclosure may vary according to factors such as the disease state, age, sex, weight, and general condition of the subject, and the potency of the viral constructs to elicit a desired immunological response in the particular subject for the particular cancer.

With particular reference to the viral-based immunostimulatory agents disclosed herein, "therapeutically effective amount" or "effective amount" refers to an amount of a composition comprising MVA-hFlt3L or MVAΔE3L-hFlt3L sufficient to reduce, inhibit, or abrogate tumor cell growth, thereby reducing or eradicating the tumor, or sufficient to inhibit, reduce or abrogate metastatic spread either in vitro, ex vivo or in a subject or to elicit and promote an immune response against the tumor that will eventually result in one or more of metastatic spread reduction, inhibition and/or abrogation as the case may be. The reduction, inhibition, or eradication of tumor cell growth may be the result of necrosis, apoptosis, or an immune response or a combination of two or more of the foregoing (however, the precipitation of apoptosis for example may not be due to the same factors as observed with oncolytic viruses). The amount that is therapeutically effective may vary depending on such factors as the particular virus used in the composition, the age and condition of the subject being treated, the extent of tumor formation, the presence or absence of other therapeutic modalities, and the like. Similarly, the dosage of the composition to be administered and the frequency of its administration will depend on a variety of factors, such as the potency of the active ingredient, the duration of its activity once administered, the route of administration, the size, age, sex and physical condition of the subject, the risk of adverse reactions and the judgment of the medical practitioner. The compositions are administered in a variety of dosage forms, such as injectable solutions.

With particular reference to combination therapy with an immune checkpoint inhibitor, "therapeutically effective amount" for an immune checkpoint blocking agent shall mean an amount of an immune checkpoint blocking agent sufficient to reverse or reduce immune suppression in the tumor microenvironment and to activate or enhance host immunity in the subject being treated. There are several immune checkpoint blocking agents approved, in clinical trials or still otherwise under development including inhibitory antibodies against CD28 inhibitor such as CTLA-4 (cytotoxic T lymphocyte antigen 4) (e.g., ipilimumab), anti-PD-1 (programmed Death 1) inhibitory antibodies (e.g., nivolumab, pembrolizumab, pidilizumab, lambrolizumab), and anti-PD-L1 (Programmed death ligand 1) inhibitory antibodies (MPDL3280A, BMS-936559, MEDI4736, MSB 00107180), as well as inhibitory antibodies against LAG-3 (lymphocyte activation gene 3), TIM3 (T cell Immunoglobulin and Mucin-3), B7-H3, and TIGIT (T-cell immunoreceptor with Ig and ITIM domains). Dosage ranges of the foregoing are known or readily within the skill in the art as several dosing clinical trials have been completed, making extrapolation to other agents possible.

Preferably, the tumor expresses the particular checkpoint but in the context of the present invention this is not strictly necessary as immune checkpoint blocking agents block more generally immune suppressive mechanisms within the tumors, elicited by tumor cells, stromal cells, and tumor-infiltrating immune cells.

For example, the CTLA4 inhibitor ipilimumab, when administered as adjuvant therapy after surgery in melanoma is administered at 1-2 mg/mL over 90 minutes for a total infusion amount of 3 mg/kg every three weeks for a total of 4 doses. This therapy is often accompanied by severe even life-threatening immune-mediated adverse reactions, which limits the tolerated dose as well as the cumulative amount that can be administered. It is anticipated that it will be possible to reduce the dose and/or cumulative amount of ipilimumab when it is administered conjointly with MVA-hFlt3L or MVAΔE3L-hFlt3L. In particular, in light of the experimental results set forth below, it is anticipated that it will be further possible to reduce the CTLA4 inhibitor's dose if it is administered directly to the tumor conjointly with one or both the foregoing MVA viruses. Accordingly, the amounts provided above for ipilimumab will be a starting point for determining the particular dosage and cumulative amount to be given to a patient in conjoint administration but dosing studies will be required to determine optimum amounts.

Pembrolizumab is prescribed for administration as adjuvant therapy in melanoma diluted to 25 mg/mL. It is administered at a dosage of 2 mg/kg over 30 minutes every three weeks. Again, this would be a starting point for determining dosage and administration in the conjoint administration with MVA-hFlt3L or MVA6,E3L-hFlt3L.

Nivolumab is prescribed for administration at 3 mg/kg as an intravenous infusion over 60 minutes every two weeks, providing a similar starting point in determining dosage and administration regimen of this and other checkpoint inhibitors conjointly with MVA-hFlt3L or MVAΔE3L-hFlt3L described herein or conjointly with Heat-MVA (inactivated MVA which inactivation can be heat-induced or UV radiation-induced) in amounts generally within the same range as the viruses and vital constructs of MVA and MVA ΔE3L.

Immune stimulating agents such as agonist antibodies have also been explored as immunotherapy for cancers. For example, anti-ICOS antibody binds to the extracellular domain of ICOS leading to the activation of ICOS signaling and T cell activation. Anti-OX40 antibody can bind to OX40 and potentiate T cell receptor signaling leading to T cell activation, proliferation and survival. Other examples include agonist antibodies against 4-IBB (CD137), GITR. All of these agents are at various stages of clinical trials.

The immune stimulating agonist antibodies can be used systemically in combination with intratumoral injection of MVA-hFlt3L or MVAΔE3L-hFlt3L (or inactivated MVA). Alternatively, the immune stimulating agonist antibodies can be used conjointly with MVA-hFlt3L or MVAΔE3L-hFlt3L via intratumoral delivery either simultaneously or sequentially.

"Pharmaceutically acceptable carrier and/or diluent" or "pharmaceutically acceptable excipient" includes without limitation any and all solvents, dispersion media, coatings, antibacterial and antifungal agents, isotonic and absorption delaying agents and the like. The use of such media and agents for biologically active substances is well known in the art. Further details of excipients are provided below. Supplementary active ingredients, such as antimicrobials, for example antifungal agents, can also be incorporated into the compositions.

"Delivering" used in connection with depositing the MVA-hFlt3L or MVAΔE3L-hFlt3L (or Heat-MVA in conjoint administration with immune checkpoint blockade inhibitors, especially for large established tumors) of the present disclosure in the tumor microenvironment whether this is done by local administration to the tumor (intratumoral) or by for example intravenous route. The term focuses on MVA-hFlt3L or MVAΔE3L-hFlt3L that reaches the tumor itself.

"Conjoint administration" herein refers to administration of a second therapeutic modality in combination with MVA-hFlt3L or MVAΔE3L-hFlt3L for example an immune checkpoint blocking agent administered in close temporal proximity with MVA-hFlt3L or MVAΔE3L-hFlt3L. For example, a PD-1/PDL-1 inhibitor and/or a CTLA4 inhibitor (in more specific embodiments, an antibody) can be administered simultaneously with MVA-hFlt3L or MVAΔE3L-hFlt3L (by intravenous or intratumoral injection when the MVA-hFlt3L or MVAΔE3L-hFlt3L is administered intratumorally or systemically as stated above) or before or after the MVA-hFlt3L or MVAΔE3L-hFlt3L administration. If the MVA-hFlt3L or MVAΔE3L-hFlt3L administration and the immune checkpoint blocking agent are administered 1-7 days apart or even up to three weeks apart, this would still be within "close temporal proximity" as stated herein, therefore such administration will qualify as "conjoint."

"Vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

In the present disclosure, the inventors generated recombinant MVA and MVAΔE3L viruses expressing human Flt3L, with the goal of delivering Flt3L to the tumor microenvironment to facilitate recruitment, differentiation and function of immune cells, including CD103$^+$/CD8α dendritic cells (DCs). Although in the particular experiments described below the transgene was inserted into the TK locus, splitting the TK gene and obliterating it, in the case of non replicative viruses this is not strictly necessary and another suitable integration locus could be chosen which is within the skill of the art. Thus, the label TK$^-$ has been omitted.

Jennerex has previously developed JX-594, in which vaccinia virus is engineered to express a transgene encoding granulocyte-macrophage colony stimulating factor (GM-CSF) with the deletion of vaccinia TK gene to increase tumor selectivity. GM-CSF is another important growth factor for DC homeostasis at the peripheral non-lymphoid tissues (King et al., 2010; Greter et al., 2012). Melanoma vaccine (GVAX) comprised of lethally irradiated allogeneic melanoma cells secreting GM-CSF has shown some clinical benefit (Dranoff et al., 2003). For Example, Curran and Allison showed that the combination of the melanoma cell line-based vaccine B16-GMCSF (GVAX) or the vaccine B16-Flt3L (Fl3VAX) with CTLA-4 blocking agent eradicated established melanoma in about 60% of the mice if the vaccines were administered at distal sites from the tumors (Curran and Allison, 2009). However, when the vaccines were administered to the tumors in combination with CTLA-4 blocking agent, GVAX was ineffective in tumor eradication in humans, whereas F13VAX treatment resulted in 75% of tumor-free mice (no human data). One potential explanation is that GM-CSF administration to the tumors might induce myeloid suppressor cell generation within the tumor (Serafini et al., 2004). With the concern that administration of GM-CSF to the tumors might induce immune tolerance, inventors of the present disclosure performed head-to-head comparisons of three recombinant viruses: MVAΔE3L, MVAΔE3L-mGM-CSF, and MVAΔE3L-hFlt3L for eradication of established B16 melanoma using a bilateral B10-F10 melanoma model (Example 2, FIGS. 3A and 3B). The inventors discovered that MVAΔE3L-hFlt3L is more efficacious than MVAΔE3L-mGM-CSF or MVAΔE3L in eradicating or delaying tumor growth. As described in Example 2, the inventors showed that intratumoral delivery of MVAΔE3L-hFlt3L is more efficacious than MVAΔE3L or MVAΔE3L-mGM-CSF in delaying the growth of contralateral tumor and extending survival. This systemic effect of MVAΔE3L$^-$-hFlt3L is important not only for the treatment of noninjected tumors, but also for the treatment of metastatic disease.

The inventors of the present disclosure have also shown that intratumoral injection of MVAΔE3L-hFlt3L leads to systemic immunity against a different tumor type upon rechallenge (Example 3). Using the surviving animals initially afflicted with melanoma (Example 2), the inventors rechallenged the animals with a different tumor type (colon cancer cells, Example 3). While the animals that have never been exposed to colon cancer cells or viruses developed tumors and died, animals that were previously treated with MVAΔE3L-hFlt3L rejected injected colon cancer cells.

The effects of intratumoral injection of MVAΔE3L, MVAΔE3L-mGM-CSF, MVAΔE3L-hFlt3L, or Heat-MVA in B16-F10 melanomas were assessed, and it was found that the comprise immunological changes in the tumor microenvironment, including activation and proliferation of cytotoxic CD8$^+$ and CD4$^+$ T cells, as well as reduction of immune suppressive regulatory T cells (Example 4).

Tumor-associated macrophages (TAMs) facilitate neoplastic transformation, tumor immune evasion and the subsequent metastatic cascade. In the present disclosure, the inventors have shown that MVAΔE3L-hFlt3L is effective in depleting TAMs (Example 5). To further study the mechanism of TAM reduction, the inventors have used Batf3-deficient mice. Batf3 is a transcription factor that is critical for the development of CD103$^+$/CD8α$^+$ lineage DCs, which play an important role in cross-presentation of viral and tumor antigens. As shown in Example 5, the number of TAMs in tumors of Batf3$^{-/-}$ mice was significantly reduced, which suggest that the generation of TAMs might be linked to the CD8$^+$ T cell infiltration within the tumors.

Additionally, the inventors monitored changes in tumor dendritic cell populations in response to MVAΔE3L-hFlt3L (Example 6). As shown in Example 6, intratumoral injection of MVAΔE3L-hFlt3L led to dynamic changes in the dendritic cell populations as evident by the reduction in CD24$^+$ DCs, CD103$^+$ DCs, as well as a decrease in CD11b$^+$ DCs.

Ly6C$^{hi}$CD11b$^+$ cells are C—C chemokine receptor (CCR2) expressing inflammatory monocytes that are recruited to site of injury or infection. The inventors of the present disclosure observed that intratumoral injection of MVAΔE3L-hFlt3L results in the influx of Ly6C$^{hi}$CD11b$^+$ and Ly6C$^+$ CD11b$^-$ cells (Example 7).

Figure 14A:
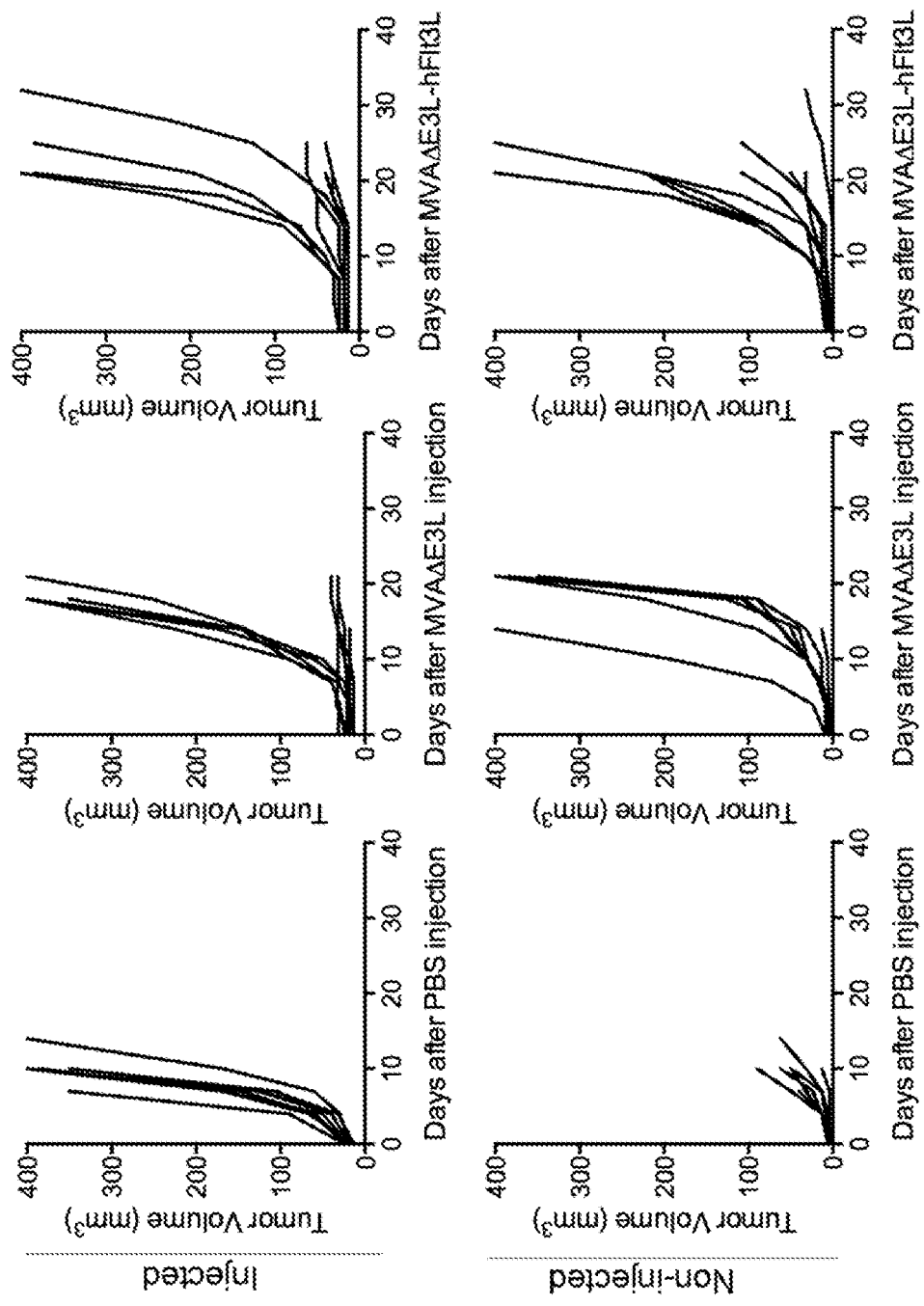
FIG. 14 is a series of graphical representations of data showing that intratumoral injection of MVAΔE3L-hFlt3L is more effective than MVAΔE3L in delaying the growth of both virus-injected and non-injected (contralateral) tumors in a bilateral MC38 tumor implantation model. (A) consists of 12 plots of volume of injected and non-injected tumor over days after injection with PBS, MVAΔE3L, or MVAΔE3L-hFlt3L viruses in a bilateral MC38 tumor implantation model. As described before, the viruses were only injected into the larger tumors on the right flank. (B) Kaplan-Meier survival curve of MC38 tumor-bearing mice treated with PBS (n=10), MVAΔE3L (n=10), or MVAΔE3L-hFlt3L (n=10; , p<0.01; **, p<0.0001).
Figure 14B:
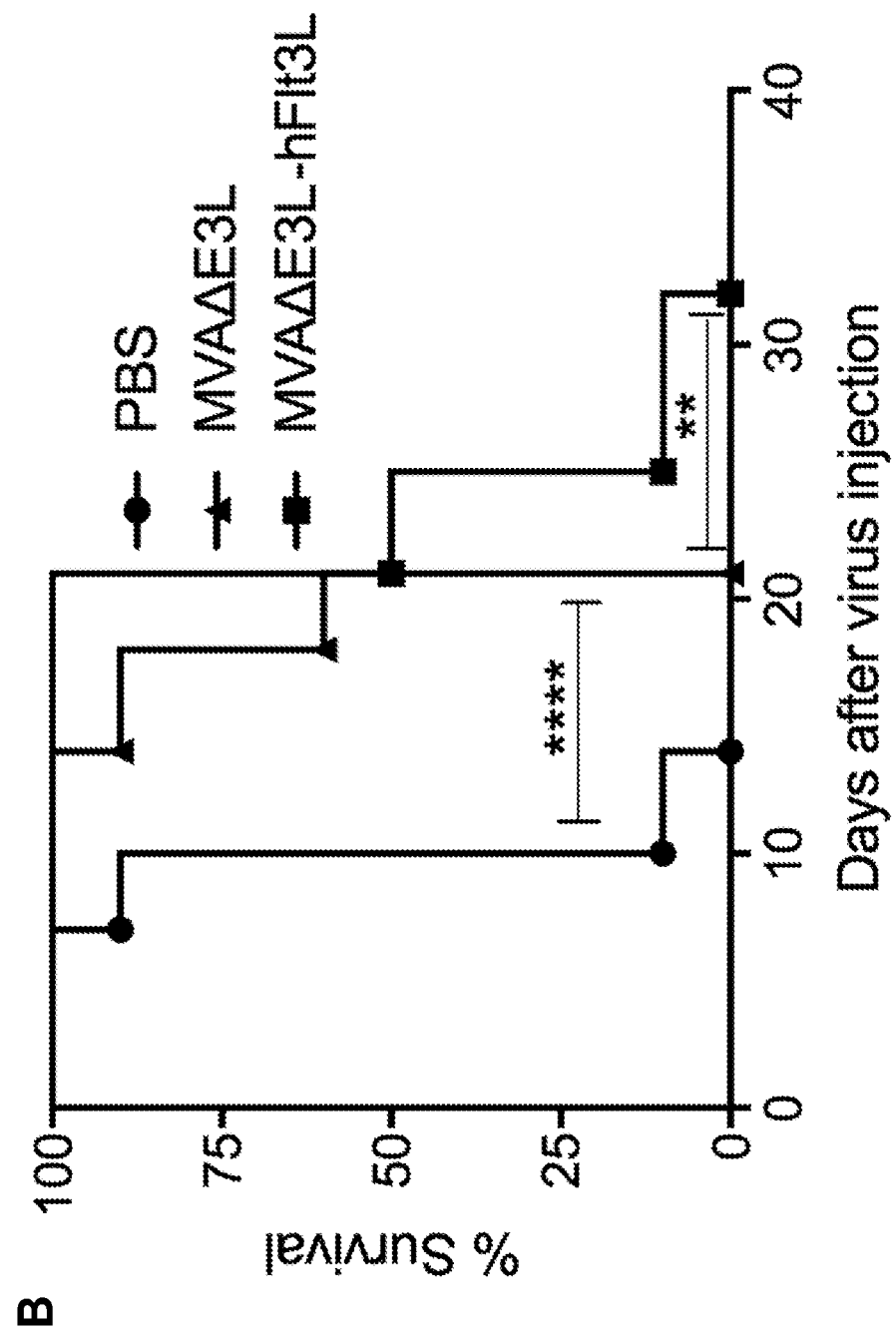

In addition to testing therapeutic effects of MVAΔE3L-hFlt3L in melanoma and delineating the immunological changes that occur due to MVAΔE3L-hFlt3L injection, the inventors sought out to determine whether MVAΔE3L-hFlt3L exhibits superior efficacy compared to MVAΔE3L in other tumor types. As shown in Example 8 (FIGS. 14A and 14B), intratumor injection of MVAΔE3L-hFlt3L is more effective than MVAΔE3L in delaying the growth of contralateral colon tumor and extending survival. Taken together, results observed in melanoma and colon cancer suggest that MVAΔE3L-hFlt3L can be used for treatment of a variety of solid tumors.

The inventors of the present disclosure have also shown that intratumoral injection of MVA-hFlt3L is effective in eradicating or delaying melanoma tumor growth, as well as in generation of systemic anti-tumor immunity (Example 9). Therefore, the inventors observed comparable patterns of therapeutic performance for both MVA-hFlt3L and MVAΔE3L-hFlt3L.

Additionally, the inventors have shown that intratumoral delivery of compositions and methods of the present disclosure overcomes resistance to immune checkpoint blocking agents. As shown in the Example 10, the combination of intratumoral delivery of MVAΔE3L-hFlt3L with systemic delivery of anti-CTLA-4, anti-PD1, or anti-PD-L1 antibody lead to synergistic antitumor effects in a bilateral B16-F10 melanoma implantation model. Furthermore, the inventors have demonstrated that the surviving mice treated with intratumoral injection of MVAΔE3L-hFlt3L with systemic delivery of immune checkpoint inhibitor (anti-CTLA-4, anti-PD1, or anti-PD-L1 antibody) developed immunity against rechallenge of a different tumor type (Example 11). Taken together, these results indicate for the first time that MVAΔE3L-hFlt3L may provide a successful and indeed a superior option for the treatment of solid tumor patients (including but not limited to colon cancer and melanoma), alone or in combination with immune checkpoint blocking agents.

In the present disclosure, the inventors explored whether MVA-hFlt3L or MVAΔE3L-hFlt3L strain can be used as cancer immunotherapeutic agent. In fact, they observed that intratumoral delivery of MVAΔE3L-hFlt3L is more efficacious in eradiating tumors and generating antitumoral immunity than MVAΔE3L. Similarly, intratumoral delivery of MVA-hFlt3L is more efficacious in eradiating tumors and generating antitumoral immunity than MVA. Thus, as a treatment option, patients can be treated with MVA-hFlt3L or MVAΔE3L-hFlt3L or both in order to achieve improved treatment results.

In one embodiment, the present disclosure relates to a method for eliciting and promoting an antitumor immune response in subjects with tumors comprising delivering to the tumor an effective amount of MVA-hFlt3L or MVAΔE3L-hFlt3L or both. Stimulation of the immune system may be manifested by one or more of the following immunological effects.

FACS data generated by the present inventors show that treatment with the present recombinant viruses harboring hFlt3 has qualitatively the same immunological effects as previously reported for inactivated MVA or for MVA or MVAΔE3L without hFLT3L: increase in $CD8^+$ T cells, increase in $CD4^+$ T cells, reduction in regulatory T cells. Based on these results, it is anticipated that the mechanism of immune response activation will be very similar to that shown in the prior experiments; induction of type I IFN and other proinflammatory cytokines, induction of maturation of dendritic cells, reduction of tumor-associated macrophages).

The foregoing one or more immunological effects may serve as early indicators of response of the subject to the treatment and may serve as monitors of the continued effectiveness of same.

In view of similarities shown between MVA-hFlt3L and MVAΔE3L-hFlt3L (Examples 2 and 9), it is anticipated that properties and advantages observed for MVAΔE3L-hFlt3L compared to MVAΔE3L that lacks hFlt3L, are also exhibited by MVA-hFlt3L compared to MVA alone.

In one embodiment, the present disclosure relates to a method for eliciting and promoting an antitumor immune response in subjects afflicted with tumors comprising delivering to the tumor an effective amount of MVA-hFlt3L or MVAΔE3L-hFlt3L. Stimulation of the immune system may be manifest by one or more of the following immunological effects:

an increase in antitumor cytotoxic $CD8^+$ (likely Type I interferon-related) and effector $CD4^+$ T cells within the tumor;

induction of maturation of dendritic cells infiltrating said tumor (this is also likely to be due to induction of Type I IFN as observed in prior work with inactivated MVA and with MVA and MVAΔE3L bearing no transgene);

induction of activated antitumor effector T cells in the subject;

reduction of immune suppressive (regulatory) $CD4^+$ T cells within the tumor;

increase of the ratio of cytotoxic $CD8^+$ T cells to regulatory T cells and the ratio of conventional T cells to regulatory T cells;

reduction of immune suppressive tumor-associated macrophages (TAMs)

reduction of $CD24^+$, $CD103^+$ and $CD11b^+$, and influx of inflammatory $Ly6^{hi}CD11b^+$ monocytes and $Ly6^{hi}CD11b^-$ myeloid cells into the tumor.

The foregoing one or more immunological effects may serve as early indicators of response of the subject to the treatment and may serve as monitors of the continued effectiveness of same.

Observation of these effects illustrates that the manner in which the present viruses treat tumor is different from that of vaccine vectors harboring tumor antigens (which are not delivered intratumorally but by intramuscular, subcutaneous or, rarely, intravenous route) and also different from that of oncolytic viruses (which cause cytopathy primarily due to viral replication in tumor cells). If apoptosis results pursuant to the present treatment, it is not due to the same mechanism as apoptosis that results or may result from these different modes of action.

In one embodiment, the present disclosure provides a method of treating a subject diagnosed with a solid tumor comprising delivering to the tumor a therapeutic effective amount of the MVA-hFlt3L or MVAΔE3L-hFlt3L and compositions containing either or both.

In one embodiment, the present disclosure provides a method for inducing anti-tumor immunity in a subject diagnosed with cancer comprising administering to the subject a therapeutically effective amount of MVA-hFlt3L or MVAΔE3L-hFlt3L. The methods of the present disclosure include induction of anti-tumor immunity that can reduce the size of the tumor, eradicate the tumor, inhibit growth of the tumor, inhibit metastasis or reduce metastatic growth of the tumor or eradicate metastatic growth of the tumor, induce apoptosis of tumor cells or prolong survival of the subject (compared to untreated or conventionally treated subjects).

In another embodiment, the present disclosure provides a method for enhancing, stimulating, or eliciting, in a subject diagnosed with a solid malignant tumor, an anti-tumor immune response that may include an innate immune response and/or an adaptive immune response such as a T cell response by exposing the tumor to MVA-hFlt3L or MVAΔE3L-hFlt3L in a therapeutically effective amount.

In specific embodiments, the present disclosure provides methods of eliciting an immune response that mediates adaptive immune responses both in terms of T-cell cytotoxicity directed against tumor cells and in terms of eliciting effector T cells also directed against tumor cells. The methods comprise administering to a subject afflicted with a solid tumor intratumorally or (as the present inventors anticipate) intravenously a composition comprising MVA-hFlt3L or MVAΔE3L-hFlt3L wherein administration of said composition results in a tumor-specific immune response against the tumor and, eventually, in reduction, inhibition or eradication of tumor growth, inhibition of metastatic growth, apoptosis of tumor cells and/or prolongation of the subject's survival. Indeed the present inventors have shown that cancer cells are being killed and that the immune response can migrate to remote locations, as would be the case with metastases.

In some embodiments, the present disclosure provides methods of eliciting an immune response that mediates adaptive immune responses both in terms of T-cell cytotoxicity directed against tumor cells and in terms of eliciting effector T cells also directed against tumor cells. The methods comprise administering to a subject parenterally a composition comprising MVA-hFlt3L or MVAΔE3L-hFlt3L wherein administration of said composition results in a tumor-specific immune response against the tumor and, eventually, in reduction, inhibition or eradication of tumor growth and/or in inhibition reduction or elimination of metastatic growth, apoptosis of tumor cells and/or prolongation of survival of the treated subject compared to conventional therapy or no treatment. For intraperitoneal metastases, the virus can be injected intraperitoneally.

Indeed the present inventors have shown that cancer cells are being killed and that the immune response can migrate to remote locations, as would be the case with metastases, and still exert an anti-tumor effect.

Because MVA-hFlt3L and MVAΔE3L-hFlt3L are substantially not replication competent in most mammalian cells, it does not exert its effect on the immune system the same way as replication competent vaccines or vectors. Thus, while it is believed that stimulation of the immune system is a barrier to efficacy for oncolysis (8) (Kim et al., *Nat Rev Cancer*. (1), 64-71 (2009)), MVA-hFlt3L or MVAΔE3L-hFlt3L is able to harness the innate immune system to stimulate adaptive immunity, both in terms of cytotoxicity and more broadly in terms of effector T cell activation against the tumor.

The present disclosure thus provides a method for treating a solid malignant tumor, comprising delivering to a tumor of the subject an amount of MVA-hFlt3L or MVAΔE3L-hFlt3L effective to induce an immune response against the tumor in a subject diagnosed with solid tumor.

The present disclosure also provides a method for generating antitumor systemic immunity in a subject afflicted with a solid malignant tumor, comprising delivering to a tumor of the subject an amount of MVA-hFlt3L or MVAΔE3L-hFlt3L effective to bring about one or both of rejection of non-injected tumors in said subject and inhibition of tumor metastasis (which the present inventors test by tumor rechallenge).

In order to increase the effectiveness of a treatment with the compositions of the present disclosure, the compositions and methods of the present disclosure may be used in combination with replication competent oncolytic viruses. Suitable examples of oncolytic viruses include vaccinia virus, vesicular stomatitis virus, reovirus, adenovirus, Newcastle disease virus and herpes simplex virus. Vaccinia virus infects many types of cells but replicates preferentially in tumor cells due to the fact that tumor cells have a metabolism that favors replication, exhibit activation of certain pathways that also favor replication and create an environment that evades the innate immune system, which also favors viral replication. Specific examples of replication competent viruses that can be used in combination with compositions and methods of the present disclosure include TK deficient vaccinia-based viruses with or without transgene E3LΔ83N-TK, E3L083N-TK-mGM-CSF, and E3LΔ83N-TK-hFlt3L.

In prior work by the present inventors, MVA induced type I IFN induction in conventional dendritic cells (cDCs) via a cytosolic DNA-sensing pathway mediated by cGAS/STING. Intravenous delivery of MVA in C57B/6 mice induced type I IFN in wild-type mice, but not in mice lacking STING or ERF3. They also showed that MVAΔE3L induces higher levels of type I IFN gene expression and phosphorylation of IRF3 than MVA in cDCs. MVAΔE3L is detected by both the cytosolic DNA-sensing pathway mediated by cGAS/STING, and the dsRNA-sensing pathway mediated by MDA5/MAVS. In addition, MVAΔE3L infection of B16 melanoma cells and MC38 colon adenocarcinoma cells induced type I IFN and proinflammatory cytokines and chemokines, as well as activation of phosphorylation of IRF3. Both MVA and MVAΔE3L induce apoptosis in B16 and MC38 cells as demonstrated by the cleavage of PARP and Caspase-3. The present inventors used this work, MVA or MVAΔE3L virus as direct anticancer therapy. Intratumoral injection of MVA or MVAΔE3L in a murine B16 melanoma model lead to apoptosis, prolonged survival and tumor eradication, as well as the generation of systemic anti-tumor immunity. Given the findings described here, including dynamic changes in cellular immune responses both within the tumor and systemically (Examples 4-7), the mechanisms associated with previous findings of the present inventors concerning MVA and MVAΔE3L viruses, are believed to be at work here too.

Thus, based on current literature, and without wishing to be bound by theory, the following mechanisms are believed to contribute to anti-tumor effects of MVA-hFlt3L or MVAΔE3L-hFlt3L: (i) induction of type I IFN responses in immune cells including conventional dendritic cells and macrophages; (ii) induction of type I IFN and proinflammatory cytokines and chemokines in cancer cells; (iii) induction of apoptosis in cancer cells; and (iv) alteration of tumor immune suppressive environment to an immune activating one.

The present disclosure further comprises compositions comprising MVA and a MVAΔE3L, each further modified to express human Flt3L. As shown in Example 1, the inventors have generated recombinant MVA and MVAΔE3L expressing human Flt3L using a strategy depicted in FIG. 1 and involving deletion of a central portion of the TK gene. Accordingly, the viruses and the constructs can be labeled TK⁻.

Modified Vaccinia Ankara (MVA)

Modified Vaccinia Ankara (MVA) virus is a member of the genera Orthopoxvirus in the family of Poxviridae. MVA was generated by approximately 570 serial passages on chicken embryo fibroblasts (CEF) of the Ankara strain of vaccinia virus (CVA) (60) (Mayr et al., *Infection* 3, 6-14 (1975)). As a consequence of these long-term passages, the resulting MVA virus contains extensive genome deletions and is highly host cell restricted to avian cells (61) (Meyer et al., *J. Gen. Virol.* 72, 1031-1038 (1991)). It was shown in a variety of animal models that the resulting MVA is significantly avirulent (57) (Mayr et al., *Dev. Biol. Stand.* 41, 225-34 (1978)).

The safety and immunogenicity of MVA has been extensively tested and documented in clinical trials, particularly against the human smallpox disease. These studies included over 120,000 individuals and have demonstrated excellent efficacy and safety in humans. Moreover, compared to other vaccinia based vaccines, MVA has weakened virulence (infectiousness) while it triggers a good specific immune response. Thus, MVA has been established as a safe vaccine vector, with the ability to induce a specific immune response.

Due to the above mentioned characteristics, MVA became an attractive candidate for the development of engineered MVA vectors, used for recombinant gene expression and vaccines. As a vaccine vector, MVA has been investigated against numerous pathological conditions, including HIV, tuberculosis and malaria, as well as cancer (20, 21) (Sutter et al., *Curr Drug Targets Infect Disord* 3: 263-271(2003); Gomez et al., *Curr Gene Ther* 8: 97-120 (2008)).

It has been demonstrated that MVA infection of human monocyte-derived dendritic cells (DC) causes DC activation, characterized by the upregulation of co-stimulatory molecules and secretion of proinflammatory cytokines (18) (Drillien et al., *J Gen Virol* 85: 2167-2175 (2004)). In this respect, MVA differs from standard wild type Vaccinia virus (WT-VAC), which fails to activate DCs. Dendritic cells can be classified into two main subtypes: conventional dendritic cells (cDCs) and plasmacytoid dendritic cells (pDCs). The former, especially the $CD103^+/CD8\alpha^+$ subtype, are particularly adapted to cross-presenting antigens to T cells; the latter are strong producers of Type I IFN.

Viral infection of human cells results in activation of an innate immune response (the first line of defense) mediated by type I interferons, notably interferon-alpha (a). This normally leads to activation of an immunological "cascade," with recruitment and proliferation of activated T cells (both CTL and helper) and eventually with antibody production. However viruses express factors that dampen immune responses of the host. MVA is a better immunogen than WT-VAC and replicates poorly in mammalian cells. (See, e.g., Brandler et al., *J. Virol.* 84, 5314-5328 (2010)) (62).

However, MVA is not entirely nonreplicative and as the present inventors show contains some residual immunosuppressive activity. Nevertheless, as shown herein MVA significantly prolonged survival of treated subjects. An implication of these findings is that by injecting a tumor with or systemically delivering MVA (or MVAΔE3L) it is possible to enhance a host's innate and adaptive immune responses and thereby overcome the tumor's ability to evade immune responses and to restore the ability of the host to mount an immune response against the tumor whether the response is native or induced or enhanced by another immunotherapeutic agent, such as a checkpoint inhibitor.

Modified Vaccinia Ankara with Deletion of E3 (MVAΔE3L)

The antitumor effects of MVA described in the immediately preceding section are also observed with MVAΔE3L. The latter is less immunosuppressive than MVA and even less replicative in most mammalian cells, and from that point of view preferred. In addition, the effects of MVAΔE3L have generally been qualitatively better than those with MVA as seen in the experiments described herein.

Immune Response

In addition to induction of the immune response by up-regulation of particular immune system activities (such as antibody and/or cytokine production, or activation of cell mediated immunity), immune responses may also include suppression, attenuation, or any other downregulation of detectable immunity, so as to reestablish homeostasis and prevent excessive damage to the host's own organs and tissues. In some embodiments, an immune response that is induced according to the methods of the present disclosure generates effector $CD8^+$ (antitumor cytotoxic $CD8^+$) T cells or activated T helper cells or both that can bring about directly or indirectly the death, or loss of the ability to propagate, of a tumor cell.

Induction of an immune response by the compositions and methods of the present disclosure may be determined by detecting any of a variety of well-known immunological parameters (63, 64) (Takaoka et al., *Cancer Sci.* 94:405-11 (2003); Nagorsen et al., *Crit. Rev. Immunol.* 22:449-62 (2002)). Induction of an immune response may therefore be established by any of a number of well-known assays, including immunological assays, Such assays include, but need not be limited to, in vivo, ex vivo, or in vitro determination of soluble immunoglobulins or antibodies; soluble mediators such as cytokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, altered intracellular cation gradient or concentration (such as calcium); phosphorylation or dephosphorylation of cellular polypeptides; induction of specialized activities such as specific gene expression or cytolytic behavior; cellular differentiation by cells of the immune system, including altered surface antigen expression profiles, or the onset of apoptosis (programmed cell death); or any other criterion by which the presence of an immune response may be detected. For example, cell surface markers that distinguish immune cell types may be detected by specific antibodies that bind to $CD4^+$, $CD8^+$, or NK cells. Other markers and cellular components that can be detected include but are not limited to interferon γ (IFN-γ), tumor necrosis factor (TNF), IFN-α, IL-β, and CCL5. Common methods for detecting the immune response include, but are not limited to flow cytometry, ELISA, immunohistochemistry. Procedures for performing these and similar assays are widely known and may be found, for example in Letkovits (Immunology Methods Manual: The Comprehensive Sourcebook of Techniques, *Current Protocols in Immunology*, 1998).

Pharmaceutical Compositions and Preparations

Pharmaceutical compositions comprising MVA-hFlt3L or MVAΔE3L-hFlt3L may contain a carrier or diluent, which can be a solvent or dispersion medium containing, for example, water, saline, Tris buffer, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be effected by various antibacterial and antifungal agents and preservatives, for example, parabens, chlorobutanol, phenol, sorbic acid, thimerosal, and the like. In many cases, it will be preferable to include isotonic agents, for example, sugars or sodium chloride, and buffering agents. Prolonged absorption of the injectable compositions can be brought about by the use in the compositions of agents delaying absorption, for example, aluminum monostearate and gelatin or carrier molecules. Other excipients may include wetting or emulsifying agents. In general, excipients suitable for injectable preparations can be included as apparent to those skilled in the art.

Pharmaceutical compositions and preparations comprising MVA-hFlt3L or MVAΔE3L-hFlt3L may be manufactured by means of conventional mixing, dissolving, granulating, emulsifying, encapsulating, entrapping or lyophilizing processes. Pharmaceutical viral compositions may be formulated in conventional manner using one or more physiologically acceptable carriers, diluents, excipients or auxiliaries that facilitate formulating virus preparations suitable for in vitro, in vivo, or ex vivo use. The compositions can be combined with one or more additional biologically active agents (for example parallel administration of GM-CSF) and may be formulated with a pharmaceutically acceptable carrier, diluent or excipient to generate pharmaceutical (including biologic) or veterinary compositions of the instant disclosure suitable for parenteral or intra-tumoral administration.

Many types of formulation are possible as is appreciated by those skilled in the art. The particular type chosen is dependent upon the route of administration chosen, as is well-recognized in the art. For example, systemic formulations will generally be designed for administration by injection, e.g., intravenous, as well as those designed for intra-tumoral delivery. Preferably, the systemic or intratumoral formulation is sterile.

Sterile injectable solutions are prepared by incorporating MVA-hFlt3L or MVAΔE3L-hFlt3L in the required amount of the appropriate solvent with various other ingredients enumerated herein, as required, followed by suitable sterilization means. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum drying and freeze-drying techniques, which yield a powder of the virus plus any additional desired ingredient from a previously sterile-filtered solution thereof.

In some embodiments, the MVA-hFlt3L or MVAΔE3L-hFlt3L compositions of the present disclosure may be formulated in aqueous solutions, or in physiologically compatible solutions or buffers such as Hanks's solution, Ringer's solution, mannitol solutions or physiological saline buffer. In certain embodiments, any of the MVA-hFlt3L or MVAΔE3L-hFlt3L compositions may contain formulator agents, such as suspending, stabilizing, penetrating or dispersing agents, buffers, lyoprotectants or preservatives such as polyethylene glycol, polysorbate 80, 1-dodecylhexahydro-2H-azepin-2-one (laurocapran), oleic acid, sodium citrate, Tris HCl, dextrose, propylene glycol, mannitol, polysorbate polyethylenesorbitan monolaurate (Tween®-20), isopropyl myristate, benzyl alcohol, isopropyl alcohol, ethanol sucrose, trehalose and other such generally known in the art may be used in any of the compositions of the instant disclosure. (Pramanick et al., *Pharma Times* 45(3), 65-76 (2013)) (65).

The biologic or pharmaceutical compositions of the present disclosure can be formulated to allow the virus contained therein to be available to infect tumor cells upon administration of the composition to a subject. The level of virus in serum, tumors, and if desired other tissues after administration can be monitored by various well-established techniques, such as antibody-based assays (e.g., ELISA, immunohistochemistry, etc.).

The recombinant viruses of the present invention can be stored at −80° C. with a titer of $3.5 \times 10^7$ PFU/ml formulated in about 10 mM Tris, 140 mM NaCl pH 7.7. For the preparation of vaccine shots, e.g., $10^2$-$10^8$ or $10^2$-$10^9$ viral particles can be lyophilized in 100 ml of phosphate-buffered saline (PBS) in the presence of 2% peptone and 1% human albumin in an ampoule, preferably a glass ampoule. Alternatively, the injectable preparations can be produced by stepwise freeze-drying of the recombinant virus in a formulation. This formulation can contain additional additives such as mannitol, dextran, sugar, glycine, lactose or polyvinylpyrrolidone or other additives such as antioxidants or inert gas, stabilizers or recombinant proteins (e.g., human serum albumin) suitable for in vivo administration. The glass ampoule is then sealed and can be stored between 4° C. and room temperature for several months. However, the ampoule is stored preferably at temperatures below −20° C.

For therapy, the lyophilisate can be dissolved in an aqueous solution, such as physiological saline or Tris buffer, and administered either systemically or intratumorally. The mode of administration, the dose and the number of administrations can be optimized by those skilled in the art in a known manner and are detailed below.

The pharmaceutical composition according to the present disclosure may comprise an additional adjuvant. As used herein, an "adjuvant" refers to a substance that enhances, augments or potentiates the host's immune response to tumor antigens. A typical adjuvant may be aluminum salts, such as aluminum hydroxide or aluminum phosphate, Quil A, bacterial cell wall peptidoglycans, virus-like particles, polysaccharides, toll-like receptors, nano-beads, etc. (Aguilar et al. (2007), Vaccine 25: 3752-3762).

Kits Comprising Recombinant MVA Viruses

The present disclosure contemplates the provision of kits comprising one or more compositions comprising one or more of the recombinant MVAs described herein. The kit can comprise one or multiple containers or vials of the recombinant MVA, together with instructions for the administration of the recombinant MVA to a subject to be treated. The instructions may indicate a dosage regimen for administering the composition or compositions as provided below.

In some embodiments, the kit may also comprise an additional composition comprising a checkpoint inhibitor for conjoint administration with the recombinant MVA composition.

Effective Amount and Dosage of MVA-hFlt3L or MVAΔE3L-hFlt3L

In general, the subject is administered a dosage of MVA-hFlt3L or MVAΔE3L-hFlt3L in the range of about $10^6$ to about $10^{10}$ plaque forming units (pfu), although a lower or higher dose may be administered. In a preferred embodiment, dosage is about $10^7$-$10^9$ pfu. The equivalence of pfu to virus particles can differ according to the specific pfu titration method used. Generally, a pfu is equal to about 5 to 100 virus particles and 0.69 PFU is about 1 TCID50. A therapeutically effective amount of MVA-hFlt3L or MVAΔE3L-hFlt3L can be administered in one or more divided doses for a prescribed period of time and at a prescribed frequency of administration.

For example, as is apparent to those skilled in the art, a therapeutically effective amount of MVA-hFlt3L or MVAΔE3L-hFlt3L in accordance with the present disclosure may vary according to factors such as the disease state, age, sex, weight, and general condition of the subject, and the ability of MVA-hFlt3L or MVAΔE3L-hFlt3L to elicit a desired immunological response in the particular subject (the subject's response to therapy). In delivering MVAhFlt3L or MVAΔE3L-hFlt3L to a subject, the dosage will also vary depending upon such factors as the general medical condition, previous medical history, disease type and progression, tumor burden, the presence or absence of tumor infiltrating immune cells in the tumor, and the like.

In some embodiments, it may be advantageous to formulate compositions of the present disclosure in dosage unit form for ease of administration and uniformity of dosage. "Dosage unit form as used herein" refers to physically discrete units suited as unitary dosages for the mammalian subjects to be treated; each unit containing a predetermined quantity of active material calculated to produce the desired therapeutic effect in association with the required pharmaceutically or veterinary acceptable carrier.

Administration and Therapeutic Regimen of MVA-hFlt3L or MVAΔE3L-hFlt3L

Administration of MVA-hFlt3L and MVAΔE3L-hFlt3L can be achieved using more than one route, including parenteral, for example intratumoral or intravenous, administration. In one embodiment, MVA-hFlt3L or MVAΔE3L-hFlt3L is administered directly into the tumor, e.g. by intratumoral injection, where a direct local reaction is desired. Additionally, administration routes of MVA-hFlt3L or MVAΔE3L-hFlt3L can vary, e.g., first administration using an intratumoral injection, and subsequent administration via an intravenous injection, or any combination thereof. A therapeutically effective amount of MVA-hFlt3L or MVAΔE3L-hFlt3L injection can be administered for a prescribed period of time and at a prescribed frequency of administration. In certain embodiments, MVA-hFlt3L or MVAΔE3L-hFlt3L can be used in conjunction with other therapeutic treatments. For example, MVA-hFlt3L or MVAΔE3L-hFlt3L can be administered in a neoadjuvant (preoperative) or adjuvant (postoperative) setting for subjects inflicted with bulky primary tumors. It is anticipated that such optimized therapeutic regimen will induce an immune response against the tumor, and reduce the tumor burden in a subject before or after primary therapy, such as surgery. Furthermore, MVA-hFlt3L or MVAΔE3L-hFlt3L can be administered in conjunction with other therapeutic treatments such as chemotherapy or radiation.

In certain embodiments, the MVA-hFlt3L or MVAΔE3L-hFlt3L virus is administered at least once weekly or monthly but can be administered more often if needed, such as two times weekly for several weeks, months, years or even indefinitely as long as benefits persist. More frequent administrations are contemplated if tolerated and if they result in sustained or increased benefits. Benefits of the present methods include but are not limited to the following: reduction of the number of cancer cells, reduction of the tumor size, eradication of tumor, inhibition of cancer cell infiltration into peripheral organs, inhibition or stabilization or eradication of metastatic growth, inhibition or stabilization of tumor growth, and stabilization or improvement of quality of life. Furthermore, the benefits may include induction of an immune response against the tumor, activation of effector CD4+ T cells, an increase of effector CD8+ T cells, or reduction of regulatory CD4+ cells. For example, in the context of melanoma or, a benefit may be a lack of recurrences or metastasis within one, two, three, four, five or more years of the initial diagnosis of melanoma. Similar assessments can be made for colon cancer and other solid tumors.

In certain other embodiments, the tumor mass or tumor cells are treated with MVA-hFlt3L or MVAΔE3L-hFlt3L in vivo, ex vivo, or in vitro.

Vectors

In the experiments detailed below a pCB plasmid-based vector was used to insert the specific gene of interest (SG), in this case, murine GM-CSF (mGM-CSF) or human Flt3L (hFlt3L) under the control of the vaccinia synthetic early and late promoter (Pse/l). The methodology for constructing the vector has been described in M. Puhlmann, C. K. Brown, M. Gnant, J. Huang, S. K. Libutti, H. R. Alexander, D. L. Bartlett. Vaccinia as a vector for tumor-directed gene therapy: Biodistribution of a thymidine kinase-deleted mutant. Cancer Gene Therapy, 7(1), 66-73 (2000). The *E. coli* xanthine-guanine phosphoribosyl transferase gene (gpt) under the control of vaccinia P7.5 promoter was used as a drug selection marker. These two expression cassettes were flanked by a partial sequence of TK gene on each side. The choice of a TK gene was a matter of convenience and other suitable loci within the virus could have been used. Homologous recombination that occurred at the TK locus of the plasmid DNA and modified vaccinia virus (MVA) or MVAΔE3L genomic DNA results in the insertion of SG and gpt expression cassettes into the MVA or MVAΔE3L genomic DNA TK locus to generate MVA-mGM-CSF, MVA-hFlt3L, MVAΔE3L-mGM-CSF, MVA-ΔE3L-hFlt3L. The recombinant viruses were enriched in the presence of gpt selection medium including MPA, xanthine and hypoxanthine, and plaque-purified in the presence of the drug selection medium for 4-5 rounds until the appropriate recombinant viruses without contaminating MVA or MVAΔE3L were obtained.

It will be appreciated however, that any other expression vector suitable for integration into the MVA or MVA Δ E3L genome could have been used as well as alternative promoters, regulatory elements, selectable markers, cleavage sites, nonessential insertion regions of MVA. MVA encodes many immune modulatory genes at the ends of the linear genome, including C11, C7, K3, F1, F2, F4, F6, F8, F9, F11, F14.5, J2, A46, C16. These genes can be deleted to potentially enhance immune activating properties of the virus, and allow insertion of transgenes.

EXAMPLES

Materials and Methods Viruses and Cell Lines

MVA and MVAΔE3L viruses were kindly provided by Gerd Sutter (University of Munich), and propagated in BHK-21 (baby hamster kidney cell, ATCC CCL-10) cells. MVA is commercially and/or publicly available. The method of generation of MVAΔE3L Viruses was described (28) (Hornemann et al., *J Virol* 77, 8394-8407 (2003)). The viruses were purified through a 36% sucrose cushion. BHK-21 were cultured in Eagle's Minimal Essential Medium (Eagle's MEM, can be purchased from Life Technologies, Cat #11095-080) containing 10% FBS, 0.1 mM nonessential amino acids (NEAA), and 50 mg/ml gentamycin. The murine melanoma cell line B16-F10 was originally obtained from I. Fidler (MD Anderson Cancer Center). B16-F10 cells were maintained in RPMI 1640 medium supplemented with 10% FBS, 100 Units/ml penicillin, 100 μg/ml streptomycin, 0.1 mM NEAA, 2 mM L-glutamine, 1 mM sodium pyruvate, and 10 mM HEPES buffer. The MC38 colon adenocarcinoma cancer cells were maintained in Dulbecco's modified Eagle medium (DMEM, Invitrogen). Murine triple negative breast cancer cell line 4T1 was cultured in the RPMI medium with 10% FBS. TRAMP-C2 cells are derived from transgenic adenocarcinoma mouse prostate model (TRAMP) in C57BL/6 mice. TRAMP-C2 cells are tumorigenic when grafted into syngenic C57BL/6 mice. TRAMP-C2 cells are available from ATCC. They are cultured in DMEM with 5% of Nu-Serum IV, 5% FBS, bovine insulin, and DHT. All cells were grown at 37° C. in a 5% $CO_2$ incubator.

Cells and cell lines used herein are commercially or publicly available unless otherwise indicated.

Mice

Female C57BL/6J and BALB/c mice between 6 and 8 weeks of age were purchased from the Jackson Laboratory and were used for in vivo tumor implantation and treatment experiments. These mice were maintained in the animal facility at the Sloan Kettering Institute. All procedures were performed in strict accordance with the recommendations in the Guide for the Care and Use of Laboratory Animals of the National Institute of Health. The protocol was approved by the Committee on the Ethics of Animal Experiments of Sloan Kettering Cancer Institute.

Batf3$^{-/-}$ and STING$^{Gt/Gt}$ mice were generated in the laboratories Kenneth Murphy (Washington University; Batf3$^{-/-}$), and Russell Vance (University of California, Berkeley; STING$^{Gt/Gt}$). These mice were bred and maintained in the animal facility at the Sloan Kettering Institute.

Bilateral Tumor Implantation Model and Intratumoral Injection with Recombinant MVA or MVAΔE3L Viruses Expressing mGM-CSF or hFlt3L Briefly, B16-F10 melanoma cells were implanted intradermally to the left and right flanks of C57B/6 mice ($5 \times 10^5$ to the right flank and $1 \times 10^5$ to the left flank). 8 days after tumor implantation, the larger tumors on the right flank were intratumorally injected with $2 \times 10^7$ pfu of MVAΔE3L-hFlt3L, MVAΔE3L-mGM-CSF, MVAΔE3L, or Heat-inactivated MVA twice weekly when the mice were under anesthesia. Mice were monitored daily and tumor sizes were measured twice a week. Tumor volumes were calculated according the following formula: l (length)×w (width)×h (height)/2. Mice were euthanized for signs of distress or when the diameter of the tumor reached 10 mm.

In some experiments, MC38 colon adenocarcinoma cells were implanted intradermally to the left and right flanks of C57B/6 mice ($5 \times 10^5$ to the right flank and $1 \times 10^5$ to the left flank). Tumors were allowed to grow for 7-8 days, after which MVAΔE3L-hFlt3L or MVAΔE3L ($2 \times 10^7$ pfu) or PBS control were injected into the larger tumors twice a week. Tumor sizes were measured and the survival of mice was monitored.

In some experiments, 4T1 murine triple negative breast cancer (TNBC) cells were implanted intradermally to the left and right flanks of BALB/c mice ($2.5 \times 10^5$ to the right flank and $5 \times 10^4$ to the left flank). 5 days post tumor implantation, the larger tumors on the right flank were injected with either MVAΔE3L or MVAΔE3L-hFlt3L ($2 \times 10^7$ pfu) twice weekly. Mice were monitored daily and tumor sizes were measured twice a week. The survival of mice was monitored.

Bilateral Tumor Implantation Model and Intratumoral Injection with Viruses in the Presence or Absence of Systemic or Intratumoral Administration of Immune Checkpoint Blockade B16-F10 melanoma cells were implanted intradermally to the left and right flanks of C57B/6 mice ($5 \times 10^5$ to the right flank and $1 \times 10^5$ to the left flank). 8 days after tumor implantation, the mice with bilateral tumors were treated with intratumoral injection of MVAΔE3L-hFlt3L to the larger tumors on the right flank and intraperitoneal delivery of immune checkpoint blockade antibodies twice weekly, including anti-CTLA-4 (100 μg per mouse), anti-PD-1 (250 μg per mouse), anti-PD-L1 (250 μg per mouse), or isotype control (100 μg per mouse). The tumor sizes were measured and the tumors were injected twice a week. The survival of mice was monitored.

In some experiments, STING$^{Gt/Gt}$, Batf3$^{-/-}$ mice and WT age-matched controls were used for bilateral B16-F10 melanoma implantation, and treated with PBS or Heat-MVA to the larger tumors on the right flank of the mice.

Unilateral Intradermal Tumor Implantation and Intratumoral Injection with Viruses B16-F10 melanoma ($5 \times 10^5$ cells in a volume of 50 μl) were implanted intradermally into the shaved skin on the right flank of WT C57BL/6J mice. After 8-9 days post implantation, tumor sizes were measured and tumors that are 5-6 mm in diameter were injected with MVAΔE3L-hFlt3L ($2 \times 10^7$ pfu of MVA in a volume of 50 μl), or Heat-MVA, or poly (I:C) (50 μg per mouse) or with PBS when the mice were under anesthesia twice weekly. Mice were monitored daily and tumor sizes were measured twice a week. Tumor volumes were calculated according the following formula: l (length)×w (width)×h(height)/2. Mice were euthanized for signs of distress or when the diameter of the tumor reached 15 mm.

In some experiments, B16-F10 melanoma ($5 \times 10^5$ cells in a volume of 50 μl) were implanted intradermally into the shaved skin on the right flank of WT C57BL/6J mice. After 8-9 days post implantation, tumor sizes were measured and tumors that are 5-6 mm in diameter were injected with PBS, or MVAΔE3L-hFlt3L in the presence of isotype control, anti-CTLA-4, anti-PD-1, or anti-PD-L1 delivered intraperitoneally. The tumor sizes were measured and the tumors were injected twice a week. The survival of mice was monitored. Mice were euthanized for signs of distress or when the diameter of the tumor reached 15 mm.

In some experiments, TRAMP-C2 cells were implanted intradermally to the shaved right flank of STING$^{Gt/Gt}$ mice and age-matched WT C57B/6 controls ($1 \times 10^6$ cells in 50 μl of PBS per mouse). 17 days post tumor implantation, the tumors (around 3-4 mm in diameter) on the right flank were injected with either PBS or MVAΔE3L-hFlt3L ($2 \times 10^7$ pfu) twice weekly. Mice were monitored daily and tumor sizes were measured twice weekly. The survival of mice was monitored.

Preparation of Tumor Cell Suspensions, RNA Isolation, and Real-Time PCR

Briefly, $2.5 \times 10^5$ B16-F10 melanoma cells were intradermally implanted to the left flank and $5 \times 10^5$ B16-F10 melanoma cells to the right flank of 6-8 weeks old C57B/6 mice. 7 days post-implantation, MVA ($2 \times 10^7$ pfu) or Heat-MVA, or PBS was injected into the larger tumors on the right flank. The injection was repeated three days later. Both the injected and non-injected tumors were harvested on day 7 after first injection, and cell suspensions were generated.

RNA was extracted from whole-cell lysates with an RNeasy Mini kit (Qiagen) and was reverse transcribed with a First Strand cDNA synthesis kit (Fermentas). Quantitative real-time PCR was performed in triplicate with SYBR Green PCR Mater Mix (Life Technologies) and Applied Biosystems 7500 Real-time PCR Instrument (Life Technologies)

using gene-specific primers. Relative expression was normalized to the levels of glyceraldehyde-3-phosphate dehydrogenase (GAPDH).

Flow Cytometry

To analyze immune cell phenotypes and characteristics in the tumors or tumor draining lymph nodes, we generated cell suspensions prior to FACS analysis according to the following protocol (Zamarin et al., *Science Translational Medicine* 6, 226-232 (2014)). First we isolated tumors using forceps and surgical scissors three days post treatment with MVA or PBS. The tumors were then weighed. Tumors or tumor draining lymph nodes were minced prior to incubation with Liberase (1.67 Wünsch U/ml) and DNase (0.2 mg/ml) for 30 minutes at 37° C. Cell suspensions were generated by repeated pipetting, filtered through a 70-µm nylon filter, and then washed with complete RPMI prior to Ficoll purification to remove dead cells. Cells were processed for surface labeling with anti-CD3, CD45, CD4, and CD8 antibodies. Live cells are distinguished from dead cells by using fixable dye eFluor506 (eBioscience). They were further permeabilized using FoxP3 fixation and permeabilization kit (eBioscience), and stained for Ki-67, FoxP3, and Granzyme B. For the staining of the myeloid cell population, Fluorochromeconjugated antibodies against CD45.2 (104), CD11b (M1/70), Ly-6C (HK1.4), MHC II (M5/114.15.2), CD24 (M1/69), F4/80 (BM8), CD103 (2E7) and CD11c (N418) were purchased from eBioscience. All antibodies were tested with their respective isotype controls. Data were acquired using the LSRII Flow cytometer (BD Biosciences). Data were analyzed with FlowJo software (Treestar).

ELISPOT

Mouse spleens from nave or treated mice were harvested and mechanically disrupted, and RBCs were lysed. $CD8^+$ T cells were positively selected by incubation with magnetic anti-$CD8^+$ beads (Miltenyi Biotec). BD mouse IFN-γ ELISPOT set was used according to manufacturer's instruction. Briefly, ELISPOT plates were coated with 100 µl anti-mouse IFN-γ antibody in PBS and incubated at 4° C. overnight. Plates were washed with PBS to remove unbound antibody and were blocked with RPMI media with 7% fetal bovine serum for 2 hours at room temperate. $1 \times 10^5$ Purified $CD8^+$ T cells were mixed with equal number of irradiated B16 or MC38 cells, and seeded into each well. The plates were incubated at 37° C. for 16 hours. After incubation, plates were extensively washed with PBS plus 0.05% Tween and incubated with 100 µl/well of biotinylated detection antibody against mouse IFN-γ. Enzyme conjugate (Streptavidin-HRP) was added after wash, followed with adding final substrate solution for spot development. Spots were counted with an Automated ELISPOT Reader System with KS software (Carl Zeiss Inc.)

TRP-2 Tetramer Staining

Tumor draining lymph nodes were isolated and minced prior to incubation with Liberase (1.67 Wunsch U/ml) and DNase (0.2 mg/ml) for 30 minutes at 37° C. Cell suspensions were generated by repeated pipetting, filtered through a 70-µm nylon filter, and then washed with complete RPMI. Lymph node cell suspensions were incubated for 30 mins at room temperature with anti-FcγR II (2.4G2) antibody and 10 µL of PE-H-2 Kb TRP2 (tyrosinase related protein-2) (SVYDFFVWL) tetramer (MBL), followed by staining at 4° C. for 30 mins with anti-CD3 and anti-CD8 antibodies. Cells were washed in MACS buffer (Miltenyi) and analyzed with a BD LSRII, using FlowJo software (Tree Star).

Reagents

The commercial sources for reagents were as follows: Therapeutic anti-CTLA4 (clone 9H10 and 9D9), anti-PD1 (clone RMP1-14), anti-PD-L1 (clone 10F.9G2) were purchased from BioXcell; Antibodies used for flow cytometry were purchased from eBioscience (CD45.2 Alexa Fluor 700, CD3 PE-Cy7, CD4 APC-efluor780, CD8 PerCP-efluor710), Invitrogen (CD4 QDot 605, Granzyme B PE-Texas Red, Granzyme B APC). Fluorochromeconjugated antibodies against CD45.2 (104), CD11b (M1/70), Ly-6C (HK1.4), MHC II (M5/114.15.2), CD24 (M1/69), F4/80 (BM8), CD103 (2E7) and CD11c (N418) were purchased from eBioscience.

Statistics

Two-tailed unpaired Student's t test was used for comparisons of two groups in the studies. Survival data were analyzed by log-rank (Mantel-Cox) test. The p values deemed significant are indicated in the figures as follows: *, $p<0.05$; , $p<0.01$; *, $p<0.001$; ****, $p<0.0001$. The numbers of animals included in the study are discussed in each figure legend.

Example 1

Generation of Recombinant MVA or MVAΔE3L Viruses Expressing mGM-CSF or hFlt3L

Figure 1:
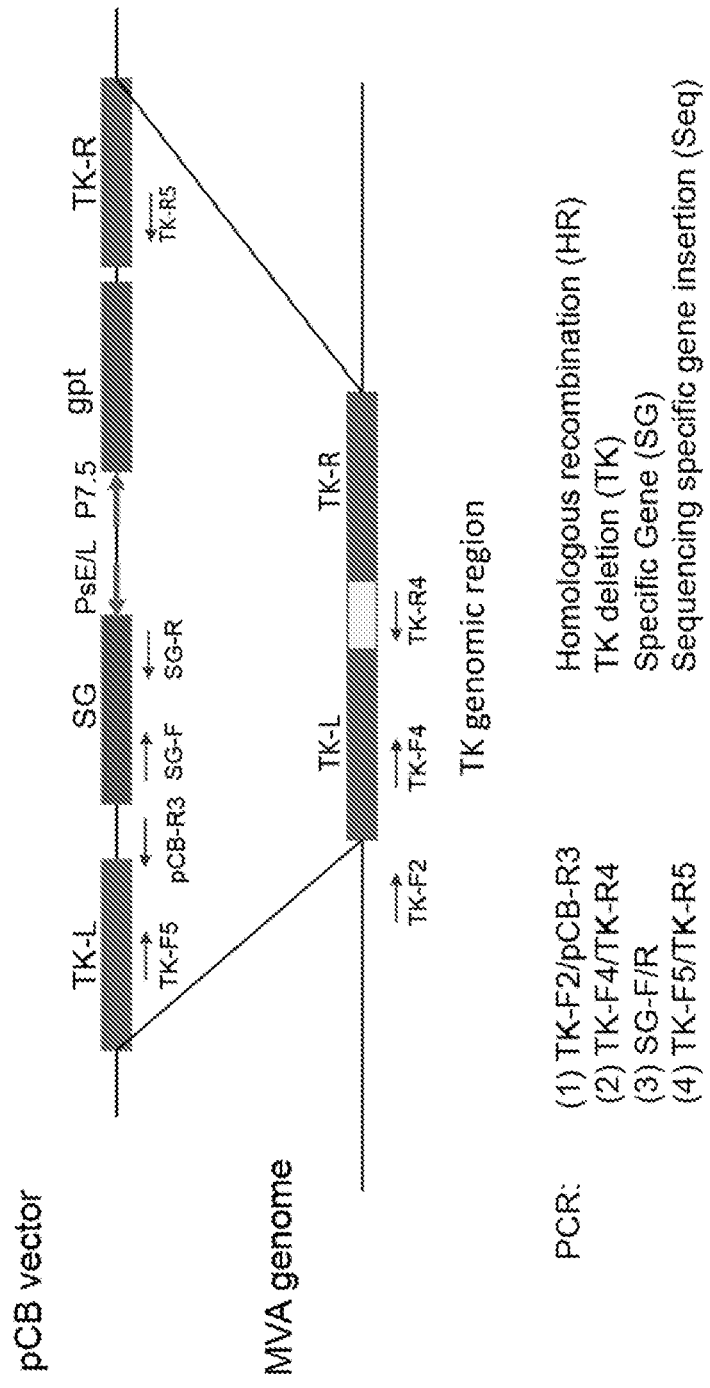
FIG. 1 is a schematic diagram of homologous recombination between plasmid DNA pCB vector and MVA viral genomic DNA at the thymidine kinase (TK) locus. pCB plasmid was used to insert specific gene of interest (SG), in this case, murine GM-CSF (mGM-CSF) or human Flt3L (hFlt3L) under the control of the vaccinia synthetic early and late promoter (Pse/1). The *E. coli* xanthine-guanine phosphoribosyl transferase gene (gpt) under the control of vaccinia P7.5 promoter was used as a drug selection marker. These two expression cassettes were flanked by partial sequence of TK gene (TK-L and TK-R) on each side. The plasmid DNA lacking SG was used as a vector control. Homologous recombination that occurred at the TK locus of the plasmid DNA and modified vaccinia virus (MVA) or MVAΔE3L (with deletion of E3L gene) genomic DNA results in the insertion of SG and gpt expression cassettes into the MVA or MVAΔE3L genomic DNA TK locus to generate MVA-mGM-CSF, MVA-hFlt3L, MVAΔE3L-mGM-CSF, MVA-ΔE3L-hFlt3L. The recombinant viruses were enriched in the presence of gpt selection medium including mycophenolic acid (MPA), xanthine and hypoxanthine, and plaque purified in the presence of the drug selection medium for 4-5 rounds until the appropriate recombinant viruses without contaminating MVA or MVAΔE3L were obtained.

In the present disclosure, the inventors generated recombinant MVA or MVAΔE3L viruses comprising a TK-deletion with and without expressing human Flt3L or murine GM-CSF under the vaccinia synthetic early/late promoter (Pse/1) using standard recombinant virus technology. First, the inventors constructed a plasmid containing specific gene of interest (SG) under the control of the vaccinia Pse/1 as well as the *E. coli* xanthine-guanine phosphoribosyl transferase gene (gpt) under the control of vaccinia P7.5 promoter flanked by the thymidine kinase (TK) gene on either side (FIG. 1).

Figure 2:
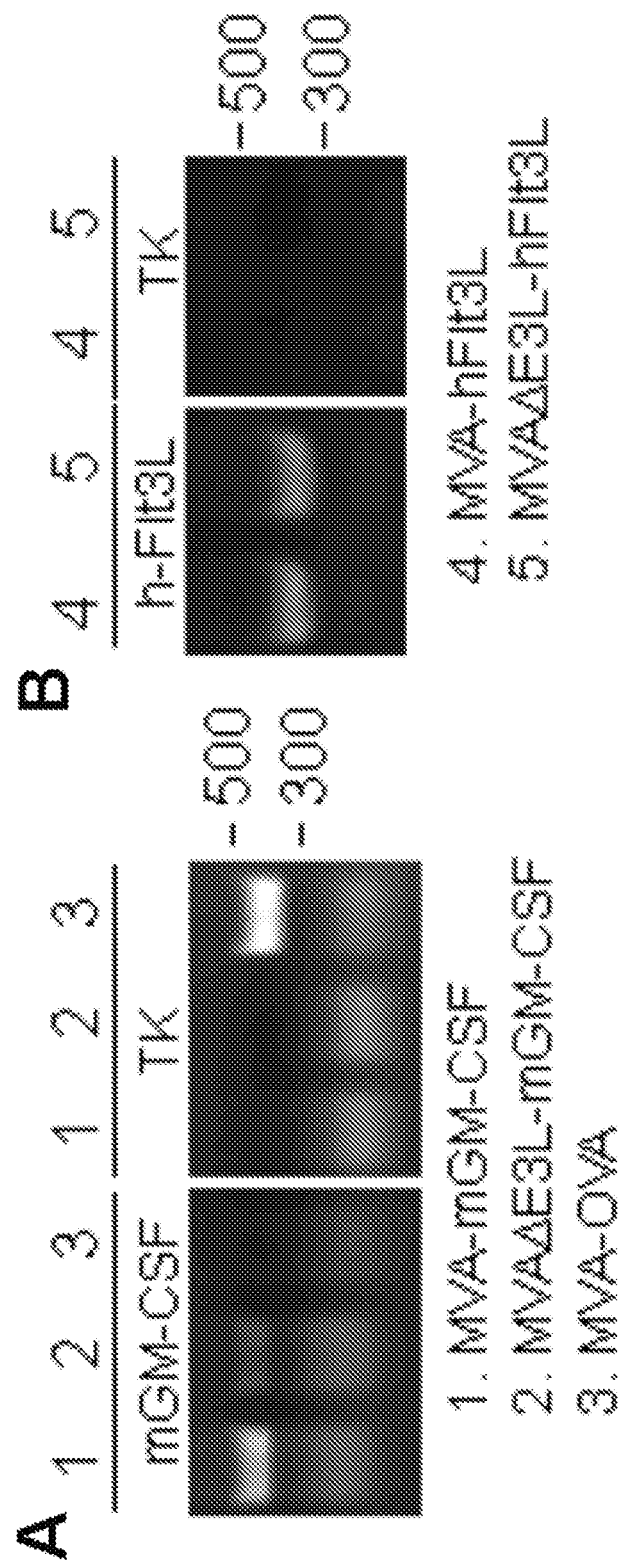
FIG. 2 shows a PCR analysis of recombinant viruses-demonstrating successful generation of MVA or MVAΔE3L recombinant viruses including MVA-mGM-CSF, MVA-hFlt3L, MVAΔE3L-mGM-CSF, and MVA-ΔE3L-hFlt3L. Viral genomic DNAs were analyzed by PCR to verify the insertions of transgenes and deletion of TK, and to make sure there were no contaminating patent viruses, MVA or MVAΔE3L. The PCR products including the inserted transgenes were sequenced to make sure the inserted genes have the correct sequences.

BHK21 cells were infected with MVA or MVAΔE3L at a MOI of 0.05 for 1 h, and then were transfected with the plasmid DNAs described above. The infected cells were collected at 48 h. Recombinant viruses were selected through further culturing in gpt selection medium including MPA, xanthine and hypoxanthine, and plaque purified (Lorenzo et al., 2004). PCR analysis was performed to identify recombinant viruses with loss of part of the TK gene and with and without murine GM-CSF, or human Flt3L, (FIG. 2).

PCR was used to verify the correct insertions in the recombinant viruses MVA-mGM-CSF, MVAΔE3L-mGM-CSF, MVA-hFlt3L, and MVAΔE3L-hFlt3L. Primer pair mGM-CSF-F1/R1 was used to amplify a 310 bp DNA fragment from mGM-CSF gene inserted in recombinant viruses MVA-mGM-CSF or MVAΔE3L-mGM-CSF. hFlt3L gene insertion in MVA-hFlt3L and MVAΔE3L-hFlt3L was verified with primer pair hFlt3L-F4/R4, which can amplify a 316 bp DNA fragment. Primer pair TK-F4/TK-R4 was used to verify the specific gene insertions in the TK locus. TK-F4/R4 can amplify a 304 bp DNA fragment from MVA or MVAΔE3L, but not in MVA-mGM-CSF, MVAΔE3L-mGM-CSF, MVA-hFlt3L, or MVAΔE3L-hFlt3L viruses due to the deletion of TK-R4 primer locus.

Primer sequences:
TK-F2 (SEQ ID NO: 1):
TGTGAAGACGATAAATTAATGATC;

TK-F4 (SEQ ID NO: 2):
TTGTCATCATGAACGGCGGA;

TK-R4 (SEQ ID NO: 3):
TCCTTCGTTTGCCATACGCT;

TK-F5 (SEQ ID NO: 4):
GAACGGGACTATGGACGCAT;

TK-R5 (SEQ ID NO: 5):
TCGGTTTCCTCACCCAATCG;

pCB-R3 (SEQ ID NO: 6):
ACCTGATGGATAAAAAGGCG;

mGMCSF-F1 (SEQ ID NO: 7):
GGCATTGTGGTCTACAGCCT;

mGMCSF-R1 (SEQ ID NO: 8):
GTGTITCACAGTCCUTTTCCG;

hFlt3L-F1 (SEQ ID NO: 9):
AACGACCTATCTCCTCCTGC;

hFlt3L-R1 (SEQ ID NO: 10):
GGGCTGAAAGGCACATTTGG.

Example 2

Figure 3A:
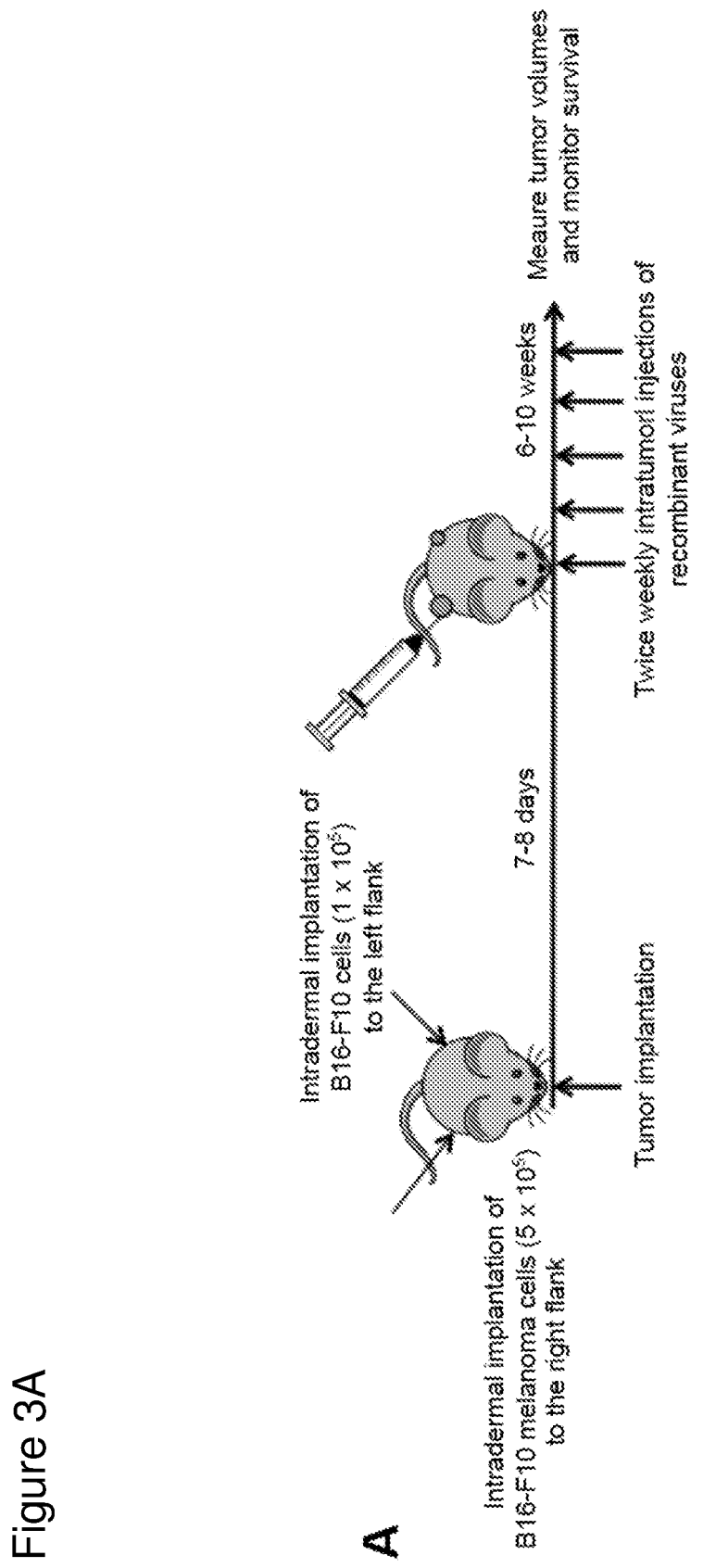
FIG. 3 is a series of graphical representations of data showing that intratumoral injection of MVAΔE3L-hFlt3L is more effective than MVAΔE3L-mGM-CSF, or MVAΔE3L without hFlt3L insert in eradicating both injected and non-injected tumors in a bilateral B16-F10 tumor implantation model. (A) Schematic diagram of bilateral tumor implantation model. B16-F10 melanoma cells were implanted intradermally to the left and right flanks of C57B/6 mice ($5\times10^5$ to the right flank and $1\times10^5$ to the left flank). 7-8 days after tumor implantation, we intratumorally inject $2\times10^7$ pfu of MVAΔE3L, MVAΔE3L-mGM-CSF, MVAΔE3L-hFlt3L viruses, or PBS mock injection control to the larger tumors on the right flank. The tumor sizes were measured and the tumors were injected with recombinant virus or PBS twice a week. The survival of mice was monitored. (B) Volumes of injected and non-injected tumors over days after injections with PBS, MVAΔE3L, MVAΔE3L-mGM-CSF, or MVAΔE3L-hFlt3L viruses. (C) Kaplan-Meier survival curve of tumor-bearing mice treated with PBS (n=5), MVAΔE3L (n=9), MVAΔE3L-mGM-CSF (n=9), or MVAΔE3L-hFlt3L (n=9; *, $p<0.05$; ***, $p<0.001$). (D) Kaplan-Meier survival curve of nave mice (filled circles; n=5) and MVAΔE3L-hFlt3L-treated mice (filled diamonds; n=4) re-challenged intradermally with a lethal dose of MC38 colon adenocarcinoma cells ($1\times10^5$).
Figure 3B:
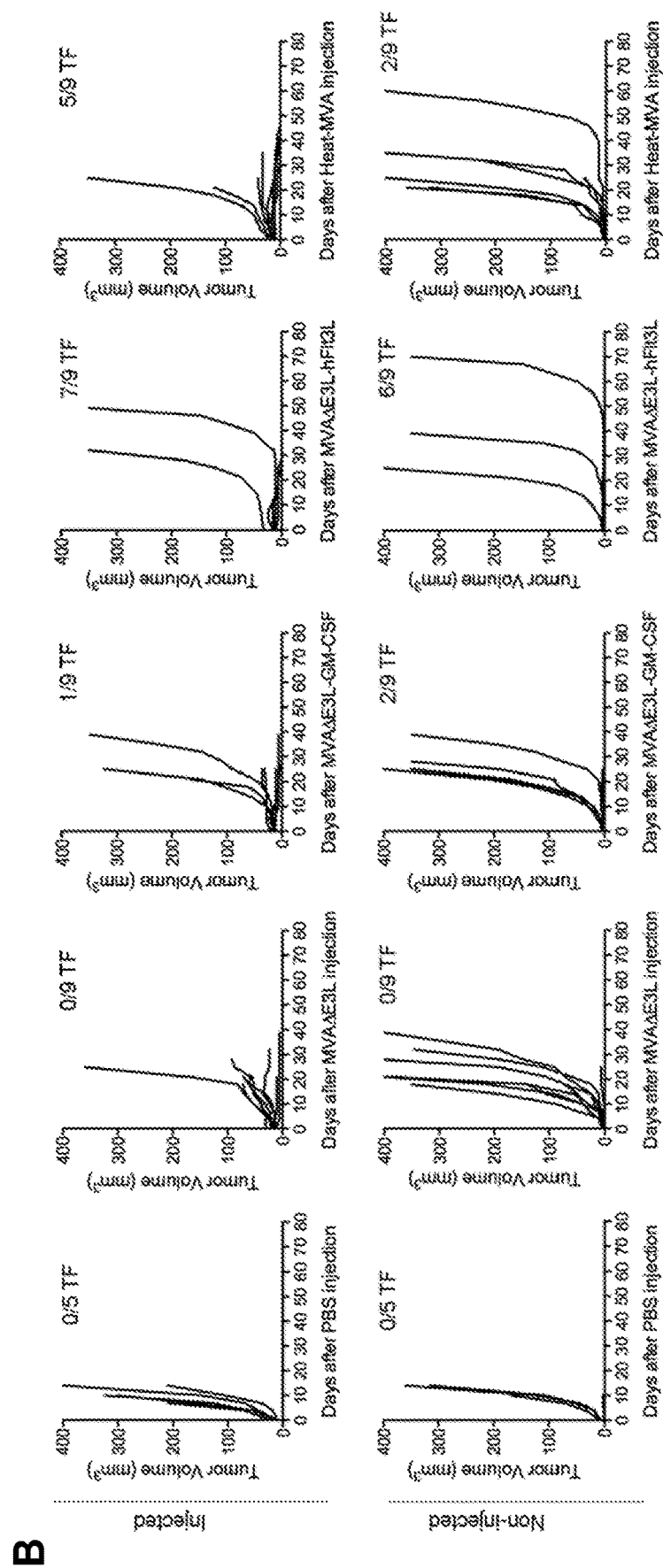
Figure 3C:
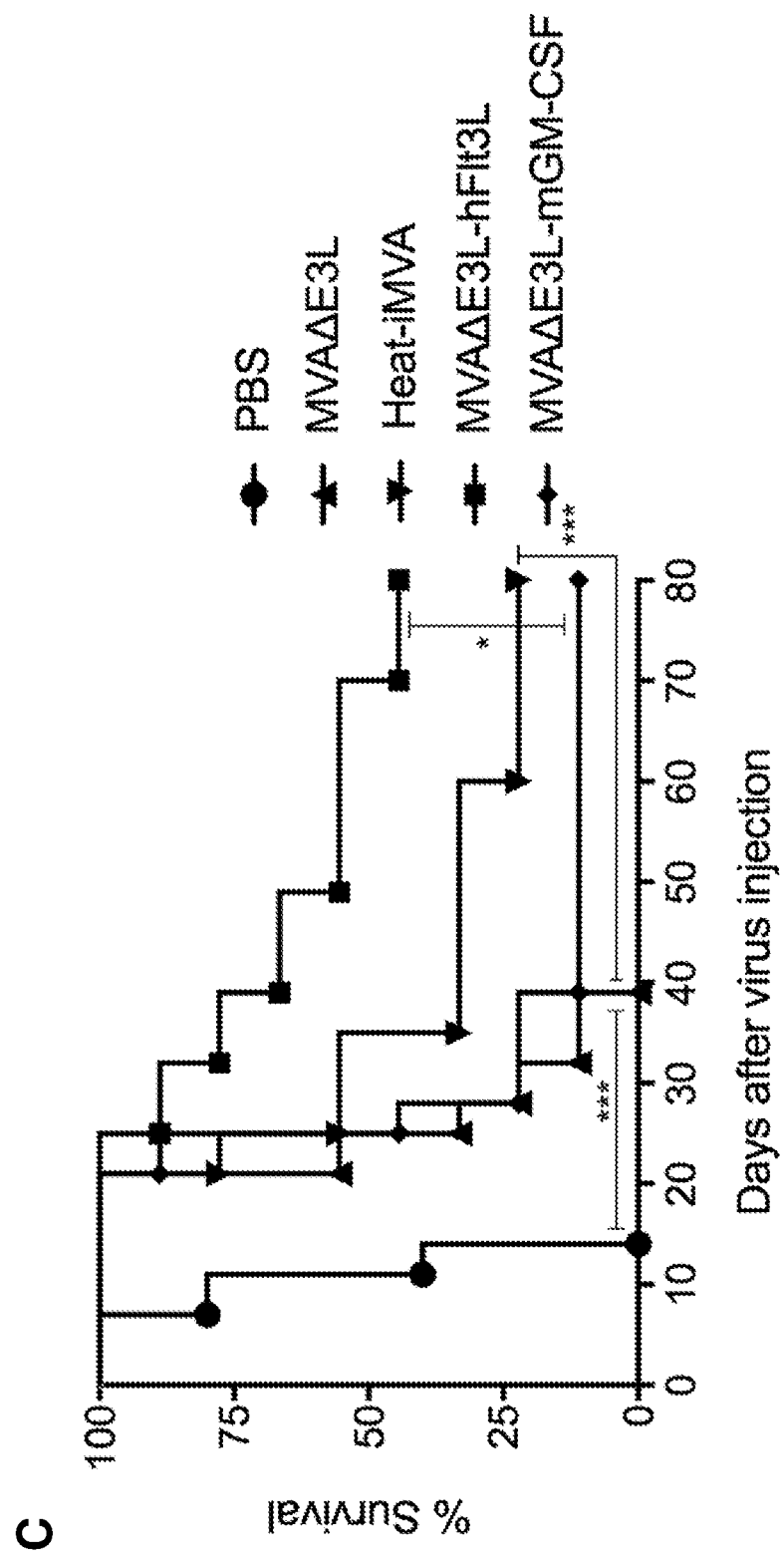

Intratumoral Injection of MVAΔE3L-hFlt3L is More Effective than MVAΔE3L-mGM-CSF or MVAΔE3L in Eradicating or Delaying the Growth of Both Injected and Non-Injected Tumors in a Bilateral B10-F10 Melanoma Model The inventors investigated the effects of intratumoral injection of MVAΔE3L-hFlt3L, MVAΔE3L-mGM-CSF, and MVAΔE3L on metastatic growth using a murine B16-F10 melanoma bilateral implantation model. Briefly, B16-F10 melanoma cells were implanted intradermally to the left and right flanks of C57B/6 mice ($5 \times 10^5$ to the right flank and $1 \times 10^5$ to the left flank). 7-8 days after tumor implantation, the inventors intratumorally injected MVAΔE3L-hFlt3L, MVAΔE3L-mGM-CSF, and MVAΔE3L ($2 \times 10^7$ pfu) or PBS to the larger tumors on the right flank twice weekly. The tumor sizes were measured and the survival of mice was monitored (FIG. 3A). Whereas the PBS-treated mice died quickly with increasing tumor growth over the next 7-14 days (FIGS. 135BA and CB), mice treated with MVAΔE3L exhibited delayed tumor growth of both the injected and non-injected tumors at the contralateral side, which led to the extension of mean survival from 11 days in the PBS group to 25 days in the MVAΔE3L-treated group (FIGS. 3B and C, *, P<0.001 for MVAΔE3L (n=9) vs. PBS (n=5)). In addition, mice treated with MVAΔE3L-mGM-CSF also had a median survival of 25 days and 1/9 mice were cured of melanoma. Furthermore, mice treated with MVAΔE3L-hFlt3L had a median survival of 70 days and 4/9 mice were cured (FIGS. 3B and C, *, P<0.001 for MVAΔE3L-hFlt3L (n=9) vs. MVAΔE3L (n=9); *, P<0.05 for MVAΔE3L-hFlt3L (n=9) vs. MVAΔE3L-mGM-CSF (n=9)). Taken together, these results indicate that intratumoral injection of MVAΔE3L-hFlt3L is more effective than MVAΔE3L-mGM-CSF or MVAΔE3L in eradicating or delaying the growth of both injected and non-injected tumors in a bilateral B16-F10 melanoma model, which imitates a metastatic setting in patients.

Example 3

Figure 3D:
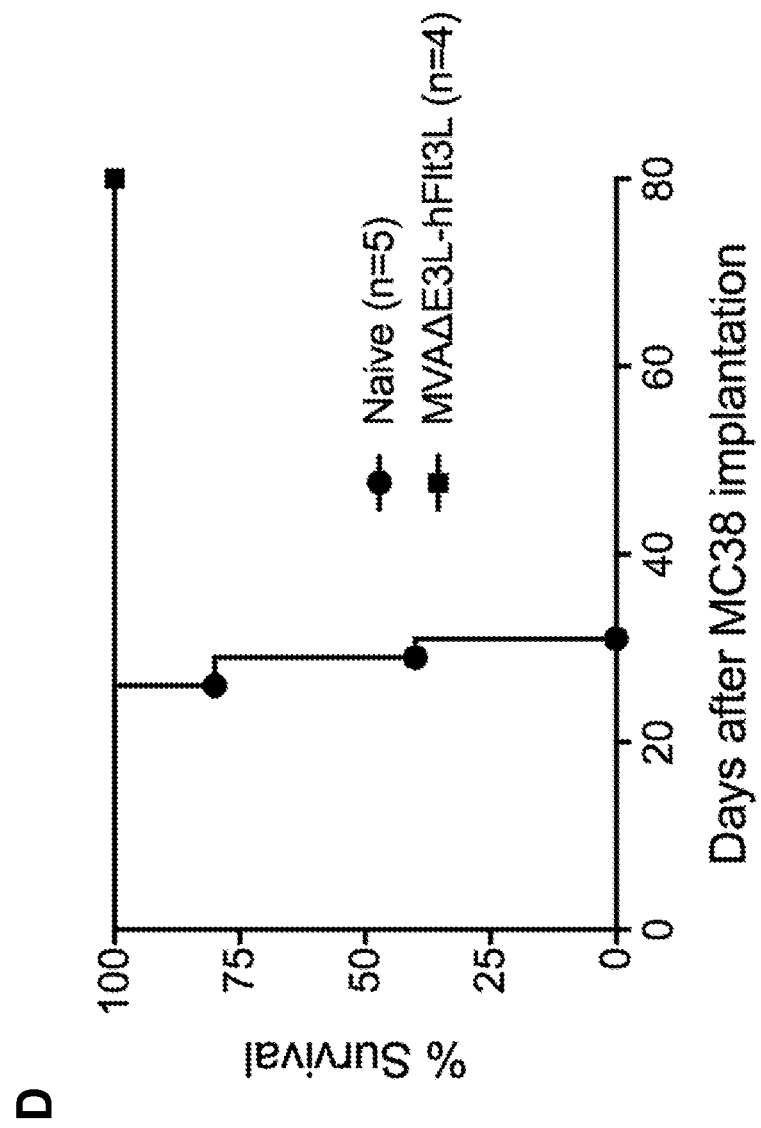

Intratumoral Injection of MVAΔE3L-hFlt3L Leads to Systemic Immunity Against a Different Tumor Type Upon Rechallenge To assess whether the surviving mice (n=4) post intratumoral injection of MVAΔE3L-hFlt3L have developed immunity against a different tumor type, we rechallenged them with a lethal dose of MC38 ($1 \times 10^5$) implanted intradermally. Nave mice (n=5) that have never exposed to the said tumors or viruses were used as a control. Whereas all of the naïve mice developed tumors and died at 26-31 days post tumor implantation with a median survival of 29 days, all of the MVAΔE3L-hFlt3L-treated surviving mice rejected MC38 tumor challenge (FIG. 3D). That is quite remarkable, given that the mice were never exposed to MC38 tumors before. These results suggest that intratumoral injection with MVAΔE3L-hFlt3L allows recognition of common antigens between B16-F10 melanoma and MC38 colon cancers and the development of anti-tumor immunity against different types of tumors.

Example 4

Intratumoral Injection of MVAΔE3L-hFlt3L is Effective in the Proliferation and Activation of CD8$^+$ and CD4$^+$ T Cells and Reduction of Regulatory T Cells in Both Injected and Non-Injected Tumors To assess whether intratumoral injection of MVAΔE3L, MVAΔE3L-mGM-CSF, MVAΔE3L-hFlt3L, or Heat-MVA in B16-F10 melanomas leads to activation and proliferation of CD8$^+$ and CD4$^+$ T cells, $2.5 \times 10^5$ B16-F10 melanoma cells were intradermally implanted to the left flank and $5 \times 10^5$ B16-F10 melanoma cells to the right flank of 6-8 weeks old C57B/6 mice. 7 days post-implantation, MVAΔE3L, MVAΔE3L-mGM-CSF, MVAΔE3L-hFlt3L, or Heat-MVA or PBS was injected into the larger tumors on the right flank. The injection was repeated three days later. Both the injected and non-injected tumors were harvested on day 7 after first injection, and cell suspensions were generated. The live immune cell infiltrates in the injected and non-injected tumors were analyzed by FACS. There was a dramatic increase in CD8$^+$ T cells expressing Granzyme B in the injected tumors, from 58.9% in PBS-treated tumors to 97% in MVAΔE3L-hFlt3L-treated tumors (p<0.0001; FIG. 4 A, 4B). In the non-injected tumors, there was also as increase in CD8$^+$ T cells expressing Granzyme B from 61.9% in PBS-treated mice to 91.6% in MVAΔE3L-hFlt3L-treated and 83% in MVAΔE3L-treated mice (p<0.001; FIG. 4 A, 4B). The difference in the percentage of CD8$^+$ T cells expressing Granzyme B in non-injected tumors between MVAΔE3L-hFlt3L and MVAΔE3L-treated mice was statistically significant (p<0.05; FIG. 4 A, 4B).

In the injected tumors, Ki-67$^+$ CD8$^+$ T cells increased from 58.3% in PBS-treated tumors to 83.2% in MVAΔE3L-hFlt3L-treated tumors (p<0.01; FIG. 4C, 4D). In the non-injected tumors, there was also as increase in CD8$^+$ T cells expressing Ki-67 from 58.7% in PBS-treated mice to 75.4% in MVAΔE3L-hFlt3L-treated mice (p<0.01; FIG. 4C, D).

Similar changes were observed for CD4$^+$ T cells in the injected and non-injected tumors from mice treated with virus compared with those treated with PBS; Granzyme B$^+$ CD4$^+$ T cells rose from 20% in PBS-treated tumors to 98.4% in MVAΔE3L-hFlt3L-treated tumors (P=0.0002; FIG. 5A, 5B). In the non-injected tumors, there was also as increase in CD4+ T cells expressing Granzyme B from 18.7% in PBS-treated mice to 67.8% in MVAΔE3L-hFlt3L-treated and 45.2% in MVAΔE3L-treated mice (p<0.0001; PBS vs. MVAΔE3L-hFlt3L; p<0.01; PBS vs. MVAΔE3L, p<0.05; MVAΔE3L-hFlt3L vs. MVAΔE3L FIG. 5A, 5B).

In addition, there was an increase Ki-67+ CD4+ T cells from 40% in PBS-treated tumors to 59.6% in MVAΔE3L-treated tumors and 66.6% in MVAΔE3L-hFlt3L-treated tumors (p<0.001; PBS vs. MVAΔE3L-hFlt3L, p<0.01; PBS vs. MVAΔE3L, p<0.05; MVAΔE3L-hFlt3L vs. MVAΔE3L, FIG. 5C, D). In the non-injected tumors, there was also as increase in CD4+ T cells expressing Ki-67 from 40% in PBS-treated mice to 61.2% in MVAΔE3L-hFlt3L-treated and 52.2% in MVAΔE3L-treated mice (p<0.01; PBS vs. MVAΔE3L, p<0.05; PBS vs. MVAΔE3L-hFlt3L, FIG. 5C, 5D).

In the injected tumors, CD4+ Foxp3+ T cells decreased from 45.1% in PBS-treated tumors to 26.6% in MVAΔE3L-hFlt3L-treated tumors (p<0.001; FIG. 6A, 6B). In the non-injected tumors, CD4+ Foxp3+ T cells decreased from 51.6% in PBS-treated mice to 37.1% in MVAΔE3L-hFlt3L-treated tumors (p<0.01; FIG. 6A, 6B).

The inventors determined the absolute numbers of CD45+ cells, CD8+ cells in both injected and non-injected tumors after virus treatment. It was found that in the injected tumors, intratumoral injection of MVAΔE3L-hFlt3L or MVAΔE3L increased the CD45+ cells from $3.8 \times 10^6$/g to $1.6 \times 10^7$/g or $1.3 \times 10^7$/g, respectively (P<0.01, MVAΔE3L-hFlt3L vs. PBS; P<0.01, MVAΔE3L vs. PBS; FIG. 7A). In the non-injected tumors, intratumoral injection of MVAΔE3L-hFlt3L or MVAΔE3L at the contralateral tumors increased the CD45+ cells from $3.3 \times 10^6$/g to $9.5 \times 10^7$/g or $5.4 \times 10^7$/g, respectively (P<0.05, MVAΔE3L-hFlt3L vs. MVAΔE3L; P<0.05, MVAΔE3L-hFlt3L vs. PBS; FIG. 7A).

The inventors also found that in the injected tumors, intratumoral injection of MVAΔE3L-hFlt3L or MVAΔE3L increased the CD8+ cells from $2.9 \times 10^5$/g to $2.9 \times 10^6$/g or $2.0 \times 10^6$/g, respectively (P<0.01, MVAΔE3L vs. PBS; P<0.001, MVAΔE3L-hFlt3L vs. PBS; FIG. 7B). In the non-injected tumors, intratumoral injection of MVAΔE3L-hFlt3L or MVAΔE3L at the contralateral tumors increased the CD8+ cells from $2.8 \times 10^5$/g to $1.6 \times 10^6$/g or $1.1 \times 10^6$/g, respectively (P<0.001, MVAΔE3L-hFlt3L vs. PBS; FIG. 7B).

The ratios of CD8+ T cells over regulatory T cells (Tregs, defined as CD4+ FoxP3+ cells) and Tconv (CD4+ Foxp3− cells) over Tregs was also assessed. It was observed that in the injected tumors, intratumoral injection of MVAΔE3L-hFlt3L or MVAΔE3L increased the ratios of CD8+/Treg from 2.8 to 18.6 or 12.5 (P<0.01, MVAΔE3L vs. PBS; P<0.001, MVAΔE3L-hFlt3L vs. PBS, P<0.05, MVAΔE3L vs. MVAΔE3L-hFlt3L; FIG. 7C). The inventors also found that in the non-injected tumors, intratumoral injection of MVAΔE3L-hFlt3L or MVAΔE3L at the contralateral tumors increased the ratios of CD8+/Treg from 3.4 to 11 or 7.8 (P<0.01, MVAΔE3L vs. PBS; P<0.01, MVAΔE3L-hFlt3L vs. PBS; FIG. 7C).

The inventors observed that in the injected tumors, intratumoral injection of MVAΔE3L-hFlt3L or MVAΔE3L increased the ratios of effector CD4+/Treg from 0.65 to 4.1 or 3.2 (P<0.01, MVAΔE3L vs. PBS; P<0.01, MVAΔE3L-hFlt3L vs. PBS; FIG. 7D). It was also found that in the non-injected tumors, intratumoral injection of MVAΔE3L-hFlt3L or MVAΔE3L at the contralateral tumors increased the ratios of effector CD4+/Treg from 0.7 to 3.3 or 2.9 (P<0.0001, MVAΔE3L vs. PBS; P<0.05, MVAΔE3L-hFlt3L vs. PBS; FIG. 7D).

These results indicate that intratumoral injection of MVAΔE3L-hFlt3L triggered immunological changes in the tumor microenvironment, which manifested as proliferation and activation of cytotoxic CD4+ and CD8+ T cells and increasing the ratios of CD8+/Treg and Tconv/Treg.

Example 5

Figure 8:
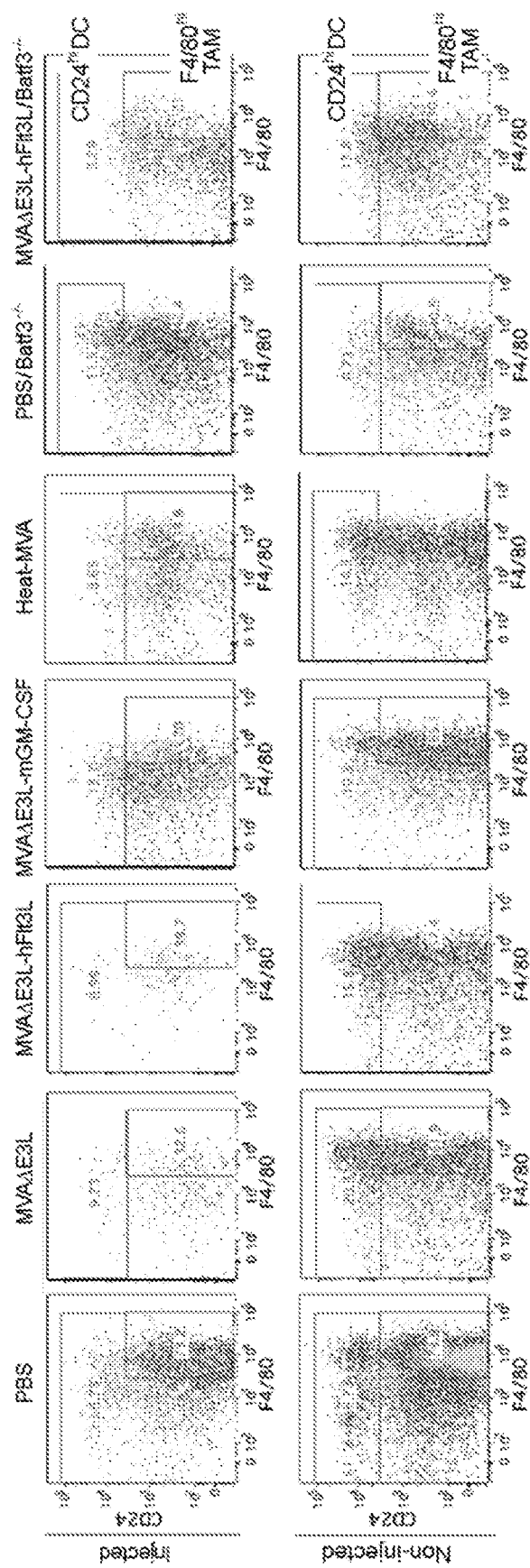
FIG. 8 is a series of graphic representations of flow cytometry plots of F4/80+ TAMs and CD24+ DCs in injected and non-injected tumors. TAMs and DCs are CD45+ MHC-II$^{hi}$Ly6C$^{lo}$. They were further separated by CD24 and F4/80 expression patterns. TAMs are F4/80hiCD24$^{lo}$, where CD24+ DCs express high levels of CD24.
Figure 9:
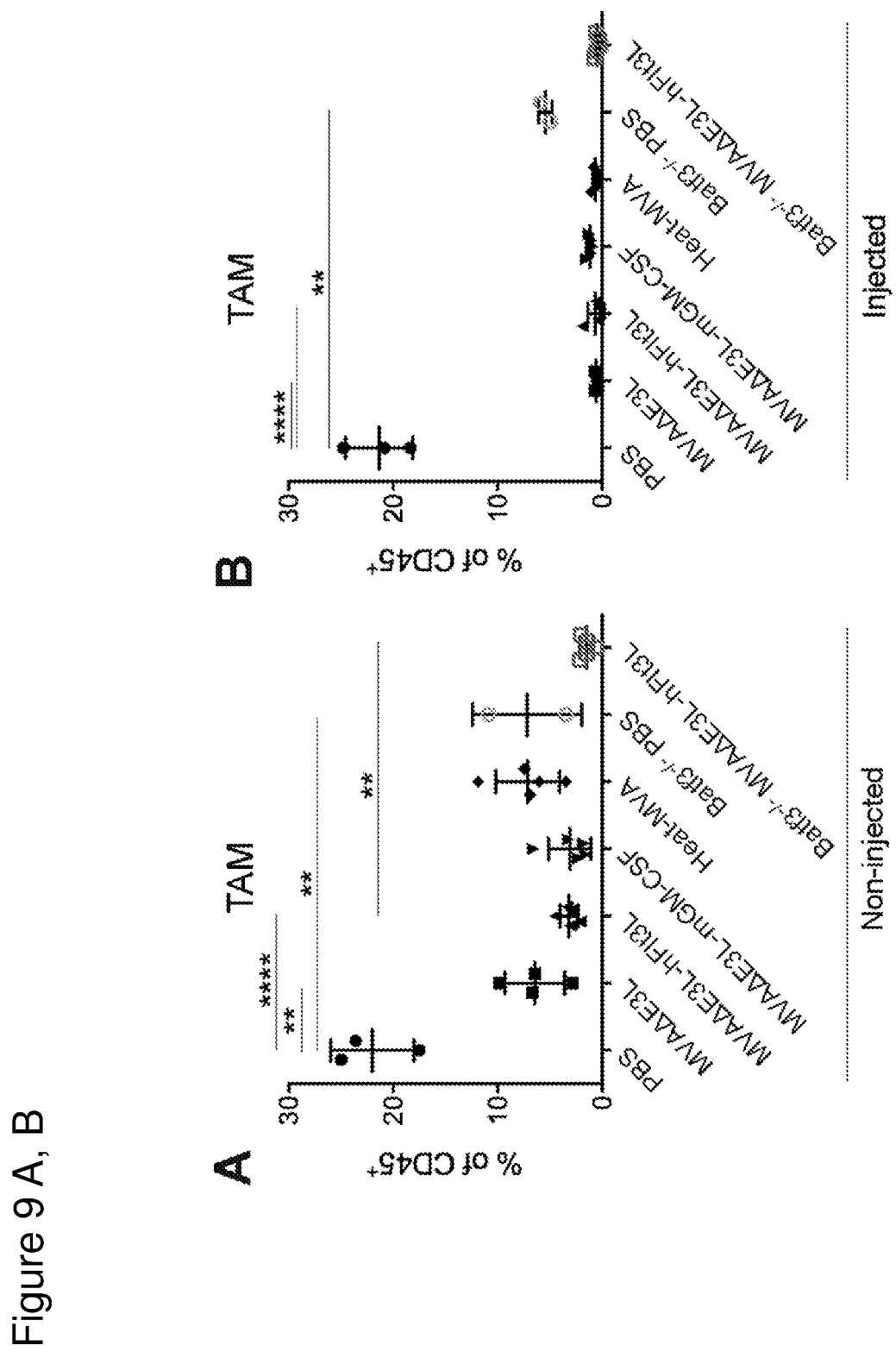
FIG. 9 is a series of graphic representations showing that intratumoral injection of MVAΔE3L-hFlt3L reduces tumor-associated macrophages (TAM) in both injected and non-injected tumors. (A, B) Percentage of TAM cells out of CD45+ cells in both injected (B) and non-injected (A) tumors of WT mice treated with PBS, MVAΔE3L, MVAΔE3L-mGM-CSF, MVAΔE3L-hFlt3L, or Heat-MVA as well as Batf3$^{-/-}$ mice treated with PBS or MVAΔE3L-Flt3L (, p<0.01, **, p<0.0001). Data are means 0 SEM (n=3 for PBS group and n=5 for each virus group in WT mice; n=2 for PBS group and n=5 for each virus group in Batf3$^{-/-}$ mice).

Intratumoral Injection of MVAΔE3L-hFlt3L is Effective in Depleting Tumor-Associated Macrophages in Both Injected and Non-Injected Tumors Tumor-associated macrophages (TAMs) are tumor infiltrating myeloid cells that express the following surface markers CD45+ MHC-II+ F4/80$^{hi}$CD24$^{lo}$ (Broz, et al. *Cancer Cell*, 26(5):638-52, 2014). The inventors analyzed the percentage of TAMs among CD45+ cells in both injected and non-injected tumors. They observed that intratumoral injection of MVAΔE3L-hFlt3L reduced the percentages of TAMs out of CD45+ cells from 21.4% to 0.7% in injected tumors (P<0.0001, MVAΔE3L-hFlt3L vs. PBS; FIGS. 8, 9B) and from 22% to 3.2% in non-injected tumors (P<0.0001, MVAΔE3L-hFlt3L vs. PBS; FIGS. 8, 9A). MVAΔE3L-hFlt3L is more effective than MVAΔE3L in reducing TAMs in non-injected tumors (P<0.05, MVAΔE3L-hFlt3L vs. MVAΔE3L; FIGS. 8, 9A). In the Batf3$^{-/-}$ mice, the percentages of TAMs out of CD45+ cells in PBS-treated mice were 5.4% in injected tumors and 7.2% in the non-injected tumors (P<0.01, injected tumors in WT PBS vs. Batf3$^{-/-}$ PBS; FIGS. 8, 9B; P<0.05, non-injected tumors in WT PBS vs. Batf3$^{-/-}$ PBS; FIGS. 8, 9B). Intratumoral injection of MVAΔE3L-hFlt3L further reduced the percentages of TAMs out of CD45+ cells to 0.5% in the injected tumors and 1.5% in the non-injected tumors (P<0.0001, injected tumors in Batf3$^{-/-}$ MVAΔE3L-hFlt3L vs. Batf3$^{-/-}$ PBS; FIGS. 8, 9B; P<0.05, non-injected tumors in Batf3$^{-/-}$ MVAΔE3L-hFlt3L vs. Batf3$^{-/-}$ PBS; FIGS. 8, 9A). The markedly reduced numbers of TAMs in tumors of Batf3−/− mice suggest the generation of TAMs might be linked to the CD8+ T cell infiltration within the tumors. TAMs have been shown to promote tumor progression and metastasis. Effective depletion of TAMs from both injected and non-injected tumors by intratumoral injection of MVAΔE3L-hFlt3L might contribute to the effectiveness of this therapy.

Example 6

Intratumoral Injection of MVAΔE3L-hFlt3L Results in the Dynamic Changes of Dendritic Cell Populations in Both Injected and Non-Injected Tumors The inventors next analyzed dendritic cell (DC) populations in both injected and non-injected tumors. Tumor infiltrating DCs are characterized as CD45+ Ly6C-MHC-11+ CD24$^{hi}$F4/80$^{lo}$ cells (Broz et al., Cancer Cell, 2014). Among the CD24$^{hi}$ DCs, there are two DC populations, CD11b+ DC and CD103+ DC. The percentage of CD24$^{1''}$ DCs (CD24+) out of CD45+ cells in both injected and non-injected tumors was investigated. It was found that intratumoral injection of MVAΔE3L-hFlt3L in WT mice resulted in the reduction of CD24+ DCs from 3% to 1.3% in non-injected tumors (P=0.001, MVAΔE3L-hFlt3L vs. PBS; FIG. 9A) and 2.4% to 0.2% in injected tumors (P=0.0004, MVAΔE3L-hFlt3L vs. PBS; FIG. 9B). Intratumoral injection of MVAΔE3L-hFlt3L in Batf3$^{-/-}$ mice also resulted in the reduction of CD24$^+$ DCs from 3.4% to 0.8% in non-injected tumors (P=0.05, Batf3$^{-/-}$ MVAΔE3L-hFlt3L vs. Batf3$^{-/-}$ PBS; FIG. 9A) and 2.6% to 0.3% in injected tumors (P<0.0001, Batf3-/- MVAΔE3L-hFlt3L vs. Batf3$^{-/-}$ PBS; FIG. 9B). These findings are consistent with activation of dendritic cells.

Figure 10:
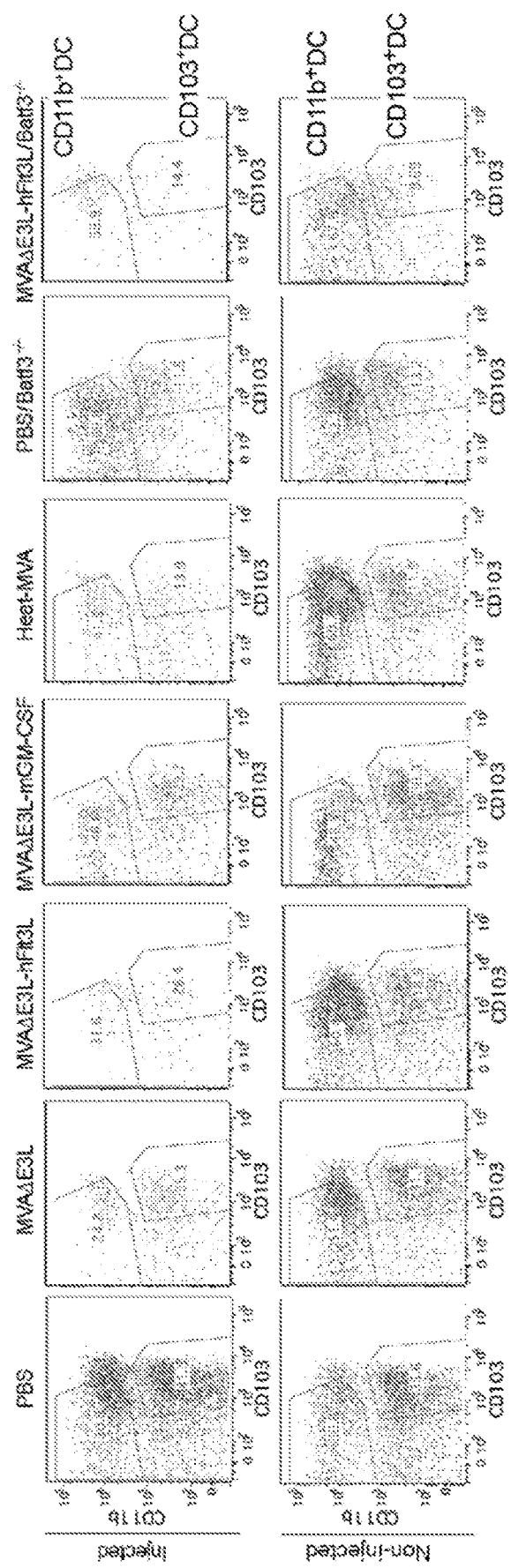
FIG. 10 is a series of graphic representations of flow cytometry plots of CD103+ and CD11b+ DCs in injected and non-injected tumors after virus treatment. Tumor-associated CD24+ DCs can be further separated by their expression of CD11b and CD103. CD11b+ DCs express a high level of CD11b, whereas CD103+ DCs express a high level of CD103.
Figure 11:
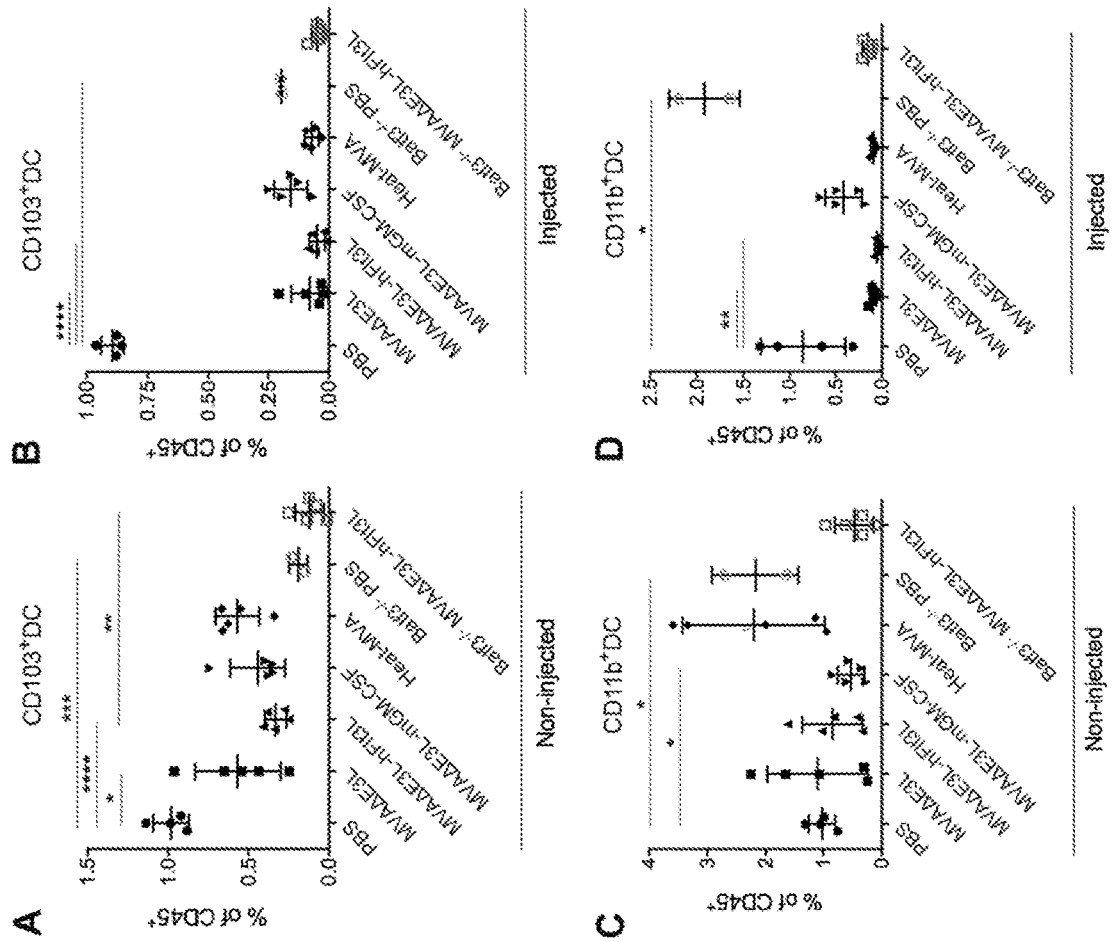
FIG. 11 is a series of graphical representations showing that intratumoral injection of MVAΔE3L-hFlt3L leads to the reduction of CD24+, CD103+ and CD11b+ dendritic cells in the injected tumors and CD24+, CD103+ dendritic cells in the non-injected tumors. (A, B) Percentages of CD24+ DCs out of CD45+ cells in both injected (B) and non-injected (A) tumors of WT mice treated with PBS, MVAΔE3L, MVAΔE3L-mGM-CSF, MVAΔE3L-hFlt3L, or Heat-MVA as well as Batf3$^{-/-}$ mice treated with PBS or MVAΔE3L-Flt3L (, p<0.01, *, p<0.001, ****, p<0.0001). Data are means 0 SEM (n=3 for PBS group and n=5 for each virus group in WT mice; n=2 for PBS group and n=5 for each virus group in Batf3–/– mice). (C, D) Percentages of CD103+ DCs out of CD45+ cells in both injected (D) and non-injected (C) tumors (*, p<0.05, , p<0.01, *, p<0.001, ****, p<0.0001). Data are means 0 SEM (n=3 for PBS group and n=5 for each virus group in WT mice; n=2 for PBS group and n=5 for each virus group in Batf3$^{-/-}$ mice). (E, F) Percentages of CD11b+ DCs out of CD45+ cells in both injected (F) and non-injected (E) tumors (*, p<0.05, **, p<0.01). Data are means±SEM (n=3 for PBS group and n=5 for each virus group in WT mice; n=2 for PBS group and n=5 for each virus group in Batf3$^{-/-}$ mice).

CD103$^+$ DCs is a subset of peripheral DCs that are specialized in cross-presenting antigens. Batf3 is a transcription factor that is important for the differentiation of CD103$^+$ DCs. CD103$^+$ DCs play important roles in host anti-tumor immunity. The inventors of the present disclosure have previously shown that Batf3-dependent CD103$^+$ DCs are required for inactivated MVA-mediated antitumor effects (WO2016/168862). Here, the inventors investigated the percentages of CD103$^+$ DCs out of CD45$^+$ cells in both injected and non-injected tumors. It was found that intratumoral injection of MVAΔE3L-hFlt3L in WT mice resulted in the reduction of CD103$^+$ DCs from 1.0% to 0.3% in non-injected tumors (P<0.0001, MVAΔE3L-hFlt3L vs. PBS; FIGS. 10, 11A) and 0.9% to 0.05% in injected tumors (P<0.0001, MVAΔE3L-hFlt3L vs. PBS; FIGS. 10, 11B). The CD103$^+$ DCs were much reduced in Batf3$^{-/-}$ mice compared with WT mice as expected (P<0.0001, WT PBS vs. Batf3$^{-/-}$ PBS; FIG. 10, 11A, 11B). These results indicate that CD103$^+$ DCs undergo dynamic changes after intratumoral injection with viruses.

The percentages of CD11b$^+$ DCs out of CD45$^+$ cells in both injected and non-injected tumors were also investigated. It was found that intratumoral injection of MVAΔE3L-hFlt3L in WT mice resulted in the reduction of CD103$^+$ DCs from 0.9% to 0.06% in injected tumors (P<0.01, MVAΔE3L-hFlt3L vs. PBS; FIGS. 10, 11D) and from 1.0% to 0.8% in non-injected tumors (P=0.54, MVAΔE3L-hFlt3L vs. PBS; FIG. 10, 11C). The CD11b$^+$ DCs were not affected in Batf3$^{-/-}$ mice compared with WT mice as expected (FIGS. 10, 11C, and 11D). These results indicate that CD11b$^+$ DCs can also undergo dynamic changes after intratumoral injection with viruses at the injected tumors. CD11b$^+$ DCs at non-injected tumors are less mobile than CD103$^+$ DCs.

Example 7

Figure 12:
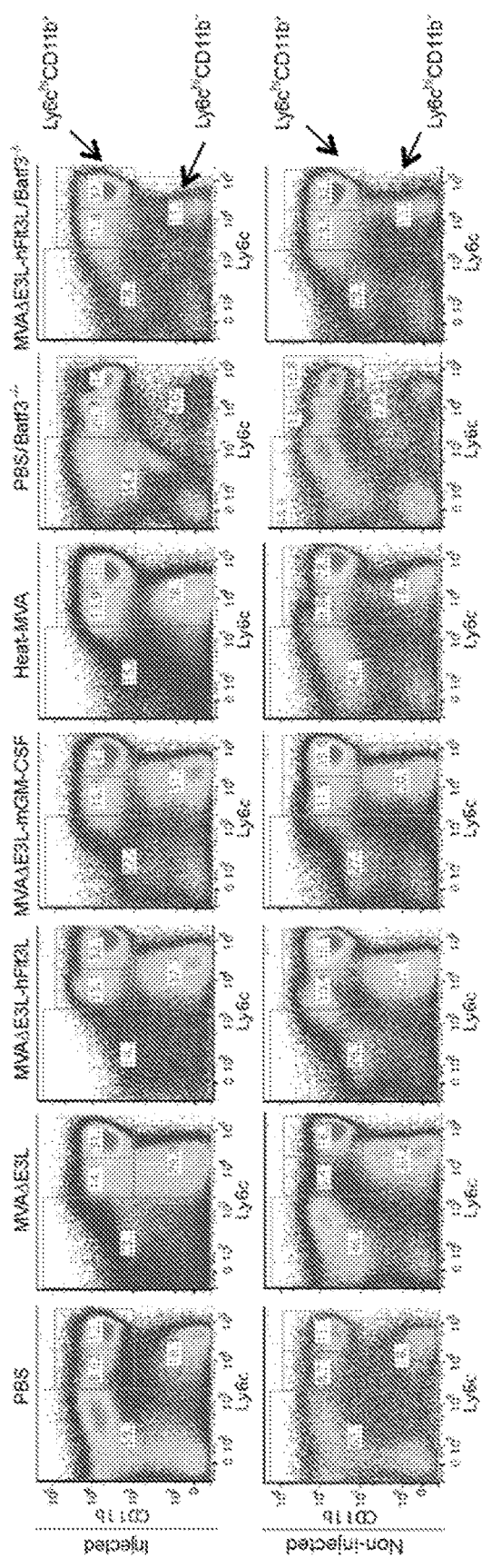
FIG. 12 is a series of graphic representations of flow cytometry plots of myeloid cell populations in injected and non-injected tumors after virus treatment. CD45+ tumor infiltrating myeloid cells were further separated by their expression of CD 11b and Ly6C. Ly6C+ cells can be further divided into several populations, including Ly6C$^{hi}$CD11b+ inflammatory monocytes, Ly6C$^{hi}$CD11b$^-$ cells, as well as Ly6C$^{int}$CD11b+ cells (likely neutrophils).

Intratumoral Injection of MVAΔE3L-hFlt3L Results in the Influx of Ly6C$^{hi}$CD11b$^+$ and Ly6C$^+$ CD11b$^-$ Cells in Both Injected and Non-Injected Tumors Ly6C$^{hi}$CD11b$^+$ cells are C—C chemokine receptor (CCR2) expressing inflammatory monocytes that are recruited to site of injury or infection due to C—C chemokine ligand 2 (CCL2). These cells give rise to TNF and iNOS-producing dendritic cells (TipDCs) and other inflammatory cells subsets, leading to tissue injury or microbial killing. The inventors investigated the percentages of Ly6C$^{hi}$CD11b$^+$ monocytes out of CD45$^+$ cells in both injected and non-injected tumors. It was found that intratumoral injection of MVAΔE3L-hFlt3L in WT mice resulted in the increase of Ly6C$^{hi}$CD11b$^+$ monocytes from 11.7% to 37% in injected tumors (P=0.0011, MVAΔE3L-hFlt3L vs. PBS; FIGS. 12, 13B) and from 13.5% to 26% in non-injected tumors (P=0.0102, MVAΔE3L-hFlt3L vs. PBS; FIG. 12, 13A). The Ly6C$^{hi}$CD11b$^+$ monocytes were not affected in Batf3$^{-/-}$ mice compared with WT mice as expected (FIGS. 12, 13A, and 13B). Interestingly, intratumoral injection of MVAΔE3L-mGM-CSF resulted in the increase of Ly6C$^{hi}$CD11b$^+$ monocytes from 11.7% to 25.7% in injected tumors (P=0.0011, MVAΔE3L-hFlt3L vs. PBS; FIGS. 12, 13B) and from 13.5% to 35.6% in non-injected tumors (P<0.0001, MVAΔE3L-mGM-CSF vs. PBS; FIGS. 12, 13A). These results indicate that Ly6C$^{hi}$CD11b$^+$ monocytes are recruited to both injected and non-injected tumors after virus treatment.

The inventors also observed a dramatic increase of Ly6C$^{hi}$CD11b$^-$ cells in both injected tumors and non-injected tumors in virus-treated mice. Intratumoral injection of MVAΔE3L-hFlt3L in WT mice resulted in the increase of Ly6C$^{hi}$CD11b$^-$ cells from 16.5% to 32.7% in injected tumors (P=0.0047, MVAΔE3L-hFlt3L vs. PBS; FIGS. 12, 13D) and from 15.3% to 32.7% in non-injected tumors (P=0.0045, MVAΔE3L-hFlt3L vs. PBS; FIGS. 12, 13C). The Ly6C$^{hi}$CD11b$^-$ cells were reduced in Batf3$^{-/-}$ mice compared with WT mice in the PBS-treated mice (16.5% in WT mice vs. 4.9% in Batf3$^{-/-}$ mice, FIGS. 12, 13C, and 13D). Intratumoral injection of MVAΔE3L-hFlt3L resulted in the increase of Ly6C$^{hi}$CD11b$^-$ cells from 4.9% to 1.3.3% in injected tumors (P=0.0117, Batf3$^{-/-}$ MVAΔE3L-hFlt3L vs. Batf3$^{-/-}$ PBS; FIGS. 12, 13D) and from 6.3% to 13.9% in non-injected tumors (P<0.05, Batf3$^{-/-}$ MVAΔE3L-hFlt3L vs. Batf3$^{-/-}$ PBS; FIGS. 12, 13C). These results indicate that Ly6C$^{hi}$CD11b$^-$ cells are recruited to both injected and non-injected tumors after immune stimulating virus such as MVAΔE3L, MVAΔE3L-mGM-CSF, MVAΔE3L-hFlt3L or Heat-MVA treatment. It is possible that anti-tumor CD8$^+$ T cells and antiviral CD8$^+$ T cells might be important for the recruitment of Ly6C$^{hi}$CD11b$^-$ cells to the tumor sites.

Example 8

Intratumoral Injection of MVAΔE3L-hFlt3L is More Effective than MVAΔE3L in a Bilateral MC38 Tumor Implantation Model To compare the antitumor efficacy of MVAΔE3L-hFlt3L vs. MVAΔE3L in a different solid tumor model, the inventors intradermally implanted 5×10$^5$ MC38 colon cancer cells into the right flank and 1×10$^5$ cells into the left flank of C57B/6 mice. Tumors were allowed to grow for 7-8 days, after which MVAΔE3L-hFlt3L or MVAΔE3L (2×10$^7$ pfu) or PBS control were injected into the larger tumors twice a week. Whereas all of the PBS control mice died at 7-14 days (with a median survival of 10 days) post PBS-mock treatment due to tumor growth (FIGS. 14A and 14B), intratumoral injection with MVAΔE3L extended the median survival from 10 days in the PBS group to 21 days in the MVAΔE3L group (****, P<0.0001 for MVAΔE3L (n=10) vs. PBS (n=10)).

Intratumoral injection of MVAΔE3L-hFlt3L further extended the median survival to 23 days (**, P<0.003 for MVAΔE3L-hFlt3L (n=10) vs. MVAΔE3L (n=10)). These results indicate that MVAΔE3L-hFlt3L is more efficacious than MVAΔE3L in a bilateral MC38 tumor implantation model.

Example 9

Figure 15A:
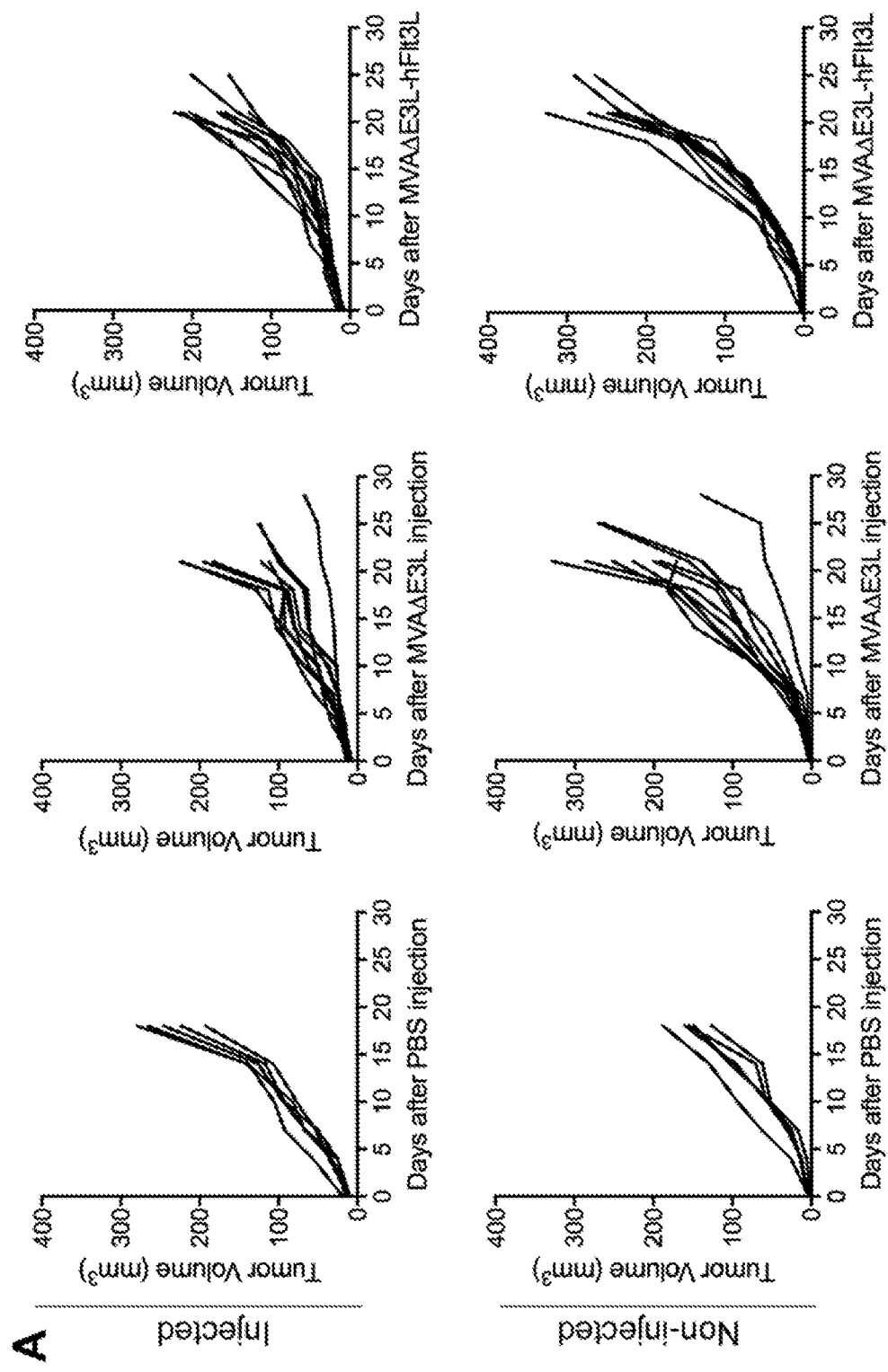
FIG. 15 shows a series of graphical representations of intratumoral injection of MVAΔE3L or MVAΔE3L-hFlt3L in a 4T1 murine triple negative breast carcinoma (TNBC) bilateral implantation model. 4T1 cells ($2.5 \times 10^5$) were implanted intradermally into the shaved skin on the right flank and ($5 \times 10^4$) cells were implanted to the left flank of BALB/c mice. At 5 days post implantation, the right side tumors (about 3 mm in diameter) were injected twice weekly with either PBS, MVAΔE3L ($2 \times 10^7$ pfu), or MVAΔE3L-hFlt3L ($2 \times 10^7$ pfu). (A) are a series of graphs of respective tumor volumes (injected and non-injected) over days after injection with PBS, MVAΔE3L, or MVAΔE3L-hFlt3L viruses in a bilateral 4T1 tumor implantation model. (B, C) are graphs of the respective tumor volumes (injected and non-injected) at day 18 post the first injections. (n=5 for PBS and n=10 for MVAΔE3L or MVAΔE3L-hFlt3L; **, P<0.0001). (D) Kaplan-Meier survival curve of mice treated with PBS, MVAΔE3L, or MVAΔE3L-hFlt3L. Survival data were analyzed by log-rank (Mantel-Cox) test. (n=5 for PBS and n=10 for MVAΔE3L or MVAΔE3L-hFlt3L; *, P<0.001).

Intratumoral Injections of MVAΔE3L or MVAΔE3L-hFlt3L are Also Effective in a Murine Triple-Negative Breast Cancer 4T1 Bilateral Implantation Model In addition to B16-F10 murine melanoma and MC38 colon adenocarcinoma models, the inventors investigated whether intratumoral injection of MVAΔE3L or MVAΔE3L-hFlt3L has efficacy in the treatment of triple-negative breast cancer (TNBC) 4T1 bilateral tumor implantation model. Briefly, 4T1 murine triple negative breast cancer (TNBC) cells were implanted intradermally to the left and right flanks of BALB/c mice ($2.5 \times 10^5$ to the right flank and $5 \times 10^4$ to the left flank). 5 days post tumor implantation, the larger tumors on the right flank were injected with either MVAΔE3L or MVAΔE3L-hFlt3L ($2 \times 10^7$ pfu) twice weekly. Mice were monitored daily and tumor sizes were measured twice weekly. The survival of mice was monitored. It was found that intratumoral injection of MVAΔE3L or MVAΔE3L-hFlt3L led to dramatic decrease of tumor volumes of the injected tumors compared with PBS-treated tumors (FIG. 15A). The tumor volumes of the injected and non-injected tumors at 18-day post treatment were shown (FIG. 15, B, C; P<0.0001, MVAΔE3L or MVAΔE3L-hFlt3L vs. PBS). More importantly, the mean survival of mice was extended from 18 days in PBS-treated mice to 21 days in MVAΔE3L or MVAΔE3L-hFlt3L-treated mice (FIG. 15D; P=0.0001, MVAΔE3L or MVAΔE3L-hFlt3L vs. PBS). These results indicate that intratumoral injection of MVAΔE3L or MVAΔE3L-hFlt3L in a bilateral 4T1 breast cancer model is effective in delaying tumor growth and extend survival of the treated mice. Based on the results contained herein, it is anticipated that the combination of MVAΔE3L or MVAΔE3L-hFlt3L with immune checkpoint blockade such as anti-CTLA-4 or anti-PD-1/PD-L1 antibodies would also be more effective than virotherapy alone in this bilateral 4T1 implantation model.

Example 10

Intratumoral Injections of MVAΔE3L-hFlt3L is Effective in a Murine Prostate Cancer TRAMP-C2 Unilateral Tumor Implantation Model, which Requires STING The inventors investigated whether intratumoral injection of MVAΔE3L-hFlt3L has efficacy in the treatment of murine prostate adenocarcinoma TRAMP-C2 unilateral tumor implantation model. Briefly, TRAMP-C2 cells were implanted intradermally to the shaved right flank of STING$^{Gt/Gt}$ mice and age-matched WT C57B/6 controls ($1 \times 10^6$ cells in 50 μl of PBS per mouse). 17 days post tumor implantation, the tumors (around 3-4 mm in diameter) on the right flank were injected with either PBS or MVAΔE3L-hFlt3L ($2 \times 10^7$ pfu) twice weekly. Mice were monitored daily and tumor sizes were measured twice weekly. The survival of mice was monitored. It was found that intratumoral injection of MVAΔE3L-hFlt3L led to dramatic decrease of tumor volumes of the injected tumors in the WT mice compared with PBS-treated tumors, but it was less effective in STING-deficient mice (FIG. 16, A-D). The initial tumor volumes and 24-day post injection tumor volumes were shown in FIGS. 16 E and F, respectively. It was observed that the mean volumes of MVAΔE3L-hFlt3L-injected tumors were 118 mm$^3$ in WT mice and 282 mm$^3$ in STING$^{Gt/Gt}$ mice, whereas the mean volumes of PBS-injected tumors were 338 mm$^3$ in WT mice and 433 mm$^3$ in STING$^{Gt/Gt}$ mice (FIG. 16F; P<0.0001, MVAΔE3L-hFlt3L vs. PBS in WT mice; P<0.0001, MVAΔE3L-hFlt3L vs. PBS in STING$^{Gt/Gt}$ mice). These results indicate that MVAΔE3L-hFlt3L has antitumor effects in both WT and STING$^{Gt/Gt}$ mice, but it was more effective in WT mice than in STING$^{Gt/Gt}$ mice (FIG. 16F; P<0.0001, STING$^{Gt/Gt}$ vs. WT mice treated with MVAΔE3L-hFlt3L). This experiment is still ongoing at the time of the PCT filing. The survival data will be available at the end of the experiment. These results indicate that STING-dependent cytosolic DNA-sensing pathway plays an important role in mediating the antitumoral effects of MVAΔE3L-hFlt3L in this unilateral murine prostate adenocarcinoma model. The inventors have previously reported that STING-dependent cytosolic DNA sensing pathway is important for Heat-inactivated MVA-mediated antitumor effects in a B16-F10 melanoma model (see, International Patent Application WO/2016/144564). Similar to Heat-MVA, MVAΔE3L induces type I IFN in BMDCs largely through the cytosolic DNA-sensing pathway (Ref MVAΔE3L provisional patent application). Here the inventors confirmed that intratumoral injection of MVAΔE3L-hFlt3L induces antitumor effects mediated by STING in a prostate cancer model.

Example 11

Figure 17A:
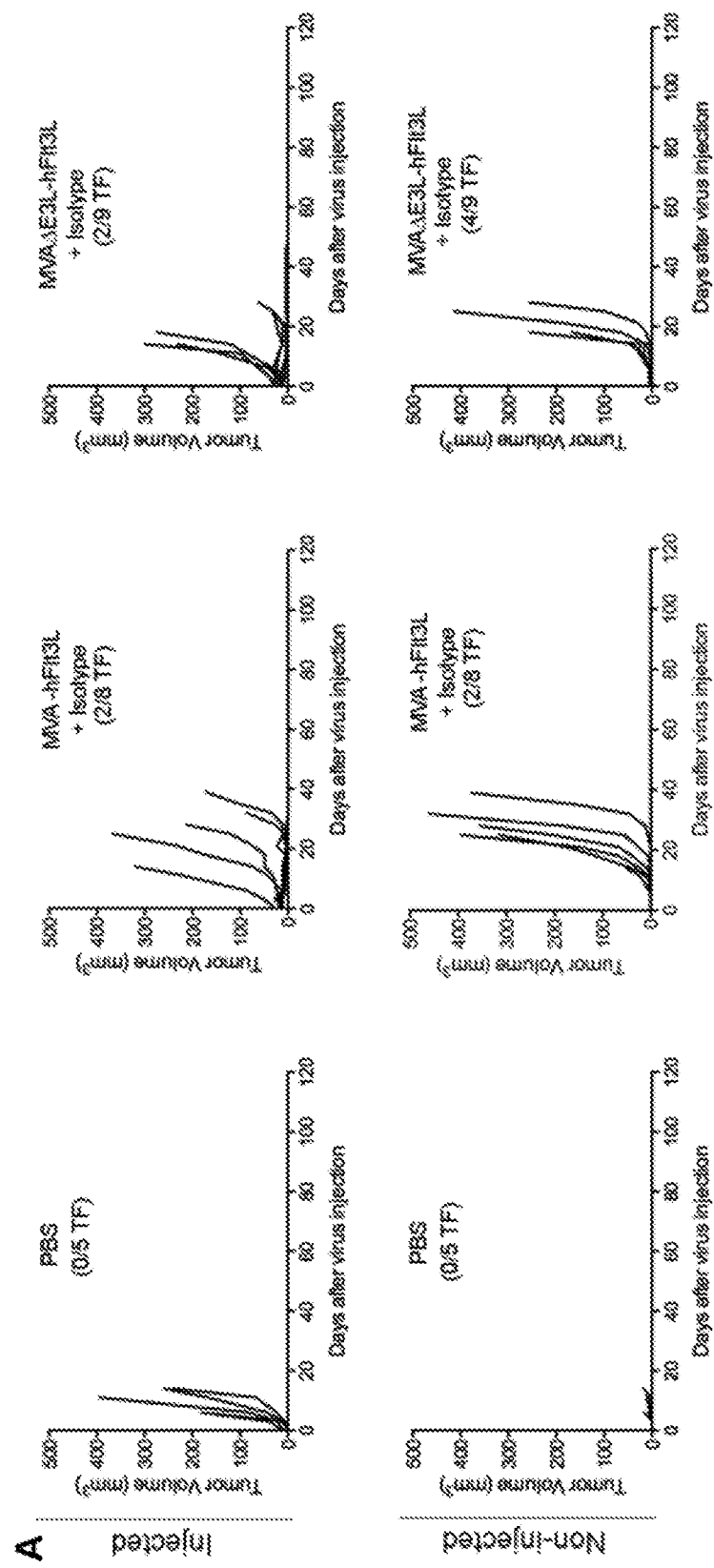
Figure 17B:
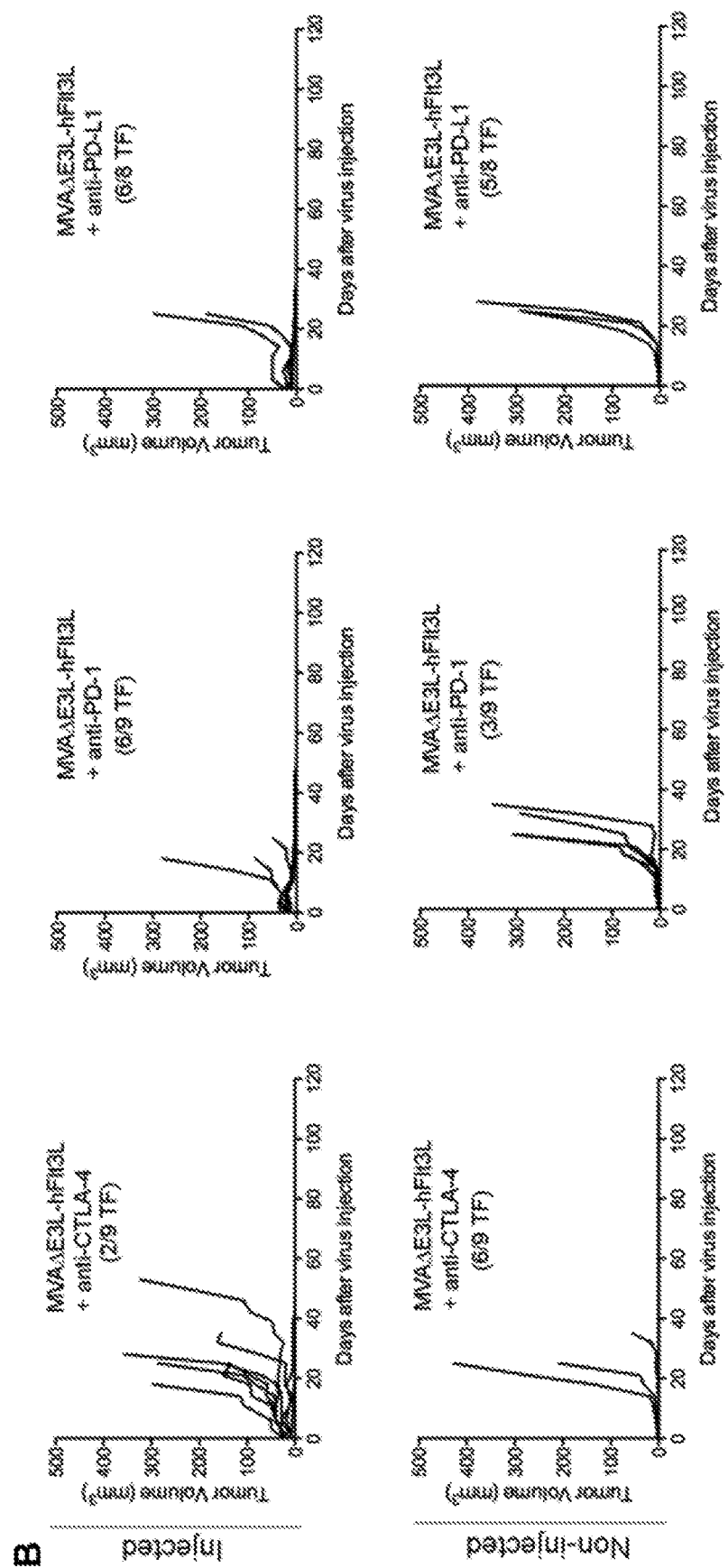
Figure 17C:
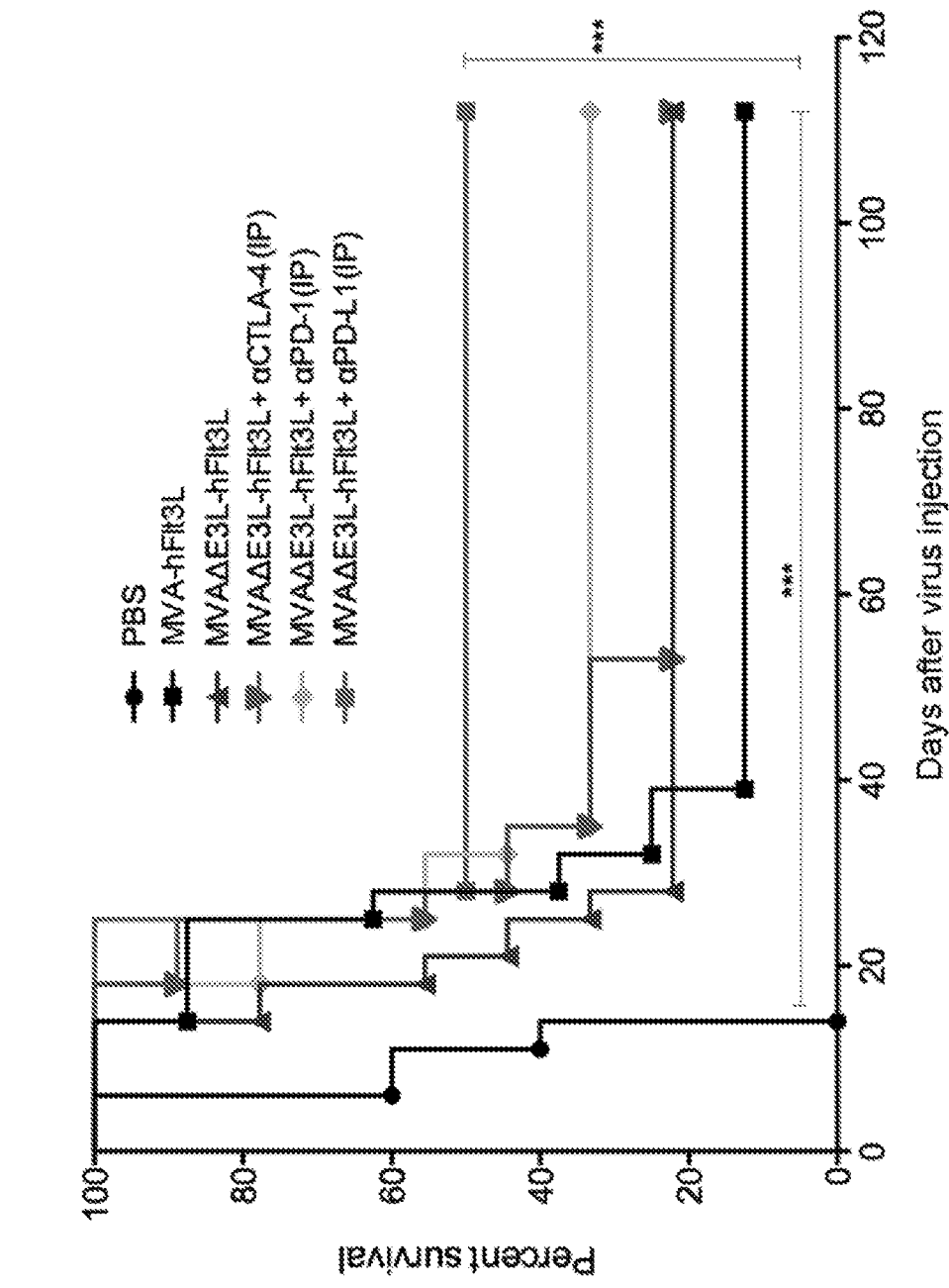

Intratumoral Injection of MVA-hFlt3L is Also Effective in a Bilateral B16-F10 Melanoma Implantation Model To test whether intratumoral injection of MVA-hFlt3L exerts an antitumor effect in a bilateral B16-F10 implantation model, MVA-hFlt3L or MVAΔE3L-hFlt3L or PBS was injected into the larger tumors twice a week and tumor sizes and survival were monitored. The inventors found that intratumoral injection of MVA-hFlt3L eradicated or delayed tumor growth in both injected and non-injected tumors and extended the median survival from 11 days in the PBS group to 28 days in the MVA-hFlt3L group (***, P=0.0008 for MVA-hFlt3L (n=8) vs. PBS (n=5)) (FIGS. 17A and 17C). This result indicates that intratumoral injection of MVA-hFlt3L is also effective against tumors in a bilateral tumor implantation model.

Example 12

The Combination of Intratumoral Injection of MVAΔE3L-hFlt3L and Systemic Delivery of Immune Checkpoint has Synergistic Antitumor Effects in a Bilateral B16-F10 Melanoma Implantation Model The inventors have previously shown that the combination of intratumoral injection of inactivated MVA and systemic delivery of immune checkpoint blockade results in enhanced efficacy compared to either agent alone in bilateral B16-F10 and MC38 tumor implantation models. In the present disclosure, the inventors tested whether the Combination of intratumoral injection of MVAΔE3L-hFlt3L and systemic delivery of immune checkpoint blockade would also result in better tumor killing and improved survival than virotherapy alone in a bilateral B16-F10 melanoma implantation model. 8 days after tumor implantation, MVAΔE3L-hFlt3L virus was injected into the larger tumors on the right flank twice weekly. Four groups of mice were treated with MVAΔE3L-hFlt3L, with each group receiving intraperitoneal delivery of either the isotype control, or anti-CTLA-4, or anti-PD-1, or anti-PD-L1 antibodies (FIG. 17A, B). Whereas the PBS-treated mice died quickly with increasing tumor growth at 6-14 days post PBS-mock treatment, the mice treated with MVAΔE3L-hFlt3L+isotype control eliminated or delayed the growth of both injected and non-injected tumors (FIG. 17A, B). As a result, treatment with MVAΔE3L-hFlt3L+isotype (n=9) significantly extended their survival compared with the PBS group (n=5) (FIG. 17C, **, P=0.0011). The combination of intratumoral injection of MVAΔE3L-hFlt3L and systemic delivery of anti-CTLA-4, anti-PD-1 and anti-PD-L1 antibodies were more effective in eradicating or delaying the growth of both injected and non-injected tumors than intratumoral injection of MVAΔE3L-hFlt3L alone. 2/9 of mice treated with MVAΔE3L-hFlt3L+anti-CTLA-4, 3/9 of mice treated MVAΔE3L-hFlt3L+anti-PD-1, and 4/8 of mice treated with MVAΔE3L-hFlt3L+anti-PD-L1 were tumor free at 112 days post-treatment, whereas 2/9 of mice treated with MVAΔE3L-hFlt3L+isotype were tumor free (FIG. 17, A-C). Intraperitoneal delivery of anti-CTLA-4, anti-PD-1, or anti-PD-L1 alone had minimal therapeutic benefits in the B16-F10 melanoma model. These results indicate that intratumoral delivery of MVAΔE3L-hFlt3L overcomes treatment resistance to immune checkpoint blockade in a metastatic B16 melanoma model, leading to improved anti-tumor effects.

Example 13

Figure 17D:
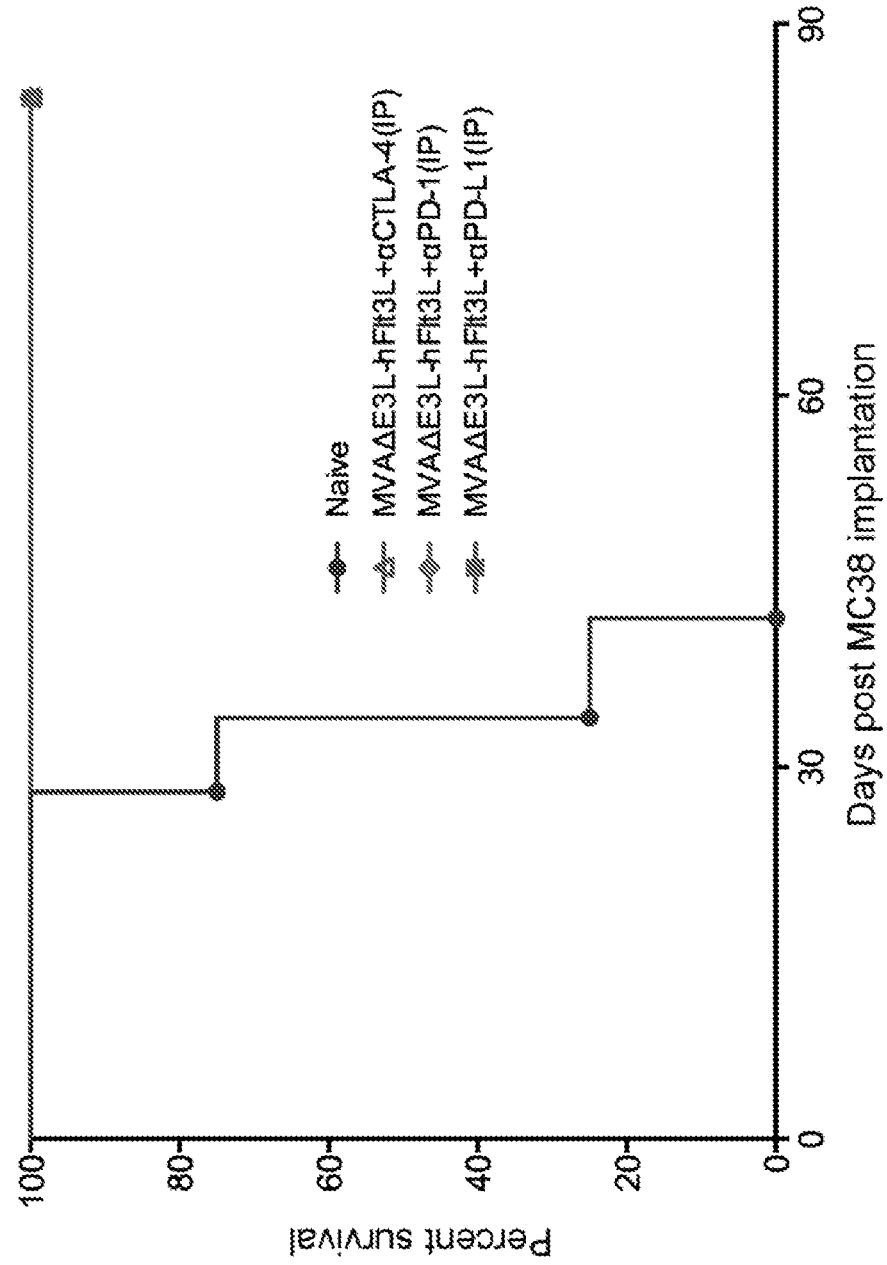

The Surviving Mice Treated with Intratumoral Injection of MVAΔE3L-hFlt3L in Combination with Systemic Delivery of Immune Checkpoint Developed Immunity Against Challenge of a Different Tumor Type To assess whether the surviving mice post intratumoral injection of MVAΔE3L-hFlt3L have developed immunity against a different tumor type, we rechallenged them with a lethal dose of MC38 ($1\times10^5$) implanted intradermally. Naïve mice (n=4) that have never exposed to the said tumors or viruses were used as a control. Whereas all of the naïve mice developed tumors and died at 34-42 days post tumor implantation with a median survival of 34 days, all of the MVAΔE3L-hFlt3L+ immune checkpoint blockade-treated surviving mice rejected MC38 tumor challenge in this experiment (FIG. 17D). These include 2 surviving mice from the MVAΔE3L-hFlt3L+anti-CTLA-4 group, 3 from the MVAΔE3L-hFlt3L+anti-PD-1 group, and 4 from MVAΔE3L-hFlt3L+anti-PD-L1 group. These results suggest that intratumoral injection with MVAΔE3L-hFlt3L in the presence of immune checkpoint blockade allows efficient recognition of common antigens between B16-F10 melanoma and MC38 colon cancers and the development of anti-tumor immunity against different tumors.

Example 14

Intratumoral Injection with MVAΔE3L-hFlt3L Leads to the Generation of Antitumor CD8$^+$ T Cell Immunity, which is Enhanced in the Presence of Anti-CTLA-4 Antibody The inventors examined whether the surviving mice developed antitumor memory T cell immunity against B16-F10 and MC38 colon cancers after treatment with intratumoral injection of MVAΔE3L-hFlt3L alone or in the presence of intraperitoneal delivery of anti-CTLA-4 antibody by using Enzyme-linked ImmunoSpot (ELISpot). Briefly, CD8$^+$ T cells were isolated from splenocytes and $1\times10^5$ cells were cultured overnight at 37° C. in anti-IFN-1-coated BD ELISPOT plate microwells. CD8$^+$ T Cells were stimulated with either B16-F10 or MC38 cells irradiated with an γ-irradiator and cytokine secretion was detected with an anti-IFN-γ antibody. Whereas CD8$^+$ T cells from nave mice did not show any reactivity to either B16-F10 or MC38 cells, CD8$^+$ T cells from MVAΔE3L-hFlt3L-treated mice showed reactivity to both B16-F10 and MC38 cells (FIGS. 18, A and B). In a separate experiment in which mice implanted with B16-F10 and subsequently treated with MVAΔE3L-hFlt3L intratumorally but have never been exposed to MC38 cells, similar reactivity to MC38 cells were also observed (data not shown). These results indicate that intratumoral injection of MVAΔE3L-hFlt3L for the treatment of B16-F10 led to the development of antitumor immunity against not only B16-F10 melanoma but also an irrelevant tumor type, in this case, MC38 colon adenocarcinoma. This supports the in vivo findings that surviving mice treated with MVAΔE3L-hFlt3L for B16-F10 also successfully rejected challenge of a lethal dose of MC38 (Example 3, FIG. 3D). The cross-protection was also observed when MVAΔE3L or Heat-inactivated MVA or Heat-inactivated vaccinia was delivered intratumorally (data not shown). The efficacy of cross-protection was weaker when a replication oncolytic virus such as E31-6, 83N-TK$^-$-hFlt3L was used (data not shown). It is possible that the immunogenic MVAΔE3L-hFlt3L or Heat-inactivated vaccinia infection results in the efficient cross-presentation of tumor antigens that are present in both B16-F10 and MC38 cancer cells which leads to the development of cross-protection of heterologous tumors.

It was observed that mice treated with the combination of intratumoral injection of MVAΔE3L-hFlt3L and intraperitoneal delivery of anti-CTLA-4 antibody developed a much stronger anti-B16-F10 and anti-MC38 CD8$^+$ T cell responses than those treated with virus alone (FIGS. 18, A and B, , P<0.01, **, P<0.0001, for anti-B16-F10 or anti-MC38 CD8$^+$ T cell responses induced by MVAΔE3L-hFlt3L alone vs. MVAΔE3L-hFlt3L plus anti-CTLA-4). These results indicate that the combination of virotherapy with anti-CTLA-4 antibody not only enhances effector T cell responses but also memory T cell responses.

Example 15

Intratumoral Injection with Heat-Inactivated MVA Induces Type I IFN and Inflammatory Cytokines and Chemokines in Both Injected and Non-Injected Tumors in a Bilateral 816-F10 Tumor Implantation Model The inventors have previously shown that either Heat-inactivated MVA (Heat-MVA) or MVAΔE3L infection of tumor cells or dendritic cells in vitro leads to the induction of type I IFN and proinflammatory cytokine and chemokine production (See, International Patent Applications WO/2016/144564 and WO2016/168862). To test whether intratumoral injection of Heat-MVA can induce type I IFN and proinflammatory cytokines and chemokines in vivo, the inventors performed the following experiment. Briefly, $2.5\times10^5$ B16-F10 melanoma cells were intradermally implanted to the left flank and $5\times10^5$ B16-F10 melanoma cells to the right flank of 6-8 weeks old C57B/6 mice. 7 days post-implantation, MVA ($2\times10^7$ pfu) or Heat-MVA, or PBS was injected into the larger tumors on the right flank. The injection was repeated three days later. Both the injected and non-injected tumors were harvested on day 7 after first injection, and cell suspensions were generated. RNAs were extracted from the cells and quantitative real-time PCR analyses were performed. The results showed that intratumoral injection of Heat-MVA induced much higher levels of induction of genes including Ifnb, Il6, Ccl4, Ccl5, Cxcl9, and Cxcl10 than MVA in both injected tumors and noninjected tumors (FIG. 19). This is probably due to the higher potency of Heat-MVA than MVA to activate the cGAS/STING-mediated cytosolic DNA-sensing mechanism in both immune and tumor cells in the injected tumors. The observation that intratumoral injection of Heat-MVA was able to induce a broad range of cytokine and chemokine production in the non-injected tumors is interesting. This can be explained by the fact that both tumor-specific $CD8^+$ and $CD4^+$ T cells are recruited and activated to the injected and non-injected tumors, which results in the killing of tumor cells. The release of tumor DNA can be sensed by the cGAS/STING cytosolic DNA-sensing pathway in the immune cells including dendritic cells, macrophages, and monocytes, which leads to the induction of Ifnb, Il6, Ccl4, Ccl5, Cxcl9, and Cxcl10 gene expression.

Because E3 is an immune evasion virulence factor, MVAΔE3L induces higher levels of type I IFN and proinflammatory cytokines and chemokines than MVA in both immune cells and tumor cells, through the activation of both the cGAS/STING-dependent cytosolic DNA-sensing pathway and MDA5/MAVS-dependent cytosolic dsRNA-sensing pathway. In light of the results herein, we anticipate that intratumoral injection of MVAΔE3L or MVAΔE3L-hFlt3L would induce higher levels of type I IFN and proinflammatory cytokines and chemokines than MVA in both injected and non-injected tumors in vivo. In the absence of STING or Batf3, the anti-tumor T cell responses induced by intratumoral injection of Heat-MVA are significantly weakened (WO/2016/144564, incorporated by reference in its entirety). In addition, intratumoral injection of MVAΔE3L-hFlt3L induced influx of $Ly6C^{hi}CD11b^-$ cells to the both injected and non-injected tumors in WT mice, but the influx of this cell type was significantly reduced in Batf3-/- mice (Example 7, FIGS. 13 C and D). We also expect that MVAΔE3L-hFlt3L induced Ifnb, Il6, Ccl4, Ccl5, Cxcl9, and Cxcl10 gene expression in both injected and non-injected tumors would be reduced in STING- or Batf3-deficient mice.

Example 16

Intratumoral Injection with Heat-Inactivated MVA Induces Anti-Melanoma $CD8^+$ T Cell Responses in the Tumor Draining Lymph Nodes (TDLNs)

It has been shown that intratumoral delivery of Heat-MVA leads to the induction of activated $CD8^+$ T cells in the TDLNs, it is unclear whether they are anti-tumor T cells or antiviral T cells (WO/2016/144564 incorporated by reference in its entirety). To test whether intratumoral injection of Heat-MVA leads to the induction of activated tumor-specific $CD8^+$ T cells, the inventors used a TRP-2 tetramer assay to detect CD8+ T cells that react to melanocyte antigen TRP-2 immunogenic peptide. Briefly, WT C57B/6 and $Batf3^{-/-}$ mice were intradermally implanted with B16-F10. When the tumors were 4 mm in diameter, they were treated with intradermal injections of Heat-MVA twice 3 days apart. 7 days post the initial injection, TDLNs were incubated and cell suspensions were prepared and incubated for 30 mins at room temperature with anti-FcγR II (2.4G2) antibody and PE-H-2 Kb TRP2 (SVYDFFVWL) tetramer (MBL), followed by staining with anti-CD3 and anti-CD8 antibodies. Cells were analyzed by FACS. It was observed that intratumoral injection of Heat-MVA led to the increase of the percentages of TRP-2 tetramer positive $CD8^+$ T cells in the TDLNs compared with PBS control (FIGS. 20, A and B, *, P<0.05, 9% in Heat-MVA vs. 1.6% in PBS-treated mice). This induction was diminished in Batf3-deficient mice (FIGS. 20, A and B, *, P<0.05, 9% in Heat-MVA-treated WT mice vs. 1.1% in Heat-MVA-treated $Batf3^{-/-}$ mice). These results indicate that intratumoral injection with Heat-MVA results in anti-tumor-specific $CD8^+$ T cell responses, which requires Batf3-dependent DCs. In light of the experimental evidence herein, the inventor a anticipate that similar results would be obtained with MVAΔE3L-hFlt3L virus.

Example 17

Figure 21A:
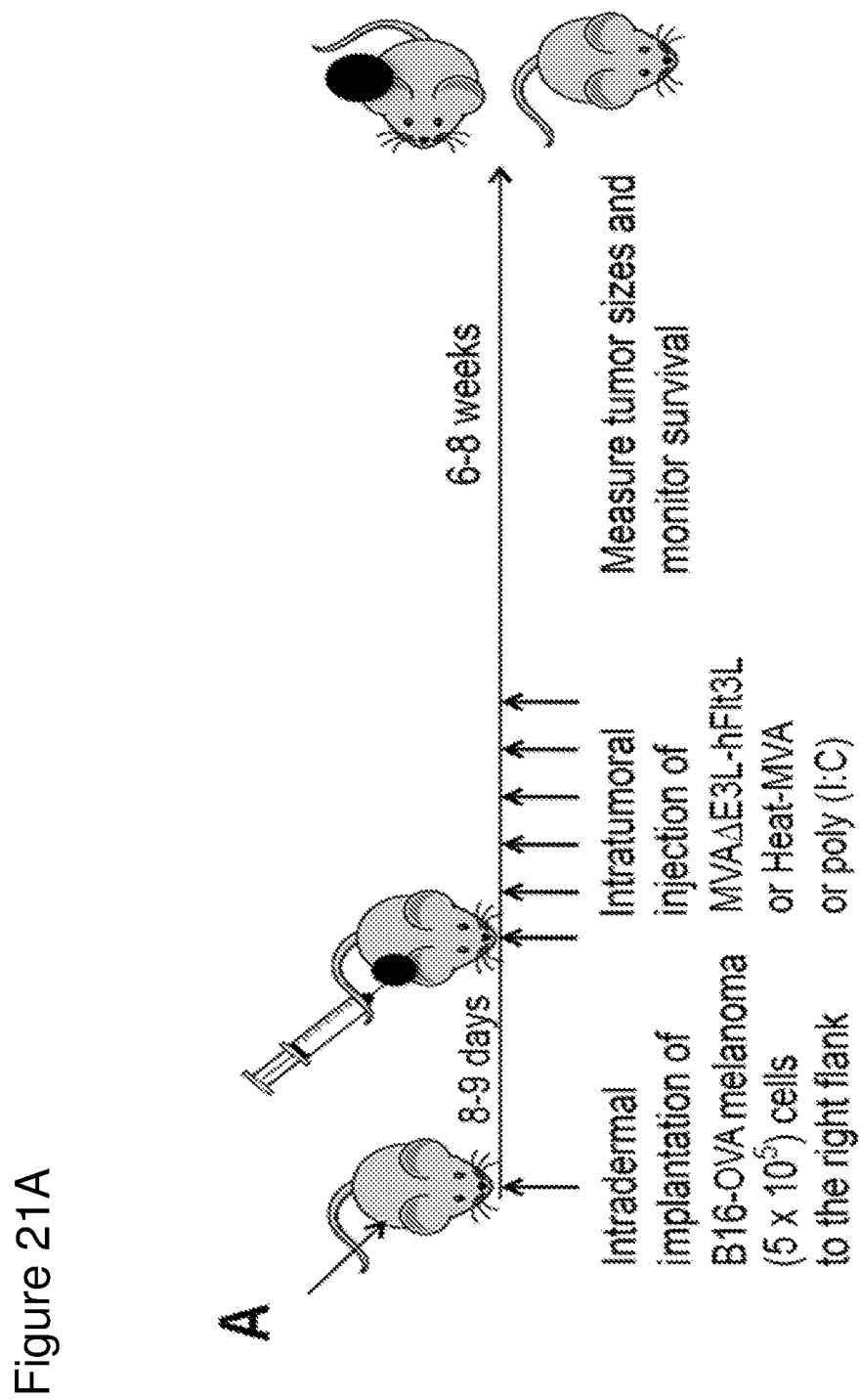
Figure 21B:
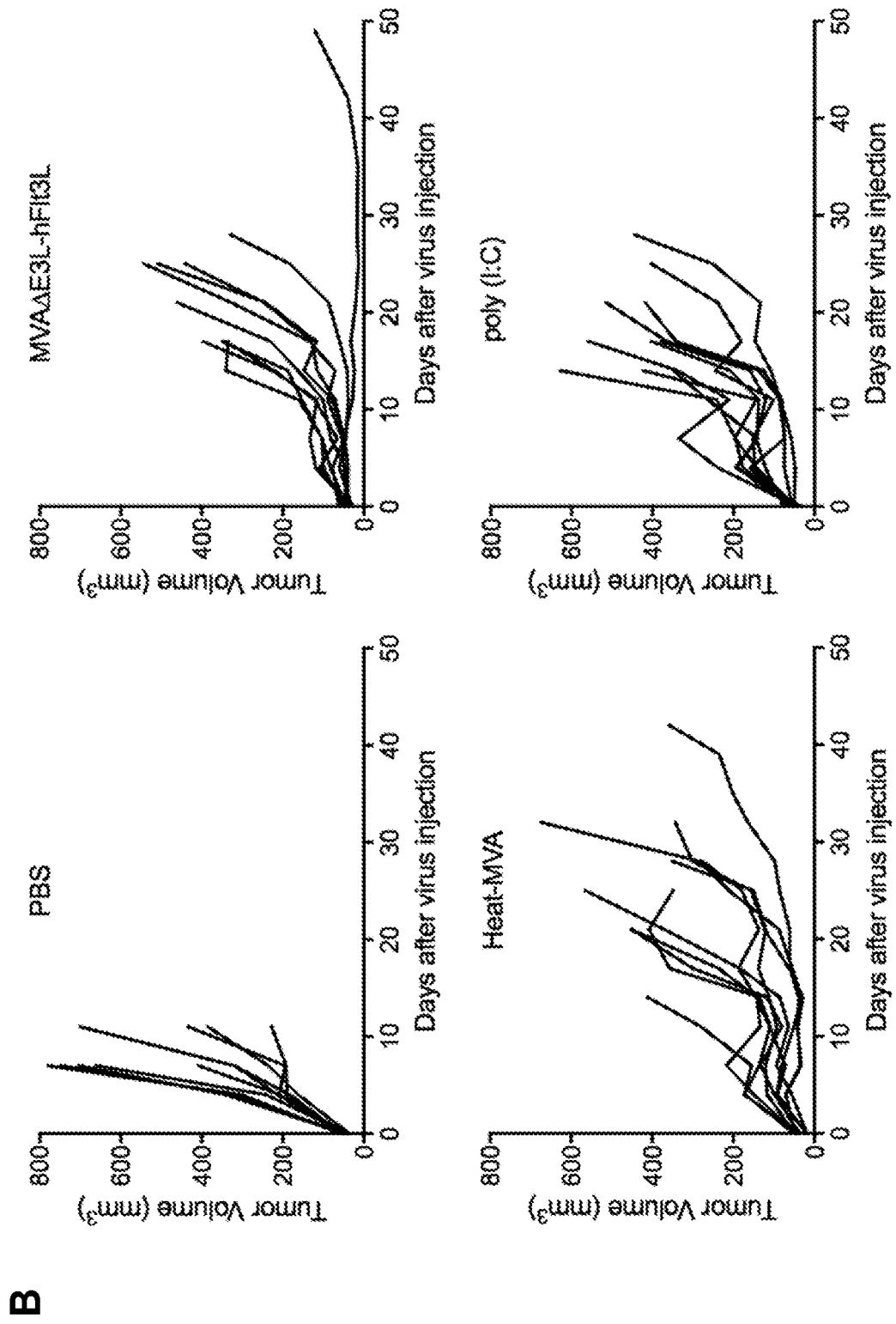

Intratumoral Injection with MVAΔE3L-hFlt3L is Effective in the Treatment of Large Established B16-OVA Melanoma in a Unilateral Tumor Implantation Model The inventors compared the anti-tumor efficacy of intratumoral injection of MVAΔE3L-hFlt3L with Heat-inactivated MVA (Heat-MVA) or poly (I:C) in a large established B16-OVA unilateral tumor implantation model. In this experiment, B16-OVA melanoma that constitutively express ovalbumin (OVA) ($5 \times 10^5$ cells in a volume of 50 μL) were implanted intradermally into the shaved skin on the right flank of WT C57BL/6J mice. After 9 days post implantation, tumor sizes were measured and tumors that are 5-6 mm in diameter were injected with MVAΔE3L-hFlt3L ($2 \times 10^7$ pfu), or Heat-iMVA (equivalent of $2 \times 10^7$ pfu of MVA), or poly (I:C), or with PBS twice weekly. Mice were monitored daily and tumor sizes were measured twice a week (FIG. 21A). Intratumoral injection of MVAΔE3L-hFlt3L was efficacious in delaying tumor growth in all of the treated mice (FIG. 21B). It also extended the median survival from 9 days in PBS-treated mice to 23 days in MVAΔE3L-hFlt3L-treated mice (FIG. 21D, P<0.0001, MVAΔE3L-hFlt3L vs. PBS). The initial tumor volumes at the time injections were started were similar in each experimental group, with an average tumor volume of 45 $mm^3$ (FIG. 21C). Intratumoral injection of Heat-MVA in large established tumors was also effective and the median survival of Heat-MVA-treated mice was extended to 26.5 days (FIG. 21D, P<0.0001, Heat-MVA vs. PBS). Poly (I:C), a synthetic dsRNA, is an innate immune agonist. Extracellular poly (I:C) can activate the endosomal localized Toll-like receptor 3 (TLR3), whereas intracellular poly (I:C) can activate the cytosolic dsRNA sensor Melanoma Differentiation-Associated protein 5 (MDA5). Because $CD103^+$ DC in the tumor microenvironment and $CD8\square^+$ DC in the tumor draining lymph nodes express higher levels of TLR3, poly (I:C) could be an effective immune modulator for the cross-presenting DCs (Salmon et al., Immunity 2016). Intratumoral injection of poly I:C (50 μg per mouse) twice weekly also led to tumor shrinkage in this large established unilateral B16-F10 melanoma model (FIG. 21B). It also extended the median survival from 9 days in PBS-treated mice to 17 days in poly (I:C)-treated mice (FIG. 21D, P<0.0001, poly (I:C) vs. PBS). Poly (I:C) appeared to be less potent than MVAΔE3L-hFlt3L or Heat-MVA, although the difference was not statistically significant (FIG. 21D). In addition, mice treated with poly (I:C) exhibited systemic illness including fatigue and wasting. It is possibly than intratumorally delivered poly (I:C) was leaked into the systemic circulation which caused immune-related side effects. The results from this experiment showed that intratumoral injection of MVAΔE3L-hFlt31 or Heat-MVA is effective in treating large established highly aggressive B16-OVA in a unilateral implantation model.

Example 18

The Combination of Intratumoral Injection with Heat-Inactivated MVA and Systemic Delivery of Immune Checkpoint Antibodies Improves Antitumor Efficacy in a Large Established Melanoma Unilateral Implantation Model The inventors further tested whether the combination of intratumoral injection of Heat-inactivated MVA (Heat-MVA) and systemic delivery of immune checkpoint blockade such as anti-CTLA-4, anti-PD-1, or anti-PD-L1 antibodies have enhanced potency in eradicating large established B16-F10 in an unilateral tumor implantation model. Briefly, B16-F10 melanoma cells ($5 \times 10^5$ cells) were implanted intradermally into the shaved skin on the right flank of WT C57BL/6J mice. After 9 days post implantation, tumors that are 5-6 mm in diameter were injected with Heat-MVA (equivalent of $2 \times 10^7$ pfu of MVA), or PBS. The mice were also treated with intraperitoneal delivery of anti-CTLA-4 antibody (100 μg per mouse), anti-PD-1 antibody (250 μg per mouse), or anti-PD-L1 (200 μg per mouse) twice weekly. Mice were monitored daily and tumor sizes were measured twice a week (FIG. 22A). Intratumoral injection of Heat-MVA was efficacious in delaying tumor growth in all of the treated mice and in eradicating the tumor in one tenth of the treated mice (FIG. 22 B). It also extended the median survival from 6 days in PBS-treated mice to 27 days in Heat-treated mice (FIG. 22D, ****, P<0.0001, Heat-MVA vs. PBS). The mean initial tumor volumes at the time injections were started 76 mm$^3$ in the PBS group and 55 mm$^3$ in the Heat-MVA+ isotype group (FIG. 22C, *, P<0.05, Heat-MVA vs. PBS). Intratumoral injection of Heat-MVA in the presence of immune checkpoint blockade anti-CTLA-4 or anti-PD-1 cured 4 out of 10 treated mice, (FIG. 22D), whereas the combination of intratumoral injection of Heat-MVA and anti-anti-PD-L1 resulted in 80% of cure of large established tumors (FIG. 22D, *, P<0.05, Heat-MVA+anti-PD-L1 vs. Heat-MVA+anti-CTLA-4 or Heat-MVA+anti-PD-1; **, P<0.01, Heat-MVA+anti-FD-L1 vs. Heat-MVA+isotype). These results showed that the combination of intratumoral injection of Heat-MVA with immune checkpoint blockade is more effective than virotherapy alone in treating large established poorly immunogenic B16-F10 in a unilateral implantation model. The combination of Heat-MVA with anti-PD-L1 antibody seems to be the most potent of all of the combinations tested. Because MVAΔE3L-hFlt3L had similar potency to Heat-MVA in this large established tumor model (Example 18, FIG. 21), it is expected that the combination of intratumoral delivery of MVAΔE3L-hFlt3L and immune checkpoint blockade would have enhanced antitumor efficacy than MVAΔE3L-hFlt3L alone in melanoma and other solid tumor models.

The above specification, examples and data provide a complete description of the manufacture and use of the composition of the invention. However, these are illustrative and nonlimiting. The breadth of the present invention resides in the claims.

All patent and literature documents cited herein are incorporated by reference in their entirety for all purposes. Any embodiment or claim feature disclosed herein can be disclaimed in Applicant's discretion.

REFERENCES

1. C. Jochems, J. Schlom, Tumor-infiltrating immune cells and prognosis: the potential link between conventional cancer therapy and immunity. *Exp Biol Med* (Maywood) 236, 567-579 (2011).
2. B. Mlecnik, G. Bindea, F. Pages, J. Galon, Tumor immunosurveillance in human cancers. *Cancer Metastasis Rev* 30, 5-12 (2011).
3. H. Angell, J. Galon, From the immune contexture to the Immunoscore: the role of prognostic and predictive immune markers in cancer. *Curr Opin Immunol* 25, 261-267 (2013).
4. F. Garrido, I. Algarra, A. M. Garcia-Lora, The escape of cancer from T lymphocytes: immunoselection of MHC class I loss variants harboring structural-irreversible "hard" lesions. Cancer *Immunol Immunother* 59, 1601-1606 (2010).
5. G. Gerlini et al., Metastatic melanoma secreted IL-10 down-regulates CD1 molecules on dendritic cells in metastatic tumor lesions. *Am J Pathol* 165, 1853-1863 (2004).
6. P. Sharma, J. P. Allison, The future of immune checkpoint therapy. *Science* 348, 56-61 (2015).
7. S. L. Topalian, C. G. Drake, D. M. Pardon, Targeting the PD-1/B7-H1(PD-L1) pathway to activate anti-tumor immunity. *Curr Opin Immunol* 24, 207-212 (2012).
8. D. H. Kim, S. H. Thorne, Targeted and armed oncolytic poxviruses: a novel multi-mechanistic therapeutic class for cancer. *Nature reviews. Cancer* 9, 64-71 (2009).
9. B. Moss, *Poxviridae: The viruses and their replication*. e. D. M. Knipe, Ed., In Fields Virology (Lippincott Williams & Wilkins, 2007), pp. pp. 2905-2946.
10. C. J. Breitbach, S. H. Thorne, J. C. Bell, D. H. Kim, Targeted and armed oncolytic poxviruses for cancer: the lead example of JX-594. *Current pharmaceutical biotechnology* 13, 1768-1772 (2012).
11. B. H. Park et al., Use of a targeted oncolytic poxvirus, JX-594, in patients with refractory primary or metastatic liver cancer: a phase I trial. *Lancet Oncol* 9, 533-542 (2008).
12. D. H. Kim, Y. Wang, F. Le Boeuf, J. Bell, S. H. Thorne, Targeting of interferon-beta to produce a specific, multi-mechanistic oncolytic vaccinia virus. *PLoS Med* 4, e353 (2007).
13. S. H. Thorne et al., Rational strain selection and engineering creates a broad-spectrum, systemically effective oncolytic poxvirus, JX-963. *J Clin Invest* 117, 3350-3358 (2007).
14. J. Engelmayer et al., Vaccinia virus inhibits the maturation of human dendritic cells: a novel mechanism of immune evasion. *J Immunol* 163, 6762-6768 (1999).
15. L. Jenne, C. Hauser, J. F. Arrighi, J. H. Saurat, A. W. Hugin, Poxvirus as a vector to transduce human dendritic cells for immunotherapy: abortive infection but reduced APC function. *Gene therapy* 7, 1575-1583 (2000).
16. P. Li et al., Disruption of MHC class II-restricted antigen presentation by vaccinia virus. *J Immunol* 175, 6481-6488 (2005).
17. L. Deng, P. Dai, W. Ding, R. D. Granstein, S. Shuman, Vaccinia virus infection attenuates innate immune responses and antigen presentation by epidermal dendritic cells. *J Virol* 80, 9977-9987 (2006).
18. R. Drillien, D. Spehner, D. Hanau, Modified vaccinia virus Ankara induces moderate activation of human dendritic cells. *J Gen Virol* 85, 2167-2175 (2004).
19. P. Dai et al., Modified vaccinia virus Ankara triggers type I IFN production in murine conventional dendritic cells via a cGAS/STING-mediated cytosolic DNA-sensing pathway. *PLoS Pathog* 10, e1003989 (2014).
20. G. Sutter, C. Staib, Vaccinia vectors as candidate vaccines: the development of modified vaccinia virus Ankara for antigen delivery. *Current drug targets. Infectious disorders* 3, 263-271 (2003).

21. C. E. Gomez, J. L. Najera, M. Krupa, M. Esteban, The poxvirus vectors MVA and NYVAC as gene delivery systems for vaccination against infectious diseases and cancer. *Curr Gene Ther* 8, 97-120 (2008).
22. C. E. Gomez, J. L. Najera, M. Krupa, B. Perdiguero, M. Esteban, MVA and NYVAC as vaccines against emergent infectious diseases and cancer. *Curr Gene Ther* 11, 189-217 (2011).
23. P. A. Goepfert et al., Phase 1 safety and immunogenicity testing of DNA and recombinant modified vaccinia Ankara vaccines expressing HIV-1 virus-like particles. *J Infect Dis* 203, 610-619 (2011).
24. L. S. Wyatt, I. M. Belyakov, P. L. Earl, J. A. Berzofsky, B. Moss, Enhanced cell surface expression, immunogenicity and genetic stability resulting from a spontaneous truncation of HIV Env expressed by a recombinant MVA. *Virology* 372, 260-272 (2008).
25. F. Garcia et al., Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase 1 clinical trial (RISVAC02). *Vaccine* 29, 8309-8316 (2011).
26. M. Tagliamonte, A. Petrizzo, M. L. Tornesello, F. M. Buonaguro, L. Buonaguro, Antigen-specific vaccines for cancer treatment. *Human vaccines & immunotherapeutics* 10, 3332-3346 (2014).
27. P. H. Verardi, A. Titong, C. J. Hagen, A vaccinia virus renaissance: new vaccine and immunotherapeutic uses after smallpox eradication. *Human vaccines & immunotherapeutics* 8, 961-970 (2012).
28. S. Hornemann et al., Replication of modified vaccinia virus Ankara in primary chicken embryo fibroblasts requires expression of the interferon resistance gene E3L. *J Virol* 77, 8394-8407 (2003).
29. H. Ludwig et al., Role of viral factor E3L in modified vaccinia virus ankara infection of human HeLa Cells: regulation of the virus life cycle and identification of differentially expressed host genes. *J Virol* 79, 2584-2596 (2005).
30. S. F. Fischer et al., Modified vaccinia virus Ankara protein F1L is a novel BH3-domain-binding protein and acts together with the early viral protein E3L to block virus-associated apoptosis. *Cell Death Differ* 13, 109-118 (2006).
31. J. C. Castle et al., Exploiting the mutanome for tumor vaccination. *Cancer Res* 72, 1081-1091 (2012).
32. T. N. Schumacher, R. D. Schreiber, Neoantigens in cancer immunotherapy. *Science* 348, 69-74 (2015).
33. I. Mellman, G. Coukos, G. Dranoff, Cancer immunotherapy comes of age. *Nature* 480, 480-489 (2011).
34. K. S. Peggs, S. A. Quezada, C. A. Chambers, A. J. Korman, J. P. Allison, Blockade of CTLA-4 on both effector and regulatory T cell compartments contributes to the antitumor activity of anti-CTLA-4 antibodies. *J Exp Med* 206, 1717-1725 (2009).
35. K. Wing et al., CTLA-4 control over Foxp3+ regulatory T cell function. *Science* 322, 271-275 (2008).
36. D. R. Leach, M. F. Krummel, J. P. Allison, Enhancement of antitumor immunity by CTLA-4 blockade. *Science* 271, 1734-1736 (1996).
37. F. S. Hodi et al., Improved survival with ipilimumab in patients with metastatic melanoma. *The New England journal of medicine* 363, 711-723 (2010).
38. C. Robert et al., Ipilimumab plus dacarbazine for previously untreated metastatic melanoma. *The New England journal of medicine* 364, 2517-2526 (2011).
39. S. L. Topalian, C. G. Drake, D. M. Pardoll, Immune checkpoint blockade: a common denominator approach to cancer therapy. *Cancer Cell* 27, 450-461 (2015).
40. D. A. Oble, R. Loewe, P. Yu, M. C. Mihm, Jr., Focus on TILs: prognostic significance of tumor infiltrating lymphocytes in human melanoma. Cancer immunity 9, 3 (2009).
41. K. E. Lacy, S. N. Karagiannis, and F. O. Nestle, Immunotherapy for Melanoma. *Expert Rev Dermatol* 7, 51-68 (2012).
42. J. D. Wolchok et al., Ipilimumab monotherapy in patients with pretreated advanced melanoma: a randomised, double-blind, multicentre, phase 2, dose-ranging study. *Lancet Oncol* 11, 155-164 (2010).
43. J. D. Wolchok et al., Nivolumab plus ipilimumab in advanced melanoma. *The New England journal of medicine* 369, 122-133 (2013).
44. O. Hamid et al., Safety and Tumor Responses with Lambrolizumab (Anti-PD-1) in Melanoma. *The New England journal of medicine*, (2013).
45. P. C. Tumeh et al., PD-1 blockade induces responses by inhibiting adaptive immune resistance. *Nature* 515, 568-571 (2014).
46. D. Zamarin et al., Localized oncolytic virotherapy overcomes systemic tumor resistance to immune checkpoint blockade immunotherapy. *Science translational medicine* 6, 226ra232 (2014).
47. M. B. Fuertes, S. R. Woo, B. Burnett, Y. X. Fu, T. F. Gajewski, Type I interferon response and innate immune sensing of cancer. *Trends Immunol* 34, 67-73 (2013).
48. M. S. Diamond et al., Type I interferon is selectively required by dendritic cells for immune rejection of tumors. *J Exp Med* 208, 1989-2003 (2011).
49. M. B. Fuertes et al., Host type I IFN signals are required for antitumor $CD8^+$ T cell responses through $CD8\{alpha\}^+$ dendritic cells. *J Exp Med* 208, 2005-2016 (2011).
50. S. R. Woo et al., STING-dependent cytosolic DNA sensing mediates innate immune recognition of immunogenic tumors. *Immunity* 41, 830-842 (2014).
51. L. Deng et al., STING-Dependent Cytosolic DNA Sensing Promotes Radiation-Induced Type I Interferon-Dependent Antitumor Immunity in Immunogenic Tumors. *Immunity* 41, 843-852 (2014).
52. J. P. Huber, J. D. Farrar, Regulation of effector and memory T-cell functions by type I interferon. *Immunology* 132, 466-474 (2011).
53. D. M. Pardoll, The blockade of immune checkpoints in cancer immunotherapy. Nature reviews. *Cancer* 12, 252-264 (2012).
54. J. Nemunaitis, Oncolytic viruses. *Invest New Drugs* 17, 375-386 (1999).
55. D. Kirn, R. L. Martuza, J. Zwiebel, Replication-selective virotherapy for cancer: Biological principles, risk management and future directions. *Nat Med* 7, 781-787 (2001).
56. M. C. Coffey, J. E. Strong, P. A. Forsyth, P. W. Lee, Reovirus therapy of tumors with activated Ras pathway. *Science* 282, 1332-1334 (1998).
57. A. Mayr, H. Stickl, H. K. Muller, K. Danner, H. Singer, [The smallpox vaccination strain MVA: marker, genetic structure, experience gained with the parenteral vaccination and behavior in organisms with a debilitated defence mechanism (author's trans1)]. *Zentralbl Bakteriol B* 167, 375-390 (1978).
58. C. Verheust, M. Goossens, K. Pauwels, D. Breyer, Biosafety aspects of modified vaccinia virus Ankara 59. G. Antoine, F. Scheiflinger, F. Dorner, F. G. Falkner, The complete genomic sequence of the modified vaccinia Ankara strain: comparison with other orthopoxviruses. *Virology* 244, 365-396 (1998).
60. A. Mayr, Hochstein-Mintzel V, SticId H., Passage history, properties, and applicability of the attenuated vaccinia virus strain MVA [in German]. *Infection* 3, 6-14 (1975).
61. H. Meyer, G. Sutter, A. Mayr, Mapping of deletions in the genome of the highly attenuated vaccinia virus MVA and their influence on virulence. *J Gen Virol* 72 (Pt 5), 1031-1038 (1991).
62. S. Brandler et al., Preclinical studies of a modified vaccinia virus Ankara-based HIV candidate vaccine: antigen presentation and antiviral effect. *J Virol* 84, 5314-5328 (2010).
63. A. Takaoka, T. Taniguchi, New aspects of IFN-alpha/beta signalling in immunity, oncogenesis and bone metabolism. *Cancer Sci* 94, 405-411 (2003).
64. D. Nagorsen, E. Wang, F. M. Marincola, J. Even, Transcriptional analysis of tumor-specific T-cell responses in cancer patients. *Crit Rev Immunol* 22, 449-462 (2002).
65. S. Pramanick, Singodia, D., and Chandel, V., Excipient selection in parenteral formulation development. *Pharma Times* 45, 65-77 (2013).
66. J. R. Weaver et al., The identification and characterization of a monoclonal antibody to the vaccinia virus E3 protein. *Virus Res* 130, 269-274 (2007).
67. M. Sato et al., Distinct and essential roles of transcription factors IRF-3 and IRF-7 in response to viruses for IFN-alpha/beta gene induction. *Immunity* 13, 539-548 (2000).
68. H. Ishikawa, G. N. Barber, STING is an endoplasmic reticulum adaptor that facilitates innate immune signalling. *Nature* 455, 674-678 (2008).
69. G. N. Barber, Innate immune DNA sensing pathways: STING, AIMII and the regulation of interferon production and inflammatory responses. *Curr Opin Immunol* 23, 10-20 (2011).
70. J. D. Sauer et al., The N-ethyl-N-nitrosourea-induced Goldenticket mouse mutant reveals an essential function of Sting in the in vivo interferon response to *Listeria monocytogenes* and cyclic dinucleotides. *Infection and immunity* 79, 688-694 (2011).
71. L. Sun, J. Wu, F. Du, X. Chen, Z. J. Chen, Cyclic GMP-AMP synthase is a cytosolic DNA sensor that activates the type I interferon pathway. *Science* 339, 786-791 (2013).
72. X. D. Li et al., Pivotal roles of cGAS-cGAMP signaling in antiviral defense and immune adjuvant effects. *Science* 341, 1390-1394 (2013).
73. J. Wu et al., Cyclic GMP-AMP is an endogenous second messenger in innate immune signaling by cytosolic DNA. *Science* 339, 826-830 (2013).
74. P. Gao et al., Structure-function analysis of STING activation by c[G(2',5')pA(3',5')p] and targeting by antiviral DMXAA. *Cell* 154, 748-762 (2013).
75. K. V. Kibler et al., Double-stranded RNA is a trigger for apoptosis in vaccinia virus-infected cells. *J Virol* 71, 1992-2003 (1997).
76. S. B. Lee, M. Esteban, The interferon-induced double-stranded RNA-activated protein kinase induces apoptosis. *Virology* 199, 491-496 (1994).
77. D. Tormo et al., Targeted activation of innate immunity for therapeutic induction of autophagy and apoptosis in melanoma cells. Cancer Cell. 2009 August 4; 16(2):103-14. doi: 10.1016/j.ccr.2009.07.004.
78. L. Gitlin et al., Essential role of mda-5 in type I IFN responses to polyriboinosinic:polyribocytidylic acid and encephalomyocarditis picornavirus. Proc Natl Acad Sci USA. 2006 May 30; 103(22):8459-64. Epub 2006 May 19.

What is claimed is:

1. A composition comprising a recombinant modified vaccinia Ankara (MVA) virus, wherein the recombinant MVA comprises MVAΔE3L harboring hFlt3L (MVAΔE3L-hFlt3L).

2. The composition of claim 1 wherein the recombinant MVAΔE3L is not harboring nucleic acid encoding or expressing a tumor antigen.

3. The composition of claim 1 further comprising one or more pharmaceutically acceptable excipients, wherein the one or more excipients is selected from the group consisting of solvents, dispersion media, coatings, antibacterial and antifungal agents, isotonic agents, absorption delaying agents, and combinations of two or more of the foregoing.

4. The composition of claim 1 wherein the composition further comprises MVA harboring a human Fms-like tyrosine kinase-3 ligand (hFlt3L) (MVA-hFlt3L).

5. The composition of claim 1 further comprising a second amount of a replication competent recombinant attenuated vaccinia virus with deletion of thymidine kinase encoding and expressing human Flt3L.

6. The composition of claim 5 further comprising a third amount of inactivated MVA.

7. A method for treating a malignant solid tumor in a subject in need thereof, the method comprising delivering to the cells of the tumor an effective amount of the recombinant modified vaccinia Ankara (MVA) virus of claim 1.

8. The method of claim 7 wherein the amount of said virus is effective to bring about one or more of the following: induce the immune system of the subject to mount an immune response against the tumor or enhance or promote an ongoing immune response by the immune system against the tumor; reduce the size of the tumor; eradicate the tumor; inhibit growth of the tumor; inhibit metastasis of the tumor; and reduce or eradicate metastatic tumor.

9. The method of claim 8 wherein the immune response against the tumor accomplishes one or more of the following:
   proliferation and activation of $CD8^+$ cytotoxic T cells;
   proliferation and activation of $CD4^+$ effector T cells;
   increase of the ratio of $CD8^+$/Treg and of Tconv/Treg;
   recruitment of $CD45^+$ cells and $CD8^+$ T cells in the injected and distant tumors;
   reduction of tumor-associated macrophages (TAM) in the injected and distant tumors;
   influx of $Ly6C^{hi}CD11b^+$ inflammatory monocytes and $Ly6C^{hi}CD11b^-$ myeloid cells into the injected and distant tumors;
   activation and mobilization of cross-presenting $CD103^+$ dendritic cells in the injected and distant tumors via the production of type IFN and proinflammatory cytokines; and
   generation of anti-tumor $CD8^+$ T cells and cross-protection against heterologous tumor(s).

10. The method of claim 7 wherein the recombinant MVA is delivered by intratumoral or intravenous injection or a simultaneous or sequential combination of intratumoral and intravenous injection.

11. The method of claim 7 wherein the tumor is melanoma or colon carcinoma.

12. The method of claim 7 wherein delivery of the recombinant MVA is continued for several weeks, months or years, or indefinitely, as long as benefits persist or a maximum tolerated dose is reached.

13. The method of claim 7 wherein the subject is a human.

14. The method of claim 7 wherein the recombinant MVA is delivered at a dosage per administration within the range of about $10^6$-$10^{10}$ plaque-forming units (pfu), wherein the delivery is repeated with a frequency within the range of from once per month to two times per week.

15. The method of claim 7, further comprising conjointly administering to the subject a second amount of an immune checkpoint blocking agent or an immune checkpoint agonist effective to block immune suppressive mechanisms within the tumor.

16. The method of claim 15 wherein the administration of the immune checkpoint blocking agent or immune checkpoint agonist is by parenteral route; or wherein the delivery of the recombinant modified vaccinia Ankara (MVA) virus is by intratumoral injection and the administration of the immune checkpoint blocking agent or immune checkpoint agonist is by intravenous route; or wherein both the delivery of the recombinant modified vaccinia Ankara (MVA) virus and the administration of the immune checkpoint blocking agent or immune checkpoint agonist are by intravenous route; or wherein both the delivery of the recombinant modified vaccinia Ankara (MVA) virus and the administration of the immune checkpoint blocking agent or immune checkpoint agonist are by intratumoral injection.

17. The method of claim 15 wherein the immune checkpoint blocking agent is selected from the group consisting of PD-1 inhibitors, PD-L1 inhibitors, CTLA4 inhibitors, inhibitory antibodies against LAG-3 (lymphocyte activation gene 3), TIM3 (T cell Immunoglobulin and Mucin-3), B7-H3, and TIGIT (T-cell immunoreceptor with Ig and ITIM domains); CD80, CD86, PDL2, B7-H4, II and DLBCL inhibitors, BTLA, and any combination thereof; and the immune checkpoint agonist is selected from the group consisting of anti-ICOS antibody, anti-OX40 antibody, agonist antibody against 4-IBB (CD 137) and against GITR.

18. A kit comprising:
a first component comprising the composition according to claim 1.

19. A method for treating a malignant tumor in a subject, wherein the subject has been previously treated or dosed with the recombinant modified vaccinia Ankara (MVA) virus of claim 1 in an amount effective to induce the immune system of the subject to mount an immune response against the tumor, the method comprising delivering to the tumor cells of the subject an amount of an immune checkpoint blocking agent effective to block immune suppressive mechanisms within the tumor elicited by tumor cells, stromal cells, or tumor infiltrating immune cells, wherein the immune checkpoint blocking agent comprises CTLA-4, CD80, CD86, PD-1, PDL1, PDL2, LAG3, B7-H3, B7-H4, TIM3, ICOS, II DLBCL inhibitors, BTLA, ipilimumab, nivolumab, pembrolizumab, pidilizumab, AMP-224, MPDL3280A, BMS-936559, MEDI4736, MSB 00107180, or any combination thereof.

20. A recombinant modified vaccinia Ankara virus with deletion of vaccinia virulence factor E3 (MVAΔE3L) modified to express human Fms-like tyrosine kinase 3 ligand (hFlt3L).

21. The kit of claim 18, further comprising a second component comprising one or both of a replication competent recombinant attenuated vaccinia virus with deletion of thymidine kinase encoding and expressing GM-CSF or human Flt3L, and inactivated MVA, respectively in a second and third amount, said second amount or third amount or both second and third amount contributing to augmenting the induced or enhanced or promoted immune response in said subject.

22. The method of claim 7, further comprising delivering to the cells of the tumor an effective amount of MVA-hFlt3L.

* * * * *

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tgtgaagacg ataaattaat gatc                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ttgtcatcat gaacggcgga                                               20

<210> SEQ ID NO 3
<211> LENGTH: 20
<212> TYPE: DNA

<213> ORGANISM: Artificial Sequence
<220> FEATURE:
<223> OTHER INFORMATION: Description of Artificial Sequence: Synthetic primer

<400> SEQUENCE: 3
tccttcgttt gccatacgct                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gaacgggact atggacgcat                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tcggtttcct cacccaatcg                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
acctgatgga taaaaaggcg                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ggcattgtgg tctacagcct                    20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gtgtttcaca gtccgtttcc g                  21

<210> SEQ ID NO 9
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 9
aacgacctat ctcctcctgc                                                      20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggctgaaag gcacatttgg                                                      20
```